US010851407B2

(12) United States Patent
Ly et al.

(10) Patent No.: US 10,851,407 B2
(45) Date of Patent: Dec. 1, 2020

(54) LEFT-HANDED GAMMA-PEPTIDE NUCLEIC ACIDS, METHODS OF SYNTHESIS AND USES THEREFOR

(71) Applicant: Carnegie Mellon University, Pittsburgh, PA (US)

(72) Inventors: Danith H. Ly, Pittsburgh, PA (US); Wei-Che Hsieh, Pittsburgh, PA (US); Iulia Sacui, Owensboro, KY (US); Arunava Manna, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 623 days.

(21) Appl. No.: 15/308,901

(22) PCT Filed: May 8, 2015

(86) PCT No.: PCT/US2015/029945
§ 371 (c)(1),
(2) Date: Nov. 4, 2016

(87) PCT Pub. No.: WO2015/172058
PCT Pub. Date: Nov. 12, 2015

(65) Prior Publication Data
US 2017/0058325 A1 Mar. 2, 2017

Related U.S. Application Data

(60) Provisional application No. 61/996,483, filed on May 8, 2014, provisional application No. 61/997,029, filed on May 20, 2014.

(51) Int. Cl.
| | | |
|---|---|---|
| *C12Q 1/68* | (2018.01) | |
| *C12Q 1/686* | (2018.01) | |
| *C07K 14/00* | (2006.01) | |
| *C12Q 1/6858* | (2018.01) | |

(52) U.S. Cl.
CPC ............ *C12Q 1/686* (2013.01); *C07K 14/003* (2013.01); *C12Q 1/6858* (2013.01)

(58) Field of Classification Search
None
See application file for complete search history.

(56) References Cited

U.S. PATENT DOCUMENTS

| | | | |
|---|---|---|---|
| 6,228,982 B1 | 5/2001 | Norden et al. | |
| 6,357,163 B1 | 3/2002 | Buchardt et al. | |
| 8,507,204 B2 | 8/2013 | Pierce et al. | |
| 8,630,809 B2 | 1/2014 | Kleinbaum | |
| 2003/0148277 A1 | 8/2003 | Chiesa et al. | |
| 2005/0260635 A1 | 11/2005 | Dirks et al. | |
| 2011/0294687 A1* | 12/2011 | Kleinbaum | G06N 3/002 506/9 |
| 2014/0128570 A1 | 5/2014 | Ly et al. | |
| 2014/0206744 A1* | 7/2014 | Kleinbaum | C12Q 1/68 514/44 A |
| 2016/0083433 A1* | 3/2016 | Ly | C12Q 1/6806 435/404 |
| 2016/0083434 A1 | 3/2016 | Ly et al. | |

FOREIGN PATENT DOCUMENTS

WO 2014169206 A2 10/2014

OTHER PUBLICATIONS

Koppelhus et al.; "Cell-Dependent Differential Cellular Uptake of PNA, Peptides, and PNA-Peptide Conjugates"; Antisense & Nucleic Acid Drug Development; 2002; pp. 51-63; vol. 12.
Kosynkina et al.; "A Convenient Synthesis of Chiral Peptide Nucleic Acid (PNA) Monomers"; Tetrahedron Letters; 1994; pp. 5173-5176; vol. 3529.
Kuhn et al.; "Hybridization of DNA and PNA Molecular Beacons to Single-Stranded and Double-Stranded DNA Targets"; J Am Chem Soc; 2002; pp. 1097-1103; vol. 124:6.
Kumar et al.; "Conformationally Constrained PNA Analogues: Structural Evolution toward DNA/RNA Binding Selectivity"; Acc. Chem. Res.; 2005; pp. 404-412; vol. 38.
Kuzyk et al.; "DNA-based self-assembly of chiral plasmonic nanostructures with tailored optical respone"; Nature; 2-12; pp. 311-314; vol. 483.
Kwon et al.; "Materials science of DNA"; J. Mater. Chem; 2009; pp. 1353-1380; vol. 19.
Li et al.; "Controlled assembly of dendrimer-like DNA"; Nature Materials; 2004; pp. 38-42; vol. 3.
Li et al.; "DNA-Templated Organic Synthesis: Nature's Strategy for Controlling Chemical Reactivity Applied to Synthetic Molecules"; Angew Chem Int Ed; 2004; pp. 4848-4870; vol. 43.
Liedl et al.; "DNA-based nanodevices"; Nano Today; 2007; pp. 36-41; vol. 2:2.
Lund et al.; "Molecular Robots Guided by Prescriptive Landscapes"; Nature; 2010; pp. 206-210; vol. 465:7295.
Lusvarghi et al.; "Loop and Backbone Modifications of PNA Improve G-Quadruplex Binding Selectivity"; J Am Chem Soc; 2009; pp. 18415-18424; vol. 131:51.
Malyshev et al.; "Solution Structure, Mechanism of Replication, and Optimization of an Unnatural Base Pair"; Chemistry; 2010; pp. 12650-12659; vol. 16:42.
Manna et al.; "Synthesis of optically pure gamma-PNA monomers: a comparative study"; Tetrahedron; 2015; pp. 3507-3514; vol. 71.
Marra S;"Selection of Fluorophore and Quencher Pairs for Fluorescent Nucleic Acid Hybridization Probes"; Methods in Molecular Biology; 2006; pp. 3-16.

(Continued)

*Primary Examiner* — Suryaprabha Chunduru
(74) *Attorney, Agent, or Firm* — The Webb Law Firm

(57) ABSTRACT

A method of making optically pure preparations of chiral γPNA (gamma peptide nucleic acid) monomers is provided. Nano structures comprising chiral γPNA structures also are provided. Methods of amplifying and detecting specific nucleic acids, including in situ methods are provided as well as compositions and kits useful in those methods. Lastly, methods of converting nucleobase sequences from right-handed helical PNA, nucleic acid and nucleic acid analog structures to left-handed γPNA, and vice-versa, are provided.

16 Claims, 18 Drawing Sheets

(56) References Cited

OTHER PUBLICATIONS

Michaelis et al.; "Amplification by nucleic acid-templated reactions"; Org. Biomol. Chem.; 2014; pp. 2821-2833; vol. 12.
Mitra et al.; "Aminomethylene Peptide Nucleic Acid (am-PNA): Synthesis, Regio-/Stereospecific DNA Binding, and Differential Cell Uptake of (alpha/gamma, R/S) am-PNA Analogues"; J. Org. Chem.; 2012; pp. 5696-5704; vol. 77.
Nielsen; "Addressing the challenges of cellular delivery and bioavailability of peptide nucleic acids (PNA)"; Quarterly Reviews of Biophysics; 2005; pp. 345-350; vol. 38:4.
Nielsen; "Peptide Nucleic Acid. A Molecule with Two Identities"; Acc. Chem. Res.; 1999; pp. 624-630; vol. 32:7.
Nielsen et al.; "Sequence-Selective Recognition of DNA by Strand Displacement with a Thymine-Substituted Polyamide"; Reports; 1991; pp. 1497-1500.
Niu et al.; "AApeptides as a new class of antimicrobial agents"; Org. Biomol. Chem.; 2013; pp. 4283-4290; vol. 11.
Oh et al.; "Excimer-Based Peptide Beacons: A Convenient Experimental Approach for Monitoring Polypeptide—Protein and Polypeptide—Oligonucleotide Interactions"; J. Am. Chem. Soc.; 2006; pp. 14018-14019; vol. 128.
Omabegho et al.; "A Bipedal DNA Brownian Motor with Coordinated Legs"; Science; 2009; pp. 67-71; vol. 324:5923.
Pianowski et al.; "Imaging of mRNA in Live Cells Using Nucleic Acid-Templated Reduction of Azidorhodamine Probes"; J. Am. Chem. Soc.; 2009; pp. 6492-6497; vol. 131.
Piccirilli et al.; "Enzymatic incorporation of a new base pair into DNA and RNA extends the genetic alphabet"; Nature; 1990; pp. 33-37; vol. 343.
Picuri et al.; "Universal Translators for Nucleic Acid Diagnosis"; J. Am. Chem. Soc.; 2009; pp. 9368-9377; vol. 131.
Pinheiro et al.; "Challenges and opportunities for structural DNA nanotechnology"; Nature Nanotechnology; 2011; pp. 763-772; vol. 6.
Poth et al.; "Discovery of Cyclotides in the Fabaceae Plant Family Provides New Insights into the Cyclization, Evolution, and Distribution of Circular Proteins"; ACS Chem. Biol.; 2011; pp. 345-355; vol. 6.
Qian et al.; "Scaling Up Digital Circuit Computation with DNA Strand Displacement Cascades"; Science; 2011; pp. 1196-1201; vol. 332.
Rajwanshi et al.; "LNA stereoisomers: xylo-LNA (beta-D-xylo configured locked nucleic acid) and alpha-L-LNA (alpha-L-ribo configured locked nucleic acid)"; Chem Commun.; 1999; pp. 1395-1396.
Ranasinghe et al.; "Linear fluorescent oligonucleotide probes with an acridine quencher generate a signal upon hybridisation"; Chem Commun; 2001; pp. 1480-1481.
Rapireddy et al.; "RTD-1 Mimic Containing gammaPNA Scaffold Exhibits Broad-Spectrum Antibacterial Activities"; J Am Chem Soc; 2012; pp. 4041-4044; vol. 134:9.
Rapireddy et al.; "Strand Invasion of Mixed-Sequence B-DNA by Acridine-Linked, gamma-Peptide Nucleic Acid (gamma-PNA)"; J Am Chem Soc; 2007; pp. 15596-15600; vol. 129.
Ratilainen et al.; "Hybridization of Peptide Nucleic Acid"; Biochemistry; 1998; pp. 12331-12342; vol. 37.
Ratilainen et al.; "Thermodynamics of Sequence-Specific Binding of PNA to DNA"; Biochemistry; 2000; pp. 1781-7791; vol. 39.
Reif; "Scaling Up DNA Computation"; Science; 2011; pp. 1156-1157; vol. 332.
Rothemund; "Folding DNA to create nanoscale shapes and patterns"; Nature; 2006; pp. 297-302; vol. 440.
Sahoo et al.; "Pyrene Excimer Fluorescence: A Spatially Sensitive Probe to Monitor Lipid-Induced Helical Rearrangement of Apolipophorin III"; Biochemistry; 2000; pp. 6594-6601; vol. 39.
Sahu et al.; "Synthesis and Characterization of Conformationally-Preorganized, MiniPEG-Containing gammaPNAs with Superior Hybridization Properties and Water Solubility"; J Org Chem; 2011; pp. 5614-5627; vol. 76:14.
Seelig et al.; "Enzyme-Free Nucleic Acid Logic Circuits"; Science; 2006; pp. 1585-1588; vol. 314.
Seitz; "Solid-Phase Synthesis of Doubly Labeled Peptide Nucleic Acids as Probes for the Real-Time Detection of Hybridization"; Angew. Chem. Int. Ed.; 2000; pp. 3249-3252; vol. 39:18.
Serpell et al.; "Precision Polymers and 3D DNA Nanostructures: Emergent Assemblies from New Parameter Space"; J Am Chem Soc; 2014; pp. 15767-15774; vol. 136.
Severcan et al.; "A polyhedron made of tRNAs"; Nat Chem; 2010; pp. 772-779; vol. 2:9.
Sforza et al.; "Chiral Peptide Nucleic Acids (PNAs): Helix Handedness and DNA Recognition"; Eur. J. Org. Chem.; 1999; pp. 197-204.
Silverman et al.; "Detecting RNA and DNA with Templated Chemical Reactions"; Chem. Rev.; 2006; pp. 3775-3789; vol. 106.
Sivakumar et al.; "A Fluorogenic 1,3-Dipolar Cycloaddition Reaction of 3-Azidocoumarins and Acetylenes"; Organic Letters; 2004; pp. 4603-4606; vol. 6:24.
Smalley et al.; "Fluorescence of covalently attached pyrene as a general RNA folding probe"; Nucleic Acids Research; 2006; pp. 152-166; vol. 34:1.
Stanzl et al.; "15 Years of Cell-penetrating, Guanidinium-rich Molecular Transporters: Basic Science, Research Tools, and Clinical Applications"; Acc Chem Res; 2013; pp. 2944-2954; vol. 46:12.
Sugiyama et al.; "Chiral Peptide Nucleic Acids with a Substituent in the N-(2-Aminoethy)glycine Backbone"; Molecules; 2013; pp. 287-310; vol. 18.
Tackett et al.; "Non-Watson-Crick interactions between PNA and DNA inhibit the ATPase activity of bacteriophage T4 Dda helicase"; Nucleic Acids Research; 2002; pp. 950-957; vol. 30:4.
Tallia et al.; "Sepsis: Improving the odds"; Perspectives; Spring 2009; pp. 6-11.
Tedeschi et al.; "Synthesis of new chiral PNAs bearing a dipeptide-mimic monomer with two lysine-derived stereogenic centres"; Tetrahedron Letters; 2005; pp. 8395-8399; vol. 46.
Tomac et al.; "Ionic Effects on the Stability and Conformation of Peptide Nucleic Acid Complexes"; J. Am. Chem. Soc.; 1996; pp. 5544-5552; vol. 118.
Van Steensel et al.; "Genomics tools for the unraveling of chromosome architecture"; Nat Biotechnol; 2010; pp. 1089-1095; vol. 28:10.
Wei et al.; "Complex shapes self-assembled from single-stranded DNA tiles"; Nature; 2012; pp. 623-626; vol. 485:7400.
Wengel; "Synthesis of 3'-C- and 4'-C-Branched Oligodeoxynucleotides and the Development of Locked Nucleic Acid (LNA)"; Acc. Chem. Res.; 1999; pp. 301-310; vol. 32.
Whyte et al.; "Master Transcription Factors and Mediator Establish Super-Enhancers at Key Cell Identity Genes"; Cell; 2013; pp. 307-319; vol. 153:2.
Winssinger et al.; "From Split-Pool Libraries to Spatially Addressable Microarrays and Its Application to Functional Proteomic Profiling"; Angew. Chem. Int. Ed.; 2001; pp. 3152-3155; vol. 40:17.
Winssinger; "Nucleic Acid-programmed Assemblies: Translating Instruction into Function in Chemical Biology"; Chimia; 2013; pp. 340-348; vol. 67:5.
Winssinger et al.; "PNA-Encoded Protease Substrate Microarrays"; Chemistry & Biology; 2004; pp. 1351-1360; vol. 11.
Wittung et al.; "DNA-like double helix formed by peptide nucleic acid"; Nature; 1994; pp. 561-563; vol. 368.
Wittung et al.; "Induced Chirality in PNA-PNA Duplexes"; Journal of the American Chemical Society; 1995; pp. 10167-10173; vol. 117:41.
Wu et al.; "Synthesis of chiral peptide nucleic acids using Fmoc chemistry"; Tetrahedron; 2001; pp. 8107-8113; vol. 57.
Yan et al.; "DNA-Templated Self-Assembly of Protein Arrays and Highly Conductive Nanowires"; Science; 2003; pp. 1882-1884; vol. 301.
Yang et al.; "Light-switching excimer probes for rapid protein monitoring in complex biological fluids"; PNAS; 2005; pp. 17278-17283; vol. 102:48.
Yeh et al.; "Crystal Structure of Chiral gamma PNA with Complementary DNA Strand—Insights into the Stability and Specificity of

(56) References Cited

OTHER PUBLICATIONS

Recognition and Conformational Preorganization"; J Am Chem Soc; 2010; pp. 10717-10727; vol. 132:31.

Yurke et al.; "A DNA-fuelled molecular machine made of DNA"; Nature; 2000; pp. 605-608; vol. 406.

Zhang et al.; "Dynamic DNA nanotechnology using strand-displacement reactions"; Nature Chemistry; 2011; pp. 103-113; vol. 3.

Zhang et al.; "Engineering Entropy-Driven Reactions and Networks Catalyzed by DNA"; Science; 2007; pp. 1121-1125; vol. 318.

Zhou et al.; "Novel Binding and Efficient Cellular Uptake of Guanidine-Based Peptide Nucleic Acids (GPNA)"; J Am Chem Soc; 2003; pp. 6878-6879; vol. 125.

Adleman.; "Molecular Computation of Solutions to Combinatorial Problems"; Science; 1994; pp. 1021-1024; vol. 266.

Aldaye et al.; "Assembling Materials with DNA as the Guide"; Science; 2008; pp. 1795-1799; vol. 321.

Ashley; "Modeling, Synthesis, and Hybridization Properties of (L)-Ribonucleic Acid"; American Chemical Society; 1992; pp. 9731-9736; vol. 114:25.

Avitabile et al.; "Gamma sulphate PNA (PNA S): Highly Selective DNA Binding Molecule Showing Promising Antigene Activity"; PLoS ONE; 2012; pp. 1-10; vol. 7:5.

Bahal et al.; "Sequence-Unrestricted, Watson-Crick Recognition of Double Helical B-DNA by (R)-MiniPEG-gammaPNAs"; ChemBioChem; 2012; pp. 56-60; vol. 13.

Bahal et al.; "Single-Stranded gammaPNAs for In Vivo Site-Specific Genome Editing via Watson-Crick Recognition"; Curr Gene Ther; 2014; pp. 331-342; vol. 14:5.

Bath et al.; "DNA nanomachines"; Nature Nanotechnology; 2007; pp. 275-284; vol. 2.

Beck et al.; "Peptide Nucleic Acid (PNA): A DNA Mimic with a Pseudopeptide Backbone"; in Artificial DNA: Methods and Applications; CRC Press; 2003; pp. 91-114.

Braasch et al.; "Synthesis, Analysis, Purification, and Intracellular Delivery of Peptide Nucleic Acids"; Methods; 2001; pp. 97-107; vol. 23.

Chen; "Expanding the rule set of DNA circuitry with associative toehold activation"; J Am Chem Soc.; 2012; pp. 263-271; vol. 134:1.

Chen et al.; "Synthesis from DNA of a molecule with the connectivity of a cube"; Nature; 1991; pp. 631-633; vol. 350.

Choi et al.; "Next-Generation in Situ Hybridization Chain Reaction: Higher Gain, Lower Cost, Greater Durability"; ACS Nano; 2014; pp. 4284-4294; vol. 8:5.

Choi et al.; "Programmable in situ amplification for multiplexed imaging of mRNA expression"; Nat Biotechnol; 2010; pp. 1208-1212; vol. 28:11.

Debaene et al.; "Synthesis of a PNA-encoded cysteine protease inhibitor library"; Tetrahedron; 2004; pp. 8677-8690; vol. 60.

De Costa et al.; "Evaluating the Effect of Ionic Strength on Duplex Stability for PNA Having Negatively or Positively Charged Side Chains"; PLoS ONE; 2013; pp. 1-8; vol. 8:3.

Delebecque et al.; "Organization of Intracellular Reactions with Rationally Designed RNA Assemblies"; Science; 2011; pp. 470-474; vol. 333.

Demidov et al.; "Stability of peptide nucleic acids in human serum and cellular extracts"; Biochemical Pharmacology; 1994; pp. 1310-1313; vol. 48:6.

Dezhenkov et al.; "Synthesis of anionic peptide nucleic acid oligomers including gamma-carboxyethyl thymine monomers"; Mendeleev Commun; 2015; pp. 47-48; vol. 25.

Dietz et al.; "Folding DNA into Twisted and Curved Nanoscale Shapes"; Science; 2009; pp. 725-730; vol. 325:5941.

Dirks et al.; "Triggered amplification by hybridization chain reaction"; PNAS; 2004; pp. 15275-15278; vol. 101:43.

Dose et al.; "Convergent Synthesis of Peptide Nucleic Acids by Native Chemical Ligation"; Organic Letters; 2005; pp. 4365-4368; vol. 7:20.

Douglas et al.; "A Logic-Gated Nanorobot for Targeted Transport of Molecular Payloads"; Science; 2012; pp. 831-834; vol. 335.

Douglas et al.; "Self-assembly of DNA into nanoscale three-dimensional shapes"; Nature; 2009; pp. 414-418; vol. 459:7245.

Dragulescu-Andrasi et al.; "A Simple gamma-Backbone Modification Preorganizes Peptide Nucleic Acid into a Helical Structure"; J. Am. Chem. Soc.; 2006; pp. 10258-10267; vol. 128.

Dueholm et al.; "Synthesis of Peptide Nucleic Acid Monomers Containing the Four Natural Nucleobases: Thymine, Cytosine, Adenine, and Guanine and Their Oligomerization"; J. Org. Chem.; 1994; pp. 5767-5773; vol. 59.

Englund et al.; "Synthesis of gamma-Substituted Peptide Nucleic Acids: A New Place to Attach Fluorophores without Affecting DNA Binding"; Organic Letters; 2005; pp. 3465-3467; vol. 7:16.

Falkiewicz et al.; "Synthesis of achiral and chiral peptide nucleic acid (PNA) monomers using Mitsunobu reaction"; Tetrahedron; 2001; pp. 7909-7917; vol. 57.

Fischer; "Einfluss der Configuration auf die Wirkung der Enzyme"; E. Ber. Dtsch. Chem. Ges.; 1894; pp. 2985-2993; vol. 27.

Frezza et al.; "Modular Multi-Level Circuits from Immobilized DNA-Based Logic Gates"; J. Am. Chem. Soc; 2007; pp. 14875-14879; vol. 129.

Fujimori et al.; "Enantio-DNA Recognizes Complementary RNA but Not Complementary DNA"; J. Am. Chem. Soc; 1990; pp. 7436-7438; vol. 112.

Gartner et al.; "DNA-Templated Organic Synthesis and Selection of a Library of Macrocycles"; Science; 2004; pp. 1601-1609; vol. 305:5690.

Gellman; "Foldamers: A Manifesto"; Acc. Chem. Res.; 1998; pp. 173-180; vol. 31.

Genot et al.; "Reversible Logic Circuits Made of DNA"; J. Am. Chem. Soc.; 2011; pp. 20080-20083; vol. 133.

Gerling et al.; "Dynamic DNA devices and assemblies formed by shape-complementary, non-base pairing 3D commponents"; Science; 2015; pp. 1446-1452. vol. 347:6229.

Griffith et al.; "Tissue Engineering—Current Challenges and Expanding Opportunities"; Science; 2002; pp. 1009-1014; vol. 295.

Gu et al.; "A Proximity-Based Programmable DNA Nanoscale Assembly Line"; Nature; 2010; pp. 202-205; vol. 465:7295.

Hammed; "DNA Computation Based Approach for Enhanced Computing Power"; International Journal of Emerging Sciences; 2011; pp. 31-37.

Han et al.; "DNA Origami with Complex Curvatures in Three-Dimensional Space"; Science; 2011; pp. 342-346; vol. 332.

Harris et al.; "Activity Profile of Dust Mite Allergen Extract Using Substrate Libraries and Functional Proteomic Microarrays"; Chemistry & Biology; 2004; pp. 1361-1372; vol. 11.

Hill et al.; "A Field Guide to Foldamers"; Chem. Rev.; 2001; pp. 3893-4011; vol. 101.

Hirao et al.; "A Synethetic Biology Approach to the Expansion of the Genetic Alphabet: Molecular Design of Unnatural Base Pairs of DNA";TCIMAIL; 2012; pp. 1-10.

Hirao et al.; "Natural versus Artificial Creation of Base Pairs in DNA: Origin of Nucleobases from the Perspectives of Unnatural Base Pair Studies"; Accounts of Chemical Research; 2012; pp. 2055-2065; vol. 45:12.

Hirao et al.; "Unnatural base pair systems toward the expansion of the genetic alphabet in the central dogma"; Proc Jpn Acad Ser B; 2012; pp. 345-367; vol. 88:7.

Huang et al.; "Preparation and Determination of Optical Purity of gamma-Lysine Modified Peptide Nucleic Acid Analogues"; Arch Pharm Res; 2012; pp. 517-522; vol. 35:3.

Janowski et al.; "Inhibiting transcription of chromosomal DNA with antigene peptide nucleic acids"; Nature Chemical Biology; 2005; pp. 210-215; vol. 1:4.

Jones et al.; "Programmable materials and the nature of the DNA bond"; Science; 2015; pp. 1260901-1-1260901-11; vol. 347:6224.

Kadhane et al.; "Strong coupling between adenine nucleobases in DNA single strands revealed by circular dichroism using synchrotron radiation"; Physical Review E; 2008; pp. 021901-1-021901-4; vol. 77.

(56) References Cited

OTHER PUBLICATIONS

Kanan et al.; "Reaction discovery enabled by DNA-templated synthesis and in vitro selection"; Nature; 2004; pp. 545-549; vol. 431.

Ke et al.; "Three-Dimensional Structures Self-Assembled from DNA Bricks"; Science; 2012; pp. 1-16; vol. 338:6111.

Kleiner et al.; "DNA-Templated Polymerization of Side-Chain-Functionalized Peptide Nucleic Acid Aldehydes"; J Am Chem Soc; 2008; pp. 4646-4659; vol. 130:14.

* cited by examiner

Scheme 1. Synthesis of LγPNA monomers starting from D-amino acids

LEFT-HANDED GAMMA-PEPTIDE NUCLEIC ACIDS, METHODS OF SYNTHESIS AND USES THEREFOR

CROSS REFERENCE TO RELATED APPLICATIONS

This application is a national stage of International Patent Application No. PCT/US2015/029945, filed May 8, 2015, which claims the benefit of U.S. Provisional Application Nos. 61/996,483, filed May 8, 2014, and 61/997,029, filed May 20, 2014, each of which is incorporated herein by reference in its entirety.

STATEMENT REGARDING FEDERAL FUNDING

This invention was made with government support under the National Science Foundation grant No. CHE-1012467. The government has certain rights in this invention.

BACKGROUND

1. Field of the Invention

Described herein are methods of detecting nucleic acids, and compositions and kits for conducting the methods. Also provided herein are methods for synthesis of chiral gamma-PNA (γPNA) compositions.

2. Description of the Related Art

Nucleic acids, particularly DNA oligonucleotides, have emerged over the last three decades as valuable tools for organizing molecular self-assembly because of their specific and predictable nucleobase interactions and defined length scale. The molecular architecture of a given system, in principle, could be determined a priori by encoding each building block with a specific recognition code whose interaction is defined by the A-T (or A-U) and C-G base-pairing and length scale defined by the 3.4 Å distance between each base-pair rung—in a manner similar to production of LEGO blocks with pegs and holes for construction of toy models. This programmable, molecular self-assembly approach has been exploited in the construction of a large variety of macro- and supra-molecular systems (nanostructures) including proteins, synthetic polymers, dendrimers, nanoparticles, DNA tiles and origami, as well as a slew of dynamic ensembles including molecular computing, logic circuits, nanomachines and devices, template-directed synthesis, and hybridization chain reaction (HCR). However, despite its broad utility in vitro, such a concept has rarely been exploited in the organization and assembly of materials in vivo, due largely to the enzymatic lability and lack of recognition orthogonality of the natural nucleic acid "velcros."

The primary concerns for utilization of natural nucleic acids as molecular assembly and computing elements in vivo are nucleolytic degradation and cross-hybridization with background genetic materials. Such occurrences would be counterproductive and could lead to premature disassembly of the complex, degradation of molecular signals, and induction of cytotoxicity. The rather weak base-pairing interactions of DNA or RNA also warrant the application of relatively long recognition modules, typically in the range of 15-30 nucleotides (nts) in length, in order to achieve the desired thermodynamic stability. Such a requirement places restriction on the length scale and level of compaction that could be built in a given system. Tighter binding synthetic analogues, such as locked nucleic acid (LNA), could be employed to enable the usage of shorter recognition elements; however, such a nucleic acid mimic is relatively difficult to prepare and chemically modify, and costly. Moreover, it still lacks the recognition orthogonality that is necessary for in vivo molecular assembly, despite the development of α-isomer (inversion of chirality at C2', C3' and C4'). In that respect, unnatural α-DNA or α-RNA (or "Spiegelmer") could be employed since neither can effectively recognize the natural β-counterparts; however, recognition is not entirely orthogonal. Cross hybridization still occurs, but to a lesser extent. Even if such a truly orthogonal recognition system could be developed, presently there is no simple way to interface the two enantiomeric modalities. Development of a nucleic acid system with both recognition orthogonality and information-interfaced capability will provide greater ease and flexibility in the design and execution of molecular self-assembly and computing in a living system.

SUMMARY OF THE INVENTION

Nucleic acids are an attractive platform for organizing molecular self-assembly because of their specific nucleobase interactions and defined length scale. Routinely employed in the organization and assembly of materials in vitro, however, they have rarely been exploited in vivo, due to the concerns for enzymatic degradation and cross-hybridization with the host's genetic materials. Herein we report the development of a tight-binding, orthogonal, synthetically versatile and informationally-interfaced nucleic acid platform for programming molecular interactions, with implications for in vivo molecular assembly and computing. The system consists of three molecular entities: the right-handed and left-handed conformers and a non-helical domain. The first two are orthogonal to each other in recognition, while the third is capable of binding to both, providing a means for interfacing the two conformers as well as the natural nucleic acid biopolymers (i.e. DNA and RNA). The three molecular entities are prepared from the same monomeric chemical scaffold, with the exception of the stereochemistry or lack thereof at the γ-backbone that determines if the corresponding oligo adopts a right-handed or left-handed helix, or a non-helical motif. These conformers hybridize to each other with exquisite affinity, sequence selectivity, and level of orthogonality. Recognition modules as short as 5 nucleotides in length are capable of organizing molecular assembly.

In a first aspect of the disclosure, a method of transferring sequence information of a nucleic acid, nucleic acid analog or right-handed γPNA (RγPNA) to a left-handed γPNA (LγPNA) or from an LγPNA to a nucleic acid, nucleic acid analog or RγPNA, is provided. Also provided is a method of converting a target nucleobase sequence of a nucleic acid, nucleic acid analog or RγPNA to a LγPNA, or converting a target nucleobase sequence of an LγPNA to a nucleic acid, nucleic acid analog or RγPNA.

The methods utilize achiral PNA, which can conform both to LγPNA and RγPNA, and also to nucleic acids and nucleic acid analogs, which hybridize to right-handed helical nucleic acids and nucleic acid analogs. In a first aspect, the methods comprise contacting the nucleic acid, nucleic acid analog or RγPNA having the sequence with a converter comprising a first strand of an achiral PNA having a sequence complementary to the target nucleic acid sequence of the nucleic acid, nucleic acid analog or RγPNA hybridized to a second strand of a LγPNA comprising the target nucleic acid sequence, such that when a nucleic acid, nucleic acid analog or RγPNA comprising the target sequence hybridizes to the first strand, the LγPNA is released from the converter. In a second aspect, the methods comprise contacting the LγPNA having the sequence with a converter comprising a first strand of an achiral PNA having a sequence complementary to the target nucleic acid sequence of the LγPNA hybridized to a second strand of a nucleic acid, nucleic acid analog or RγPNA comprising the target nucleic acid sequence, such that when an LγPNA comprising the target sequence hybridizes to the first strand, the nucleic acid, nucleic acid analog or RγPNA is released from the converter.

In another aspect, as indicated above, LγPNA, RγPNA, nucleic acids and nucleic acid analogs all can hybridize to achiral PNA. As such, nanostructures, e.g., macro- and supra-molecular systems as described above, are provided that comprise at least achiral PNA hybridized to LγPNA and/or RγPNA. Other nucleic acids or nucleic acid analogs can be included in the nanostructure, such as a structure comprising achiral PNA, LγPNA and one or more of a nucleic acid or a nucleic acid analog. In one embodiment, the achiral PNA is hybridized to RγPNA and not (substantially) to LγPNA, and in another embodiment, the achiral PNA is hybridized to LγPNA and not (substantially) to RγPNA.

In another aspect of the disclosure a composition is provided for use in detecting a nucleic acid. The composition comprises: (A) a sensor comprising: (i) a protecting (P) strand of achiral peptide nucleic acid and/or right-handed gamma-peptide nucleic acid (RγPNA) having an N-terminal end and a C-terminal end, comprising, in an N-terminal to C-terminal direction, a first section having nucleobase sequence n, second section having nucleobase sequence m comprising unnatural nucleobases, third section having nucleobase sequence a and fourth section having nucleobase sequence b and comprising an N-terminal cysteine, sulthydryl or protected sulthydryl group, and a thioester bond linking sections m and n; and (ii) a sensing (S) strand of RγPNA, achiral peptide nucleic acid (achiral PNA) or nucleic acid analog able to hybridize to RγPNA and to nucleic acid, having an N-terminal end and a C-terminal end, hybridized to the P strand, comprising, in an N-terminal to C-terminal direction a first section having nucleobase sequence b' complementary to sequence b, a second section having nucleobase sequence a' complementary to sequence a, a third section having nucleobase sequence n' complementary to sequence n and a fourth, toe-hold section having nucleobase sequence o', the S strand having a sequence complementary to a nucleotide sequence of a nucleic acid and comprising the target sequence, having a 5' end and a 3' end, comprising, in a 5' to 3' direction, without intervening nucleobases a first section having nucleobase sequence 0 complementary to sequence o', a second section having nucleobase sequence N complementary to sequence n', a third section having nucleobase sequence A complementary to sequence a' and a fourth section having nucleobase sequence B complementary to sequence b', wherein hybridization of the target nucleic acid to the S strand displaces the P strand, and the first section of the displaced P strand having nucleobase sequence n is removed by self-splicing; and (B) a converter comprising: (i) an achiral peptide nucleic acid (achiral PNA) having an N-terminal end and a C-terminal end, comprising, in an N-terminal to C-terminal direction, a first section having nucleobase sequence b' complementary to sequence b, a second section having nucleobase sequence a' complementary to sequence a, and a third section having nucleobase sequence m' having unnatural nucleobases complementary to sequence m; and (ii) a left-handed γPNA (LγPNA) having an N-terminal end and a C-terminal end, hybridized to the achiral PNA, comprising, in an N-terminal to C-terminal direction a first section having nucleobase sequence b complementary to sequence b' of the PNA, and a second section having nucleobase sequence a' complementary to sequence a of the PNA, wherein the displaced P strand hybridizes to the achiral PNA of the converter, displacing the LγPNA from the converter; and wherein, other than where sequences are indicated as being complementary, the sequences A, a, a', B, b, b', N, n, n', 0, o', m or m' are not complementary to each other.

The composition optionally comprises: (C) a first amplifier of LγPNA having an N-terminal end and a C-terminal end, comprising, in an N-terminal to C-terminal direction, a first section having nucleobase sequence b, a second section having nucleobase sequence c, a third section having nucleobase sequence b' and a fourth section having nucleobase sequence a'; and (D) a second amplifier of LγPNA having an N-terminal end and a C-terminal end, comprising, in an N-terminal to C-terminal direction, a first section having nucleobase sequence c'), a second section having nucleobase sequence b'), a third section having nucleobase sequence a') and a fourth section having nucleobase sequence b), wherein sequences of c and c' do not hybridize to sequences a, a', b or b'. According to one aspect, one or more adjacent sections of the sensor, converter or amplifiers have no intervening nucleobases between the sections.

According to one aspect of the disclosure, a method of amplifying a target nucleic acid sequence is provided. According to another aspect of the disclosure, a method of identifying a target nucleic acid in a sample comprising nucleic acids is provided. According to yet another aspect of the disclosure, an in-situ method for detection of a nucleic acid is provided. These methods employ the composition according to any aspect described herein, including the sensor, converter and, optionally, amplifiers, described in reference to the composition above, and involve contacting a nucleic acid comprising the target sequence, a biological sample, or a tissue or cell, with that composition, followed by detecting the displacement/production of the single-stranded LγPNA of the converter, as described herein.

According to one aspect of the methods described herein, using sequence-specific binding reactions, presence of a nucleic acid comprising a specific nucleobase sequence is converted via achiral PNA to an LγPNA initiator, which triggers an amplification cascade using two or more LγPNA hairpin amplifiers that concatenate only in the presence of the LγPNA initiator. The concatenation event is detected by any useful means, such as, without limitation, by gel, UV spectroscopy, light scattering spectroscopy (e.g., dynamic light scattering (DLS)), rheological methods (viscosity), colorimetric assay, FRET analysis, fluorescence dequenching methods (e.g., molecular beacon), fluorescence activation, enzyme-linked immunosorbent assay (ELISA), or tyramide signal amplification (TSA).

In yet another aspect of the present disclosure, a method of preparing optically pure LγPNA and RγPNA monomers are provided, using broadly-available, and inexpensive reagents. The method utilizes L-serine to produce optically pure LγPNA monomer, or RγPNA monomer products. The method comprises first preparing a dibenzylated intermediate by dibenzylating the amino group of L-serine; protecting the hydroxyl group of the side chain of the L-serine, and reducing the carboxylic acid group of the L-serine to obtain a dibenzylated intermediate having a protected hydroxyl group. The dibenzylated intermediate can then be used to prepare either left-handed or right-handed γPNA monomers.

To prepare right-handed γPNA monomers, the method comprises: mesylating, and azidatizing the dibenzylated intermediate and removing the protected hydroxyl group of the dibenzylated intermediate to obtain an azidated intermediate having an azido group and a hydroxyl group; alkylating the hydroxyl group and reducing the azido group of the azidated intermediate to obtain a primary amine intermediate; coupling the primary amine intermediate with benzyl glyoxylate to obtain a backbone intermediate having a protected primary amino group and a benzyloxy carbonyl group; deprotecting the protected primary amino group and the benzyloxy carbonyl group of the backbone intermediate and selectively protecting the backbone intermediate with a protecting group to obtain a protected backbone intermediate; and coupling the protected backbone intermediate with a nucleobase. To prepare left-handed γPNA monomer the method comprises: alkylating the hydroxyl group of the dibenzylated intermediate and deprotecting the protected hydroxyl group of the dibenzylated intermediate to obtain an alkoxy intermediate; mesylating and azidatizing the alkoxy intermediate to obtain an azidated intermediate having an azido group; reducing the azido group of the azidated intermediate to obtain a primary amine intermediate; coupling the primary amine intermediate with benzyl glyoxylate to obtain a backbone intermediate having a protected primary amino group and a benzyloxy carbonyl group; deprotecting the protected primary amino group and the benzyloxy carbonyl group of the backbone intermediate and selectively protecting the backbone intermediate with a protecting group to obtain a protected backbone intermediate; and coupling the protected backbone intermediate with a nucleobase. The nucleobase can be any suitable nucleobase, for example and without limitation, nucleobases are independently selected from the group consisting of A, G, C, T, U, unnatural nucleobases or divalent nucleobases. In one aspect, the chiral γPNA monomer produced by the method is optically pure. Any protecting group can substitute for the specifically-listed protecting groups.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

The methods and compositions described herein are capable of many variations in detailed implementation, which may be derived from the description contained herein by a person of ordinary skill in the art.

Figure 1:
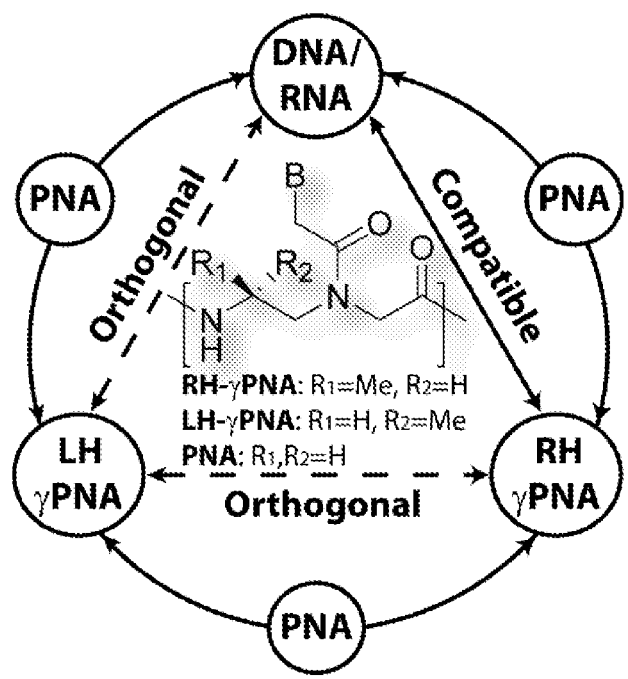
FIG. 1 is a diagram showing compatibility and incompatibility of nucleic acids with RγPNA, achiral PNA (PNA) and LγPNA.

As used herein, the term "nucleic acid" refers to deoxyribonucleic acids (DNA) and ribonucleic acids (RNA). Nucleic acid analogs include, for example and without limitation: 2'-O-methyl-substituted RNA, locked nucleic acids, unlocked nucleic acids, triazole-linked DNA, peptide nucleic acids, morpholino oligomers, dideoxynucleotide oligomers, glycol nucleic acids, threose nucleic acids and combinations thereof including, optionally ribonucleotide or deoxyribonucleotide residue(s). An oligonucleotide may be referred to by the length (i.e. number of nucleotides) of the strand, through the nomenclature "-mer". For example, an oligonucleotide of 22 nucleotides would be referred to as a 22-mer. The peptide nucleic acids, nucleic acids and analogs thereof, comprise a nucleobase sequence and can bind specifically to each other with certain limitations as shown in FIG. 1. The structure of PNA is remarkably simple and consists of repeating N-(2-aminoethyl)-glycine units linked by amide bonds. The purine (adenine (A), guanine (G)) and pyrimidine (cytosine (C), thymine (T), uridine (U)) bases are attached to the backbone through methylene carbonyl linkages. Unlike DNA or DNA analogs, PNAs do not contain any (pentose) sugar moieties or phosphate groups. PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as evidence by their higher melting temperatures (Tm). This high thermal stability has been attributed to the neutrality of the PNA backbone, which does not encounter the charge repulsion present in DNA or RNA duplexes. Two strands can hybridize together, or two portions of a single strand can hybridize to form a secondary structure (e.g., in a hairpin) within the same strand.

In a first aspect of the disclosure, a method of transferring sequence information of a nucleic acid, nucleic acid analog or right-handed γPNA (RγPNA) to a left-handed γPNA (LγPNA) or from an LγPNA to a nucleic acid, nucleic acid analog or RγPNA, is provided. Also provided is a method of converting a target nucleobase sequence of a nucleic acid, nucleic acid analog or RγPNA to a LγPNA, or converting a target nucleobase sequence of an LγPNA to a nucleic acid, nucleic acid analog or RγPNA. As shown in FIG. 1, the methods go in both directions, using achiral PNA, which can conform both to LγPNA and RγPNA, and also to nucleic acids and nucleic acid analogs, which hybridize to right-handed helical nucleic acids and nucleic acid analogs. In a first aspect, the methods comprise contacting the nucleic acid, nucleic acid analog or RγPNA having the sequence with a converter comprising a first strand of an achiral PNA having a sequence complementary to the target nucleic acid sequence of the nucleic acid, nucleic acid analog or RγPNA hybridized to a second strand of a LγPNA comprising the target nucleic acid sequence, such that when a nucleic acid, nucleic acid analog or RγPNA comprising the target sequence hybridizes to the first strand, the LγPNA is released from the converter. In a second aspect, the methods comprise contacting the LγPNA having the sequence with a converter comprising a first strand of an achiral PNA having a sequence complementary to the target nucleic acid sequence of the LγPNA hybridized to a second strand of a nucleic acid, nucleic acid analog or RγPNA comprising the target nucleic acid sequence, such that when an LγPNA comprising the target sequence hybridizes to the first strand, the nucleic acid, nucleic acid analog or RγPNA is released from the converter.

In another aspect, as indicated above, LγPNA, RγPNA, nucleic acids and nucleic acid analogs all can hybridize to achiral PNA. As such, nanostructures are provided that comprise at least achiral PNA hybridized to LγPNA and/or RγPNA. Other nucleic acids or nucleic acid analogs can be included in the nanostructure, such as a structure comprising achiral PNA, LγPNA and one or more of a nucleic acid or a nucleic acid analog. In one embodiment, the achiral PNA is hybridized to RγPNA and not (substantially) to LγPNA, and in another embodiment, the achiral PNA is hybridized to LγPNA and not (substantially) to RγPNA, recognizing the synthesis methods provided herein that permit production of optically purer preparations of RγPNA and LγPNA monomers.

Figure 2:
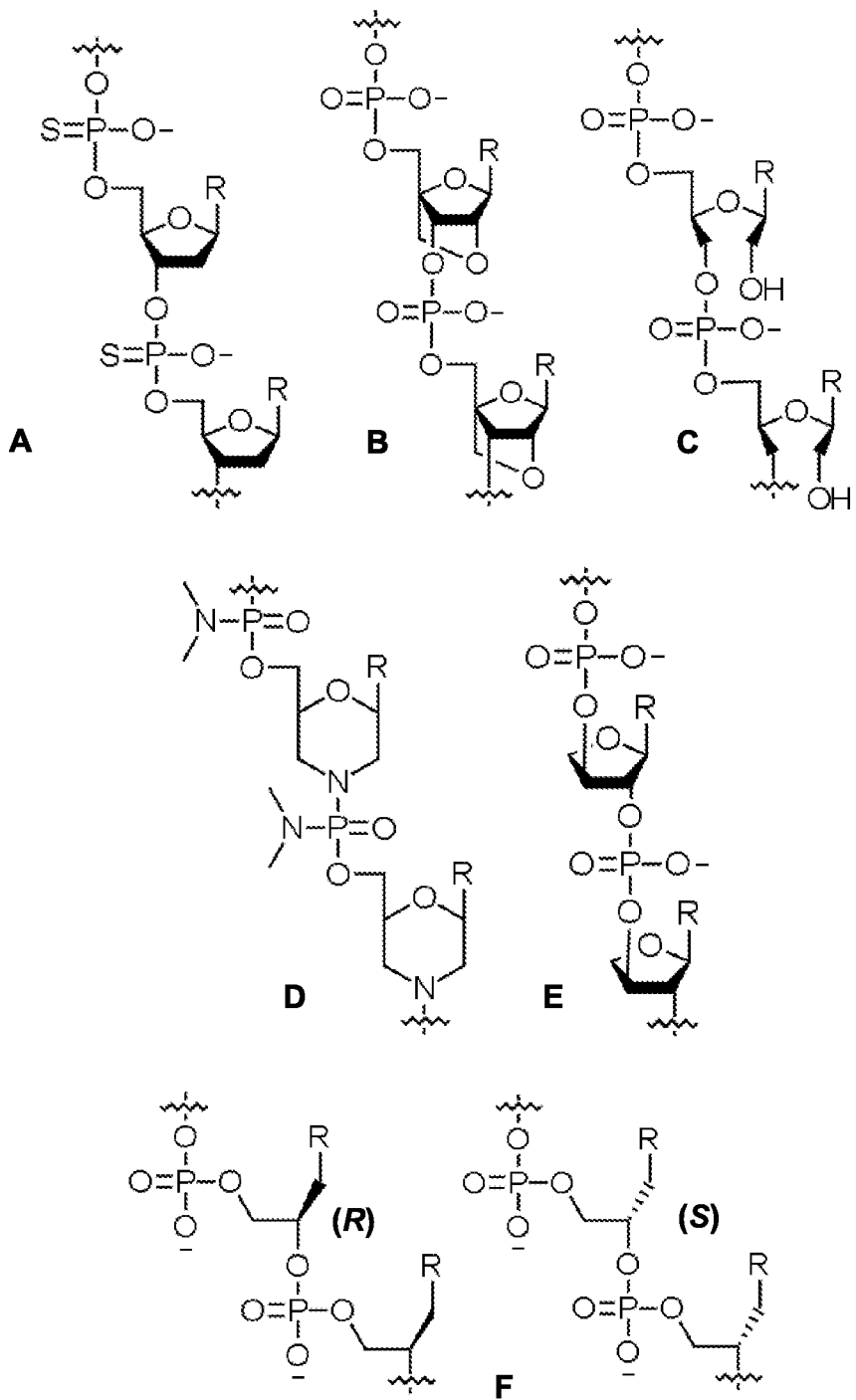
FIGS. 2(A-F) provide exemplary structures for nucleic acid analogs.

Nucleic acid analogs are broadly-known and are polymers having a sequence of nucleobases and a backbone. Nucleic acid analogs, in the context of all aspects of the disclosure presented herein, can hybridize to achiral PNA, RγPNA, LγPNA, RNA, or DNA by Watson-Crick base pairing, as with A binding T/U or C binding G, or Watson-Crick-like base-pairing, as in the case of unnatural nucleobases, such as isoC binding isoG. Non-limiting examples of common nucleic acid analogs include peptide nucleic acids, such as γPNA, phosphorothioate (e.g., FIG. 2A), locked nucleic acid (2'-O-4'-C-methylene bridge, including oxy, thio or amino versions thereof, e.g., FIG. 2B), unlocked nucleic acid (the C2'-C3' bond is cleaved, e.g., FIG. 2C), 2'-O-methyl-substituted RNA, morpholino nucleic acid (e.g., FIG. 2D), threose nucleic acid (e.g., FIG. 2E), glycol nucleic acid (e.g., FIG. 2F, showing R and S Forms), etc. FIG. 2A-2F shows monomer structures for various examples of nucleic acid analogs. FIGS. 2A-2F each show two monomer residues incorporated into a longer chain as indicated by the wavy lines. Incorporated monomers are referred to herein as "residues" and the part of the nucleic acid or nucleic acid analog oligomer or polymer excluding the nucleobases is referred to as the "backbone" of the nucleic acid or nucleic acid analog. As an example, for RNA, an exemplary nucleobase is adenine, a corresponding monomer is adenosine triphosphate, and the incorporated residue is an adenosine monophosphate residue. For RNA, the "backbone" consists of ribose subunits linked by phosphates, and thus the backbone monomer is ribose triphosphate prior to incorporation and a ribose monophosphate residue after incorporation.

Sequences of nucleic acids are written in their 5' to 3' orientation. Complementarity refers to a relationship between two structures that follow a simple lock-and-key principle. Complementarity is a property shared between two nucleic acid sequences, such that when aligned, the nucleotide bases at each position in the sequences are complementary, i.e. they are able to bind to, or hybridize with one another. Complementarity, also refers to the concept of purine nucleotide bases complementing, or being able to bind to and/or hybridize with, pyrimidine nucleotide bases. For example, complementarity in DNA and RNA occur between A and T, or A and U, and C and G (i.e., A-T/U, T/U-A, G-C or C-G). This concept of complementarity between nucleotide bases is referred to and known in the art as Watson-Crick base pairing. Reverse complementation refers to the idea that two sequences are complementary to one another when aligned in an antiparallel manner. The two sequences are in a sense, mirror images of one another. Antiparallel refers to the concept of two biopolymers, for example DNA or RNA, having opposite alignments. In DNA and RNA, opposite alignment refers to the 5'-phosphoryl end of one sequence being aligned to the 3'-hydroxyl end of another sequence. When two strands of nucleic acid are hybridized, they do so by reverse complementation, that is, a first strand in a 5' to 3' orientation hybridizes to a strand in its 3' to 5' orientation. Thus, the sequence 5'-ATGC-3' hybridizes to a nucleic acid having the sequence: 5'-GCAT-3', and are considered to be "complementary". Sequences of nucleic acid analogs, such as PNAs are expressed in an orientation-specific manner as the 5' to 3' convention with respect to nucleic acids. Thus an achiral PNA or RγPNA having the sequence $N_{term}$-GCAT-$C_{term}$ will hybridize to the nucleic acid having the reverse-complementary sequence 5'-ATGC-3', and thus are considered "complementary." When two strands or nucleic acids, achiral PNA and γPNA are said to be hybridized, it is meant that they are hybridized in water, normal saline, PBS, isotonic or other aqueous solutions with similar salt concentrations (e.g., ±5%, 10%, 15% or 20%) at a temperature in the range of 25° C. to 50° C., for example at 45° C., 40° C., 37° C., 35° C., 30° C. or room temperature (e.g., 21° C.±5° C.). For any kit, composition or reaction as described herein that is to be transported and used in a variety or ambient temperatures, such as outdoors in hot weather, it is preferred that the duplexed and hairpin reagents remain in their duplexed or hairpin states until they are displaced or converted by introduction of a target nucleic acid sequence.

Figure 22:
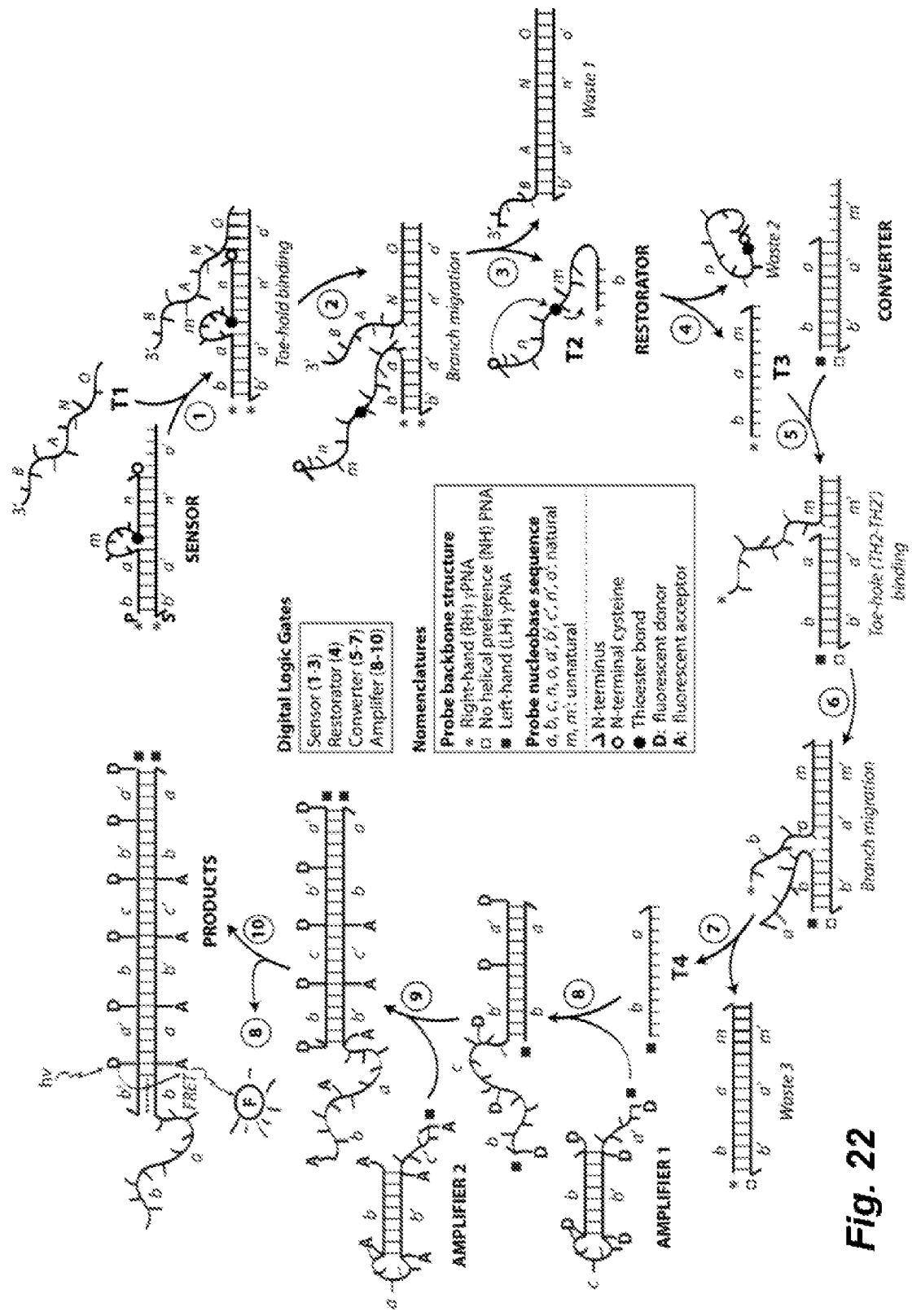
FIG. 22 illustrates the I-NADSA molecular operations.
Figure 23:
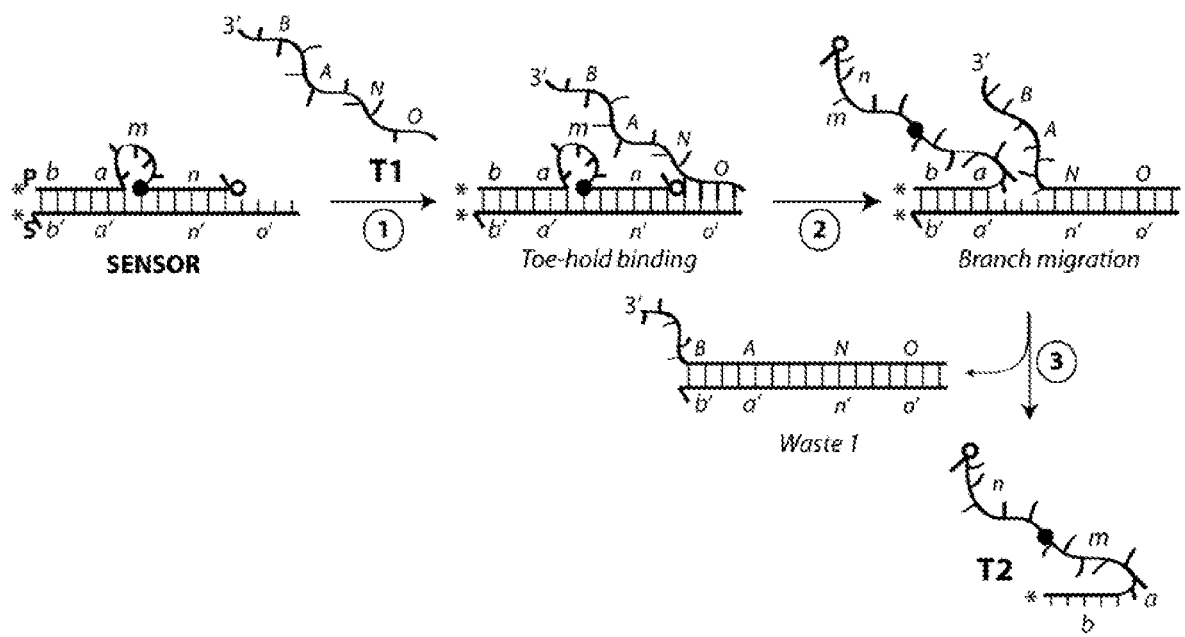
FIG. 23 illustrates the sensor of Example 2, which is comprised of a protecting (P) strand and sensing (S) strand hybridized to one another to form a 'frustrated' hairpin structure m with unnatural nucleobases as recognition elements.

In terms of the nucleic acids, peptide nucleic acids, and left-handed and right-handed γPNAs described herein, strands or portions thereof that hybridize together are complementary and are in reverse-complementary orientation to each other, as in Watson-Crick base pairing. Sections and sequences of each nucleic acid, peptide nucleic acid or γ-peptide nucleic acid are described as being in a particular sequential order, and a complementary nucleic acid or peptide nucleic acid (generally, referred to as a complementary sequence) has the respective complementary sections and sequences thereof in complementary orientation. As an example, as shown in FIG. 22, the Sensor has a P strand with a sequential order of sections or sequences of n-a-b in an N-terminal to C-terminal direction. The sensor S strand has a sequential order of sections and sequences of b'-a'-n' in an N-terminal to C-terminal direction. The sequences of the P strand and the S strand of the sensor are said to be in complementary orientation because they hybridize directly and in order:

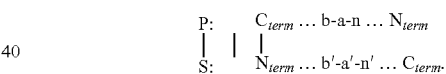

Likewise, strands or portions thereof that have the same nucleobase sequence, and the same orientation of sections, even though they may have different backbones (such as nucleic acid, achiral PNA, or right- or left-handed γPNA), are said to have the same orientation. Thus, in FIG. 22, the target nucleic acid having the sections, 5' to 3' N-A-B has the same orientation as the P strand of the sensor ($N_{term}$ n-m-a-b $C_{term}$) even though the P strand has an intervening sequence/section m, and as the left-handed γPNA of the converter ($N_{term}$ a-b $C_{term}$) even though the left-handed γPNA omits the additional sequence/section n.

The methods described herein are applicable to any specific nucleotide sequence, the specific hybridization of which according to standard Watson-Crick base pairing to a complementary sequence is expected to apply to any sequence of nucleobases, and thus one of ordinary skill would recognize that listing the of the specific nucleobase sequence of any of the sections would be unnecessary and superfluous. Thus any section of any length described herein comprises a sequence of any permutation of the nucleobases A, G, C and T/U or an unnatural nucleobase, for each nucleobase. Thus, the target nucleic acid can comprise any sequence of nucleobases, and includes a sequence (5' to 3') of sections O-N-A-B, which can be any useful sequence, the methods described herein are expected to operate correctly for any such useful sequence. That said, in a given genome, transcriptome and/or exome, it is most desirable to select a sequence for the target sequence that presents a unique sequence in the genome, transcriptome and/or exome to ensure the accuracy of the described assay.

A PNA monomer, such as an achiral PNA monomer, an RγPNA monomer or an LγPNA monomer, incorporated into a PNA oligomer or polymer, is referred to herein as a "PNA monomer residue", with each residue having the same or different nucleobase, such as adenine, guanine, cytosine, thymine and uracil bases, unnatural nucleobases, or other nucleobases, such that the order of bases on the γPNA is its "sequence", as with DNA or RNA. The PNA, nucleic acid or nucleic acid analog monomers and residue structures illustrated herein show a backbone monomer or a backbone monomer residue, respectively, attached to a nucleobase (R). A sequence of nucleobases in a PNA, nucleic acid or a nucleic acid analog oligomer or polymer, such as a γPNA oligomer or polymer, binds to a complementary sequence of adenine, guanine, cytosine, thymine and/or uracil residues in a nucleic acid strand by cooperative bonding, essentially as with Watson-Crick binding of complementary bases in double-stranded DNA or RNA. "Watson-Crick-like" bonding refers to hydrogen bonding of nucleobases other than G, A, T, C or U, such as the bonding of the unnatural bases shown herein with each other.

A "peptide nucleic acid" refers to a DNA or RNA mimic in which the sugar phosphodiester backbone of the DNA or RNA is replaced by a N-(2-aminoethyl)glycine unit. A gamma PNA (γPNA) is an oligomer or polymer of gamma-modified N-(2-aminoethyl)glycine monomers of the following structure:

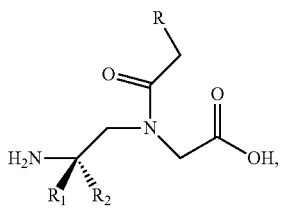

where at least one of R1 or R2 attached to the gamma carbon is not a hydrogen, such that the gamma carbon is a chiral center. When R1 and R2 are hydrogen (N-(2-aminoethyl)-glycine backbone), there is no such chirality about the gamma carbon, and the resultant PNA is achiral PNA, often referred to in the art simply as "PNA". An incorporated achiral PNA or γPNA monomer,

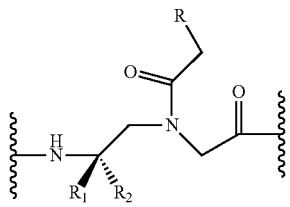

is referred to herein as an achiral PNA or γPNA "residue", with each residue having the same or different R group as its base (nucleobase), such as adenine, guanine, cytosine, thymine and uracil bases, or other bases, such as the unnatural (e.g., orthogonal) bases described herein, such that the order of bases on the PNA is its "sequence", as with DNA or RNA.

A sequence of nucleobases in a nucleic acid or a nucleic acid analog oligomer or polymer, such as an achiral PNA or γPNA oligomer or polymers, binds to a complementary sequence of adenine, guanine, cytosine, thymine, uracil or unnatural residues in a nucleic acid or nucleic acid analog strand by nucleobase pairing, essentially as with double-stranded DNA or RNA. The following depict residue structures for achiral PNA (1), Left-handed γPNA (2) and right-handed γPNA (3).

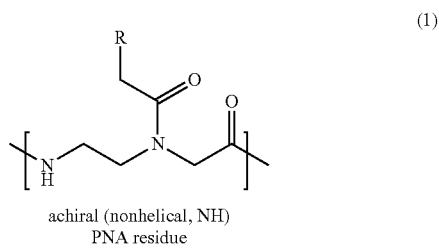

achiral (nonhelical, NH) PNA residue

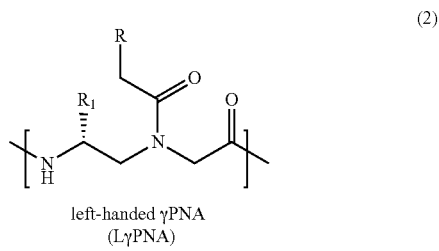

left-handed γPNA (LγPNA)

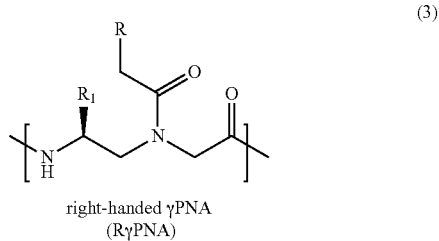

right-handed γPNA (RγPNA)

R1s each independently are selected from the group consisting of H (for achiral PNA), an amino acid side chain, a substituted amino acid sidechain, linear or branched ($C_1$-$C_8$)alkyl, ($C_2$-$C_8$)alkenyl, ($C_2$-$C_8$)alkynyl, ($C_1$-$C_8$)hydroxyalkyl, ($C_1$-$C_8$)thiolalkyl, ($C_1$-$C_8$) aminoalky, ($C_1$-$C_8$) azidoalkyl, ($C_3$-$C_8$)aryl, ($C_3$-$C_8$)cycloalkyl, ($C_3$-$C_8$)aryl($C_1$-$C_6$) alkylene, ($C_3$-$C_8$)cycloalkyl($C_1$-$C_6$)alkylene, —$CH_2$—($OCH_2$—$CH_2$)$_q$$OP_1$, —$CH_2$—($OCH_2$—$CH_2$)$_q$—$NHP_1$, —$CH_2$—($OCH_2$—$CH_2$-$0$)$_q$—$SP_1$, —$CH_2$—($SCH_2$—$CH_2$)$_q$—$SP_1$, —$CH_2$—($OCH_2$—$CH_2$)$_r$—OH, —$CH_2$—($OCH_2$—$CH_2$)$_r$—$N_3$, —$CH_2$—($OCH_2$—$CH_2$)$_r$—$NH_2$, —$CH_2$—($OCH_2$—$CH_2$), —NHC(NH)$NH_2$, or —$CH_2$—($OCH_2$—$CH_2$)$_r$—S—S[$CH_2CH_2$]$_8$NHC(NH)$NH_2$, where P1 is selected from the group consisting of H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl ($C_1$-$C_6$)alkylene, substituted ($C_1$-$C_8$)alkyl, substituted ($C_2$-$C_8$)alkenyl, substituted ($C_2$-$C_8$)alkynyl, substituted ($C_1$-$C_8$) hydroxyalkyl, substituted ($C_3$-$C_8$)aryl, substituted ($C_3$-$C_8$) cycloalkyl, substituted ($C_3$-$C_8$)aryl($C_1$-$C_6$)alkylene, substituted ($C_3$-$C_8$)cycloalkyl($C_1$-$C_6$)alkylene, substituted —$CH_2$—($OCH_2$—$CH_2$)$_q$$OP_1$, substituted —$CH_2$—($OCH_2$—$CH_2$)$_q$—$NHP_1$, substituted —$CH_2$—($OCH_2$—$CH_2$-$0$)$_q$—$SP_1$, substituted —$CH_2$—($SCH_2$—$CH_2$)$_q$—$SP_1$, substituted —$CH_2$—($OCH_2$—$CH_2$)$_r$—OH, substituted —$CH_2$—($OCH_2$—$CH_2$)$_r$—$NH_2$, substituted —$CH_2$—

(OCH$_2$—CH$_2$)$_r$—NHC(NH)NH$_2$, or substituted —CH$_2$—(OCH$_2$—CH$_2$)$_r$—S—S[CH$_2$CH$_2$]$_s$NHC(NH)NH$_2$, where P1 is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl (C$_1$-C$_6$)alkylene; q is an integer from 0 to 50, inclusive, r and s are each independently integers from 1 to 50, inclusive, a polyether, a diether, an amino acid, and a polypeptide of from 2 to 25 amino acid residues, wherein the substituted moieties are substituted with one or more halo (e.g., F, Cl or Br), linear or branched (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, amino acid side chain, amino acid, oligopeptide of from 2 to 25 residues, or hereroatom (e.g., S, O, N or P). By "substituted amino acid side chain", it is meant an amino acid sidechain, such as a substituted lysine, arginine, serine, or cysteine sidechain, that is substituted with a group, such as an amino acid or oligopeptide, a (C$_1$-C$_8$) hydrocarbyl group, or, with any group listed above for R1. According to one aspect the substituted amino acid side chain is not substituted with a second substituted amino acid side chain, or alternately, the substituted amino acid side chain is not substituted with a second substituted amino acid side chain substitute with a further substituted amino acid side chain.

Certain embodiments of the P strand of the sensor has the following alternate structures, with either a sulthydryl group (e.g., as with a cysteine) or a disulfide group at its N-terminal or C-terminal.

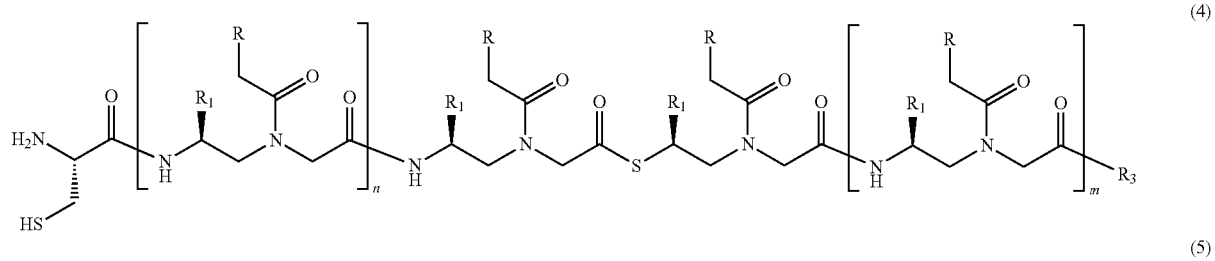

(4)

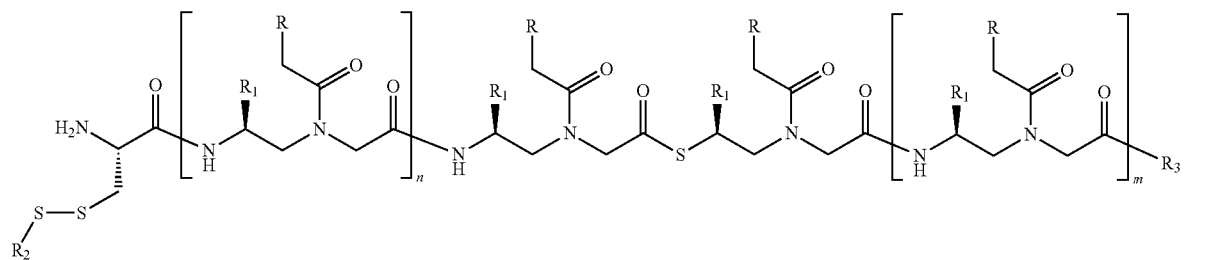

(5)

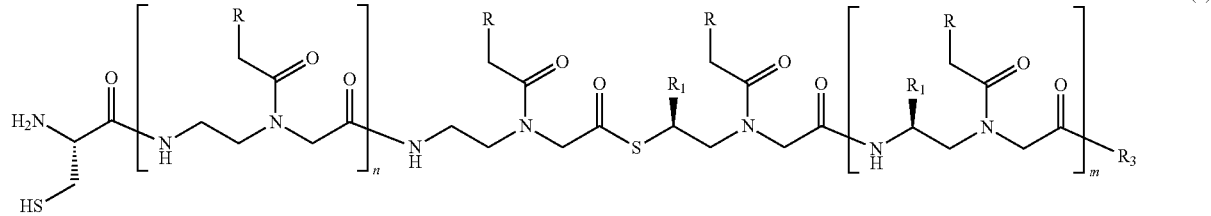

(6)

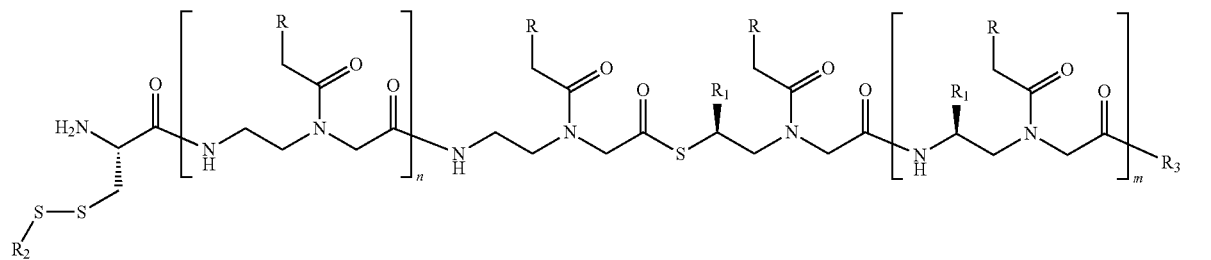

(7)

where each instance of R is, independently a nucleobase that either forms hydrogen bonds with nucleobases of natural nucleic acids (e.g., A, T/U, G, or C), or unnatural nucleic acids. Values for n and m are each, independently from 1 to 25, 1-20, 5-10, and any increment therebetween. In the structure P of the sensor, the sequence n falls between the terminal sulthydryl and the internal thioester, with the sequence m of unnatural nucleobases being immediately adjacent to the internal thioester opposite to the sequence n. R1 is as described above. R2 is one or more amino acid residues, an amino acid side chain, linear, branched or hetero-substituted (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, or (C$_3$-C$_8$)cycloalkyl (C$_1$-C$_6$)alkylene. R3 is —OH or —NH$_2$. Formulas (4), (5), (6) and (7) each depict an N-terminal Cysteine providing the N-terminal sulfhydryl, with formulas (6) and (7) depicting R1 as being H for the n sequence of the described P strand, affording additional backbone flexibility of achiral PNA, as compared to RγPNA when R1 is not H, for the self-splicing "restorator" step in which the n sequence of P is removed. R3 is —OH or $NH_2$.

A nucleobase is a nitrogenous base of a nucleotide. Natural nucleobases are adenine (A), guanine (G), cytosine (C), thymine (T) and uracil (U). Natural nucleobases include modified versions of A, G, C, T and U, but still bind to (are complementary to or hybridize to) one of A, G, C, T and U. An "unnatural nucleobase" used herein synonymously with an "orthogonal nucleobase" is a nucleobase that does not hybridize, or hybridizes unfavorably to one of the natural nucleobases: A, G, C or T/U. Unnatural nucleobases can hybridize (base-pair) to other unnatural nucleobases. As used herein, portions of the γPNA reagents include unnatural or orthogonal nucleobase sequences, where those sequences hybridize specifically to sequences of complementary unnatural or orthogonal bases. Examples of unnatural bases and orthogonal base pairs are described herein, as well as in, for example, Hirao, I, et al. (A Synthetic Biology Approach to the Expansion of the Genetic Alphabet: Molecular Design of Unnatural Base Pairs of DNA" TCIMAIL, No. 148, Tokyo Chemical Industry Co. Ltd., August 2012 and HIRAO, Ichiro, et al., "Unnatural Base Pair Systems toward the Expansion of the Genetic Alphabet in the Central Dogma." Ed. Takao SEKIYA. *Proceedings of the Japan Academy. Series B, Physical and Biological Sciences* 88.7 (2012): 345-367). Non-limiting examples of unnatural base pairs include: Isoguanine (isoG, 6-amino-2-ketopurine) with isocytosine (isoC, 2-amino-4-ketopyrimidine); xanthine with diaminopyridine; 2-amino-6-dimethylaminopurine (x) with 2-oxopyridine (y); 6-amino-5-nitro-3-(1'-13-D-2'-deoxyribofuranosyl)-2(1H)-pyridone (dZ) with 2-amino-8-(1'-β-D-2'-deoxyribofuranosyl)-imidazo[1,2-a]-1,3,5-triazin-4 (8H)-one (dP); 5SCIS with MMO2; 5SCIS with NaM (Malyshev, Denis A. et al. "Solution Structure, Mechanism of Replication, and Optimization of an Unnatural Base Pair." *Chemistry (Weinheim an Der Bergstrasse, Germany)* 16.42 (2010): 12650-12659); with 7-(2-thienyl)imidazo[4,5-b]-pyridine (Ds) with pyrrole-2-carbaldehyde (Pa).

RγPNA and LγPNA relate to other classes of nucleic acids, both natural and synthetic, in that it contains nucleobases (A, C, G, T, U, unnatural nucleobases, or other synthetic analogues) and thus is capable of hybridizing to its partner strand through hydrogen-bonding and base-stacking interactions, either in accordance with the Watson-Crick base-pairing rule—in which the adenine nucleobase (A) is paired with thymine (T) or uridine (U), and cytosine (C) with guanine (G), or the equivalent Watson-Crick-like base-pairing for unnatural bases.

LγPNA differs from other classes of nucleic acids in that it adopts a left-handed helical motif and does not hybridize to complementary DNA or RNA strand, or any other classes of nucleic acids for that matter that fold into a right-handed helix, including all previously reported γPNAs. LγPNA will hybridize to another LγPNA strand with a complementary sequence; however, it will not hybridize to DNA or RNA, or γPNA prepared from L-amino acids (with the exception of L-serine, L-cysteine and related chiral amino acids, which can be made to fold into either a right-handed or left-handed helix depending on the nature of chemical transformations-another aspect of this invention), because of the conformational mismatch.

One aspect of the present invention relates to the synthesis of gamma-peptide nucleic acids (γPNAs) with a left-handed helical fold (LγPNA). Unlike other classes of nucleic acid mimics that have been developed to date, which either adopt a random fold, such as glycol nucleic acid (GNA) and peptide nucleic acid (PNA), or a right-handed helical motif, such as phosphorothioate DNA, 2'-O-methyl RNA, morpholino phosphoroamidate, locked nucleic acid (LNA), and all previously reported γPNAs which were prepared from L-amino acids, this new class of chiral γPNAs (or LγPNA) adopt a left-handed helical motif and hybridize to one another with exquisite avidity and sequence specificity, in accordance with the Watson-Crick base-pairing rules.

The left-handed helical fold renders LγPNA impervious to hybridization with natural nucleic acid biopolymers such as DNA or RNA. This conformational orthogonality, combined with the exquisite binding affinity and sequence specificity and ease of synthesis and chemical group functionalization, makes LγPNAs attractive as molecular tags for drug discovery (N. Winssinger, J. L. Harris, B. J. Backes, P. G. Schultz, Angew. Chem.-Int. Edit. Engl. 40, 3152 (2001); N. Winssinger, S. Ficarro, P. G. Schultz, J. L. Harris, Proc. Nat!. Acad. Sci. USA 99, 11139 (2002); F. Debaene, L. Mejias, J. L. Harris, N. Winssinger, Tetrahedron 60, 8677 (2004); J. L. Harris et al., Chern. Bioi. 11, 1361 (2004); and N. Winssinger et al., Chern. Bioi. 11, 1351 (2004)); recognition codes for organizing molecular self-assembly (J. H. Chen, N.C. Seeman, Nature 350, 631 (1991); S. M. Douglas et al., Nature 459, 414 (2009); Y.-W. Kwon, C. H. Lee, D.-H. Choi, J.-1. Jin, J Mater. Chern. 19, 1353 (2009); D. Y. Zhang, G. Seelig, Nat. Chern. 3, 103 (2011); F. A. Aldaye, A. L. Palmer, H. F. Sleiman, Science 321, 1795 (2008); and A. V. Pinheiro, D. Han, W. M. Shih, H. Yan, Nat. Biotech. 6, 763 (2011)); template-directed synthesis (Z. J. Gartner et al., Science 305, 1601 (2004); M. W. Kanan, M. M. Rozenman, K. Sakurai, M. M. Snyder, D. R. Liu, Nature 431, 545 (2004)); hybridization chain reaction (HCR) (R. M. Dirks, N. A. Pierce, Proc. Nat. Acad. Sci. US.A. 101, 15275 (2004); H. M. T. Choi et al., Nat. Biotech. 28, 1208 (2010)); logic gate/circuit designs (D. Y. Zhang, A. J. Turberfield, B. Yurke, E. Winfree, Science 318, 1121 (2007); G. Seelig, D. Soloveichik, D. Y. Zhang, E. Winfree, Science 314, 1585 (2006); B. M. Frezza, S. L. Cockroft, M. R. Ghadiri, JAm. Chern. Soc. 129, 14875 (2007); J. M. Picuri, B. M. Frezza, M. R. Ghadiri, JAm. Chern. Soc. 131, 9368 (2009); and 20. L. Qian, E. Winfree, Science 332, 1196 (2011)); molecular computations (S. M. Douglas, I. Bache let, G. M. Church, Science 335, 831 (2012); J. H. Reif, Science 332, 1156 (2011)); construction of nano-size materials and molecular devices (B. Yurke, A. J. Turberfield, A. P. Mills, F. C. Simmel, J. L. Neumann, Nature 406, 605 (2000); H. Z. Gu, J. Chao, S. J. Xiao, N. C. Seeman, Nature 465, 202 (2011); K. Lund et al., Nature 465, 206 (2010)); development of biomaterials for tissue engineering and regenerative medicine (L. G. Griffin, G. Naughton, Science 295, 1009 (2002)); capturing reagents for biomolecule (DNA, RNA, proteins, carbohydrates, and other biological machineries); pull-down and purification (B. van Steensel, J. Dekker, Nat. Biotech. 28, 1089 (2010); W. A. Whyte et al., Cell 153, 307 (2013)); and peptide therapeutics (S. Rapireddy et al., JAm. Chern. Soc. 134, 4041 (2012); A. G. Poth et al., ACS Chern. Bioi. 6, 345 (2011); S. H. Gellman, Ace. Chern. Res. 31, 173 (1998); D. J. Hill, M. J. Mio, R. B. Prince, T. S. Hughes, J. S. Moore, Chern. Rev. 101, 3893 (2001)).

Because LγPNA does not hybridize to a complementary DNA or RNA strand, it can be used in many of the aforementioned applications where hybridization of probes or molecular recognition "tags" to the endogenous nucleic acid molecules such as DNA or RNA is a concern. One such example is the construction of molecular circuits (or logic gates) in live cells and intact organisms for detection and treatment of genetic and infectious diseases. Of particular significance is the application of PNA to convert a right-handed input into a left-handed γPNA output, and vice versa, via a chain-migration mechanism. A second example is hybridization chain reaction (an in-situ signal amplification method) for detection of nucleic acids (such as DNA and RNA) and other biopolymers. A third example is combinatorial synthesis and screening of chemical libraries in drug discovery. In all cases, unintended hybridization of probes or molecular recognition "tags" to endogenous nucleic acid molecules such as DNA and RNA, which is a likely scenario due to their high abundance in the cellular environments, would lead to non-productive binding events, or disruption in the signals (or messages) being relayed or the structures being built, due to inadvertent sequestration of the probes or molecular recognition "tags".

Because of its conformational and hybridization orthogonality, LγPNA can be used to program molecular recognition and self-assembly in the cellular environments without the concern for inadvertent binding of probes with endogenous nucleic acid materials. Also, because of its extraordinary high binding affinity, relatively short probes (3-8 nucleotides in length) can be used to perform many of the aforementioned molecular recognition and self-assembly tasks. This provides many distinct advantages over the longer ones (typically 15-50 nucleotides in length commonly used today) in terms of ease of synthesis, cost of production, recognition specificity, and cell penetration and systemic delivery. Other advantages that LγPNA (as well as RγPNA) has over the other classes of nucleic acid mimics are ease and flexibility of chemical modifications and enzymatic stability. The ability to incorporate other chemical functionalities into LγPNA with ease is essential to further fine-tuning and improving its properties toward a particular application in biology and medicine—a task that would otherwise be difficult (if not impractical) to achieve with other classes of nucleic acid molecules.

LγPNA can be chemically derivatized in such a way that it is soluble in organic solvents, such as dichloromethane, acetonitrile, tetrahydrofuran (THF), and hexane. Other nucleic acid molecules, even those as small as individual building blocks, without the nucleobase protection (which is required for base-pairing) are generally not miscible with these commonly used organic solvents. Because LγPNA can be soluble in organic solvents, it can be used to organize and assemble "smart" polymeric and macro-scale materials whose structures and functions are determined by the input stimuli because Watson-Crick recognition is still maintained in these solvents.

Further, since LγPNA is synthetic, made of unnatural polyamide backbone, it is not recognized or easily degraded by proteases or nucleases. As such, it can be used in many of these intracellular (or in vivo) applications without the concern for enzymatic degradation that would render the probes useless, or in the case of randomly-folded and right-handed helical nucleic acids, inadvertent binding to endogenous nucleic acid materials that would cause hybridization short-circuit or elicit undesired molecular consequences.

With regard to synthesis of γPNAs, the synthetic route, as shown in Example 2, below, enables the production of both the right-handed (RγPNA) as well as the left-handed (LγPNA) monomers on a commercial scale from a common and relatively cheap starting material (L-serine in this case, but also applicable to L-cys), without the concern for racemization.

There are currently other methods for detection of nucleic acids. Current methods for nucleic acid-based diagnostics and the respective advantages and disadvantages of each are described below. Further, Tables 1 and 2, below, provide a partial list of Human Genetic Tests and Microbial Tests, respectively, based on nucleic acid detections currently on the U.S. market. However, unlike the methods described herein, these methods are not performed in-situ. Further, the current methods are labor intensive, time-consuming, prone to cross-contamination and false positives, and also require the use of an enzyme. As such, there exists a need for a rapid, convenient means for diagnosing genetic and infectious diseases in a laboratory setting as well as in the field.

Nucleic acid-based diagnostics generally rely on four core assay technologies. In PCR or RT-PCR, DNA (or RNA reverse transcribed to cDNA) is amplified to detect the presence of a pathogen or host gene of interest. This allows for sensitive detection, but requires a highly skilled technician and laboratory equipment. The amplified material can contaminate subsequent samples. Isothermal amplification is similar to PCR, but uses simplified amplification techniques that operate at a single temperature. Examples of isothermal methods include: Transcription mediated amplification (TMA); Signal-mediated amplification of RNA technology (SMART); Strand displacement amplification (SDA); Rolling circle amplification (RCA); Loop-mediated isothermal amplification of DNA (LAMP); Isothermal multiple displacement amplification (HAD); Single primer isothermal amplification (SPIA); Circular helicase-dependent amplification (cHDA); and Branched DNA signal amplification (bDNA). In these assays, DNA is amplified which allows for sensitive detection, simplified isothermal amplification is more amenable to point-of-care devices/low-resource settings, however, this newer technology that has not been extensively clinically validated, amplified material can contaminate subsequent samples. Hybridization techniques, such as FISH and DNA microarray technologies benefit from no risk of contamination of new samples with amplified material, but because the target DNA is not amplified, the techniques can be less sensitive and requires highly skilled technician and laboratory equipment. Sequencing involves identification of the specific genetic code (sequence) for an amplified piece of DNA or the full genome of an organism. Beyond confirming the presence of a pathogen, sequencing can provide detailed information about the original and unique characteristics of the pathogen in a specific patient, not practical for low-resource settings. However, sequencing techniques are expensive, time consuming, and require both a highly skilled technician and expensive laboratory equipment.

A multitude of nucleic acid-based assays are known and are commercially-available, and the target nucleic acids and sequences thereof are broadly-known. Those unique sequence can be utilized as target sequences for the assays described herein, such as the I-NADSA assay described below. A large number of commercially-available nucleic acid-based assays are listed in Tables 2 and 3 of parent patent application, U.S. Provisional Patent Application No. 61/996,483, which is incorporated herein by reference in its entirety (see, Tables 1 and 2, below, providing a partial listing of those assays provided in Tables 2 and 3 of U.S. Provisional Patent Application No. 61/996,483, which is publicly available from the U.S. Food and Drug Administration as a list of nucleic acid-based tests that have been cleared or approved by the Center for Devices and Radiological Health). Listing the many thousands of developed and/or commercially available PCR, isothermal amplification, hybridization and target-specific probes herein is unnecessary, as one of ordinary skill can either use the same unique sequences used in the assay as the target sequence for the assays described herein, or can readily ascertain if any sequence of any target gene is unique in a genome, transcriptome or exome by either searching a publicly-available database, such as GenBank, for the target sequence, or by conducting a preliminary hybridization or PCR experiment using the target sequence to ascertain if there will be cross-reactivity with other sequences in a sample to be analyzed.

TABLE 1

Human Genetic Tests (Nucleic Acid-Based Detections)

| Manufacturer | Disease | Trade name | Method | Submission |
| --- | --- | --- | --- | --- |
| Abbot Molecular, Inc. | Acute myeloid leukemia | Vysis D7S486/CEP 7 FISH Probe Kit | FISH Cytogenetic | K131508 |
| | | Vysis EGR1 FISH Probe Kit | FISH Cytogenetic | K123951, K091960 |
| Nanostring Technologies | Breast cancer | Prosigna Breast Cancer Prognostic Gene Signature Assay | Hybridization Gene profiling | K130010 |
| Illumina, Inc. | Cystic fibrosis | Illumina MiSeqDx Fibrosis Clinical Sequencing Assay | Sequencing | K132750 |
| | | Illumina MiSeqDx Cystic Fibrosis 139-Variant Assay | Sequencing | K124006 |
| Luminex Molecular Diagnostics, Inc. | Drug metabolizing enzymes | xTAG CYP2D6 Kit v3 | PCR & Hybridization | K1301189, K093420 |
| Hologics, Inc. | Coagulation factors | Invading Factor V | Hybridization SNP | K100980 |
| | | Invading Factor II | Hybridization SNP | K100943 |
| | | Invader MTHFR 677 | Hybridization SNP | K100987 |
| | | Invader MTHFR 1298 | Hybridization SNP | K100496 |
| xDx | Heart transplant | AlloMap Molecular Expression Testing | RT-PCR Gene profiling | K073482 |
| Affymetrix, Inc. | Chromosome abnormalities | Affymetrix CytoScan Dx Assay | Hybridization Gene profiling | K130313 |
| Iris Molecular Diagnostics | Prostate cancer | NADiA ProsVue | qPCR | K101185 |

TABLE 2

Microbial Tests (Nucleic Acid-Based Detections)

| Manufacturer | Microorganisms | Trade name | Method | Submission |
| --- | --- | --- | --- | --- |
| Argene SA | Adenovirus | Adenovirus R-gene US | RT-PCR | K121942 |
| Idaho Technology, Inc. | *Bacillus Anthracis* | IBAIDS Anthrax Detection System | RT-PCR | K131930, K071188, K051713 |
| Microprobe Corp. | *Candida tropicalis/Candida albicans/Candida parapsilosis/Candida glabrata/Candida krusei* | Affirm VPIII Microbial Identification Test | | K931151, K931374 |
| PrimeraDx | *Clostridium difficile* | ICEPlex *C. difficile* Kit | PCR, separation | K132726 |
| Idaho Technology, Inc. | *Coxiella burnetii* | Joint Biological Agent Identification and Diagnostics System (JBAIDS) Q Fever Detection Kit | RT-PCR | K103207 |
| Hologic/ Gen-Probe, Inc. | *Chlamydia trachomatis/Neisseria gonorrhoeae* | Aptima Combo 2 Assay | NA Amplification | K132251 |
| Roche Molecular Systems | Cytomegalovirus | COBAS AmpliPrep/COBAS TaqMan CMV Test | RT-PCR | P110037, S001-S002 |
| Center for Disease Control and Prevention | Dengue virus | CDC DENV-1-4 Real-Time RT-PCR Assay | TaqMan | K113336 |
| Intelligent Medical Devices, Inc. | *Entercoccus* | IMDx Van R for Abbott m2000 | PCR | K123753 |
| bioMerieux, Inc. | Enterovirus | NucliSens EasyQ Enterovirus v1.1 Assay | RT-PCR | K093383 |

TABLE 2-continued

Microbial Tests (Nucleic Acid-Based Detections)

| Manufacturer | Microorganisms | Trade name | Method | Submission |
|---|---|---|---|---|
| AdvanDx | *Escherichia coli/Klebsiella pneumonia/Pseudomonas aeroginosa* | GNR Traffic Light PNA FISH | | K101558 |
| | | *E. coli/P. aeroginosa* PNA FISH | | K081309, K092393 |
| | | E*K/P aeruginosa* PNA FISH | | K092393, K081433 |
| | | *E. coli* PNA FISH | | K082068 |
| Idaho Technology, Inc. | *Francisella tularensis* | JBAIDS Tularemia Detection Kit | | K072547 |
| Nanosphere, Inc. | Gram-Positive/Gram-Negative Bacteria Herpes Simplex Virus | Verigene Gram-Positive Blood Culture Nucleic Acid Test (BC-GP) | | K122514, K113450 |
| Abbott Molecular, Inc. | Hepatitis virus | Abbot RealTime HCV Genotype II | | P120012 |
| | | Abbott RealTime HCV Assay | | P100017, S001-S006 |
| | | Abbott RealTime HBV Assay | | P080026, S001-S004 |
| Quidel Corporation | Human Metapneumovirus | Quidel Molecular RSV + hMPV Assay | | K131813, K122189 |
| | | Quidel Molecular hMPV Assay | | K112490 |
| Gen-Probe, Inc. | Human papillomavirus | Aptima HPV Assay | | P100042 |
| | | Aptima HPV 16 18/45 Genptype Assay | | P120007 |
| Gen-Probe Prodesse, Inc. | Influenza and respiratory viruses | Prodesse ProFAST Assay | | K132237 |
| US Army Medical Material Development Activity | *Leishmania* species | SMART Leish | | K081868 |
| Cepheid | *Mycobacterium* tuberculosis | Xpert MTB/RIF Assay | | M131706 |
| Gen-Probe, Inc. | *Mycobacterium* species | Accuprobe *Mycobacterium avium* complex culture | | K921435, K896494, K897078 |
| | | Accuprobe *Mycobacterium kansasii* Identification Test | | K904463 |
| | | Accuprobe *Mycobacterium intracellular* Culture Identification Test | | K897077 |
| | | Accuprobe *Mycobacterium gordonae* culture identification Test | | K896492 |
| | | Rapid Diagnostic System for *Mycobacterium gordonae* | | K890089 |
| | | Rapid Diagnostic System for Mycobacteria | | K864597 |
| | | Rapid Identification Test for *Mycobacterium avium* | | K862613 |
| | | Gen-Probe *Mycobacterium* Rapid Confirmation System | | K860782 |
| Meridian Bioscience, Inc. | *Mycoplasma pneumonia* Multiplex Panel | Illumigene *Mycoplasma* DNA Amplification Assay | | K123423 |
| BD Diagnostics (GeneOhm Sciences Canada, Inc.) | *Staphylococcus* | BD Max MRSA Assay | | K120138 |
| Cepheid | Streptococci | Xpert GBS LB Assay | | K121539 |
| Gen-Probe, Inc. | *Trichomonas vaginalis* | Aptima *Trichomonas vaginalis* assay | | K102911 |
| Idaho Technology, Inc. | *Yersinia pestis* | JBAIDS Plague Detection Kit | | K072631 |

HPA: Hybridization protection assay
LCR: Ligase chain reaction

An example of where the paradigm "early detection equals better outcomes" is especially true is the syndrome sepsis, a continuum of events triggered by the body's inflammatory immune responses to bacterial, viral, fungal, or parasitic infections. Sepsis is a major killer globally, despite significant advances in treatment of infectious disease and improvements in clinical care. Once a patient is septic, the survival rate drops 6% every hour. Therefore, early diagnosis of sepsis is important for patient survival. Various analytes show promise as markers for identifying septic patients. Tallia S, Kunicka J E. Sepsis: Improving the Odds. Perspectives; Spring 2009: 6-11. However, there is still a need for faster and more reliable tests and markers for a quick diagnosis, e.g. less than 30 minutes from testing.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

By "expression" or "gene expression," it is meant the overall flow of information from a gene (without limitation, a functional genetic unit for producing a gene product, such as RNA or a protein in a cell, or other expression system encoded on a nucleic acid and comprising: a transcriptional promoter and other cis-acting elements, such as response elements and/or enhancers; an expressed sequence that typically encodes a protein (open-reading frame or ORF) or functional/structural RNA, and a polyadenylation sequence), to produce a gene product (typically a protein, optionally post-translationally modified or a functional/ structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene.

Provided herein are sequence-based logic reactions that allow for extremely accurate molecular events and detection within a complex system such as within a cell, cell lysate, tissue, blood, saliva, bodily fluid (such as sweat), urine, or feces. U.S. Pat. No. 8,630,809 describes a simple type of such sequence-based logic reactions. In the methods and compositions described herein, by incorporating a conversion from native "R" configured helical structures and conformations, to "L" configured structures, the system is simplified, cleverly sidestepping the possibility of competing reactions and reactants that may be present in a system, such as in the system described in U.S. Pat. No. 8,630,809.

The system described herein relies in one aspect on the ability of nucleic acids to hybridize both to achiral and RγPNA, but not to LγPNA. As above, FIG. 1, depicts the compatibility and incompatibility of nucleic acids with RγPNA, achiral PNA (PNA) and LγPNA, in the context of the depicted PNA where either R1 or R2 is methyl. By conversion via hybridization to PNA, FIG. 1 is a diagram showing compatibility and incompatibility of nucleic acids with RγPNA, achiral PNA (PNA) and LγPNA. By "orthogonal," it is meant that a nucleic acid, nucleic acid analog or nucleobase does not hybridize to natural nucleic acids, DNA or RNA with the natural nucleobases A, C, G and/or T/U, but that it can function in one or more aspects like nucleic acids, such as by sequence-specific hybridization.

According to one aspect of the methods described herein, using sequence-specific binding reactions, presence of a nucleic acid comprising a specific nucleobase sequence is converted via achiral PNA to an LγPNA initiator, which triggers an amplification cascade using two or more LγPNA hairpin amplifiers that concatenate only in the presence of the LγPNA initiator. The concatenation event is detected by any useful means, such as, without limitation, by gel, UV spectroscopy, light scattering spectroscopy (e.g., dynamic light scattering (DLS)), rheological methods (viscosity), colorimetric assay, FRET analysis, fluorescence dequenching methods (e.g., molecular beacon), fluorescence activation, enzyme-linked immunosorbent assay (ELISA), or tyramide signal amplification (TSA). FRET analysis and excimer formation are described below in the Examples.

According to one aspect of the disclosure, referencing FIGS. 20-26 and Example 4, a method of amplifying a target nucleic acid sequence is provided. According to another aspect of the disclosure, a method of identifying a target nucleic acid in a sample comprising nucleic acids is provided. According to yet another aspect of the disclosure, an in-situ method for detection of a nucleic acid is provided. These methods employ the following reagents: (A) a sensor comprising: (i) a protecting (P) strand of achiral peptide nucleic acid and/or right-handed gamma-peptide nucleic acid (RγPNA) having an N-terminal end and a C-terminal end, comprising, in an N-terminal to C-terminal direction, a first section having nucleobase sequence n, second section having nucleobase sequence m comprising unnatural nucleobases, third section having nucleobase sequence a and fourth section having nucleobase sequence b and comprising an N-terminal cysteine, sulfhydryl or protected sulfhydryl group, and a thioester bond linking sections m and n; and (ii) a sensing (S) strand of RγPNA, achiral peptide nucleic acid (achiral PNA) and/or a nucleic acid analog able to hybridize to RγPNA and nucleic acid, having an N-terminal end and a C-terminal end, hybridized to the P strand, comprising, in an N-terminal to C-terminal direction a first section having nucleobase sequence b' complementary to sequence b, a second section having nucleobase sequence a' complementary to sequence a, a third section having nucleobase sequence n' complementary to sequence n and a fourth, toe-hold section having nucleobase sequence o', the S strand having a sequence complementary to a nucleotide sequence of a nucleic acid and comprising the target sequence, having a 5' end and a 3' end, comprising, in a 5' to 3' direction, without intervening nucleobases a first section having nucleobase sequence 0 complementary to sequence o', a second section having nucleobase sequence N complementary to sequence n', a third section having nucleobase sequence A complementary to sequence a' and a fourth section having nucleobase sequence B complementary to sequence b', wherein hybridization of the target nucleic acid to the S strand displaces the P strand, and the first section of the displaced P strand having nucleobase sequence n is removed by self-splicing; and (B), a converter comprising: (i) an achiral peptide nucleic acid (achiral PNA) having an N-terminal end and a C-terminal end, comprising, in an N-terminal to C-terminal direction, a first section having nucleobase sequence b' complementary to sequence b, a second section having nucleobase sequence a' complementary to sequence a, and a third section having nucleobase sequence m' having unnatural nucleobases complementary to sequence m; and (ii) a left-handed γPNA (LγPNA) having an N-terminal end and a C-terminal end, hybridized to the achiral PNA, comprising, in an N-terminal to C-terminal direction a first section having nucleobase sequence b complementary to sequence b' of the PNA, and a second section having nucleobase sequence a' complementary to sequence a of the PNA, wherein the displaced P strand hybridizes to the achiral PNA of the converter, displacing the LγPNA from the converter. Other than where sequences are indicated as being complementary, the sequences A, a, a', B, b, b', N, n, n', O, o', m or m' are not complementary to each other (that is, sequences A and a are identical, and hybridize to a', and vice-versa, but A, a, and/or a' do not hybridize to B, b, b', N, n, n', O, o', m or m', and likewise B and b are identical, and hybridize to b', and vice-versa, but B, b, and/or b' do not hybridize to A, a, a', N, n, n', O, o', m or m', and so on). Optionally, if a hybridization chain reaction is to be used to detect the nucleic acid, the reagents also include: (C) a first amplifier of LγPNA having an N-terminal end and a C-terminal end, comprising, in an N-terminal to C-terminal direction a first section having nucleobase sequence b, a second section having nucleobase sequence c, a third section having nucleobase sequence b' and a fourth section having nucleobase sequence a'; and (D) a second amplifier of LγPNA having an N-terminal end and a C-terminal end, comprising, in an N-terminal to C-terminal direction, a first section having nucleobase sequence c'), a second section having nucleobase sequence b'), a third section having nucleobase sequence a') and a fourth section having nucleobase sequence b), wherein sequences of c and c' do not hybridize to sequences a, a', b or b'. The S strand in embodiments and aspects of the methods, composition and kit provided herein, is able to hybridize to nucleic acids, such as RNA and DNA, which comprise a right-handed helical structure. They also are able to hybridize to nucleic acid analogs, as described herein, such as RγPNA, and not to LγPNA, and therefore at least for the S strand, or at least for a portion of the S strand comprising sequences b', a', n', and o', the nucleic acid analog is not LγPNA. The phrase "able to hybridize to RγPNA and nucleic acid" does not imply that the S strand must hybridize to both RγPNA and nucleic acid concurrently.

The in situ method involves adding the reagents to a cell or tissue sample. The method of identifying a target nucleic acid in a sample comprising nucleic acids involves mixing the sample with the reagents. The method of amplifying a target nucleic acid sequence involves contacting a target nucleic acid with the reagents. All three methods include a detection step for detecting the production of the displaced LγPNA, as disclosed herein, for example by a hybridization chain reaction. Nucleic acid, biological sample and in situ cell and tissue preparation methods are extremely well-known and need not be disclosed herein to fully understand the disclosed invention.

In another aspect of the disclosure a composition is provided for use in detecting a nucleic acid. The composition comprises, referencing FIGS. 20-26, and Example 4: (A) a sensor comprising: (i) a protecting (P) strand of achiral peptide nucleic acid and/or right-handed gamma-peptide nucleic acid (RγPNA) having an N-terminal end and a C-terminal end, comprising, in an N-terminal to C-terminal direction, a first section having nucleobase sequence n, second section having nucleobase sequence m comprising unnatural nucleobases, third section having nucleobase sequence a and fourth section having nucleobase sequence b and comprising an N-terminal cysteine, sulfhydryl or protected sulthydryl group, and a thioester bond linking sections m and n; and (ii) a sensing (S) strand of RγPNA, achiral peptide nucleic acid (achiral PNA), or a nucleic acid analog able to hybridize to RγPNA and nucleic acid, having an N-terminal end and a C-terminal end, hybridized to the P strand, comprising, in an N-terminal to C-terminal direction a first section having nucleobase sequence b' complementary to sequence b, a second section having nucleobase sequence a' complementary to sequence a, a third section having nucleobase sequence n' complementary to sequence n and a fourth, toe-hold section having nucleobase sequence o', the S strand having a sequence complementary to a nucleotide sequence of a nucleic acid and comprising the target sequence, having a 5' end and a 3' end, comprising, in a 5' to 3' direction, without intervening nucleobases a first section having nucleobase sequence O complementary to sequence o', a second section having nucleobase sequence N complementary to sequence n', a third section having nucleobase sequence A complementary to sequence a' and a fourth section having nucleobase sequence B complementary to sequence b', wherein hybridization of the target nucleic acid to the S strand displaces the P strand, and the first section of the displaced P strand having nucleobase sequence n is removed by self-splicing; and (B) a converter comprising: (i) an achiral peptide nucleic acid (achiral PNA) having an N-terminal end and a C-terminal end, comprising, in an N-terminal to C-terminal direction, a first section having nucleobase sequence b' complementary to sequence b, a second section having nucleobase sequence a' complementary to sequence a, and a third section having nucleobase sequence m' having unnatural nucleobases complementary to sequence m; and (ii) a left-handed γPNA (LγPNA) having an N-terminal end and a C-terminal end, hybridized to the achiral PNA, comprising, in an N-terminal to C-terminal direction a first section having nucleobase sequence b complementary to sequence b' of the PNA, and a second section having nucleobase sequence a' complementary to sequence a of the PNA, wherein the displaced P strand hybridizes to the achiral PNA of the converter, displacing the LγPNA from the converter; and wherein, other than where sequences are indicated as being complementary, the sequences A, a, a', B, b, b', N, n, n', O, o', m or m' are not complementary to each other. The composition optionally comprises: (C) a first amplifier of LγPNA having an N-terminal end and a C-terminal end, comprising, in an N-terminal to C-terminal direction, a first section having nucleobase sequence b, a second section having nucleobase sequence c, a third section having nucleobase sequence b' and a fourth section having nucleobase sequence a'; and (D) a second amplifier of LγPNA having an N-terminal end and a C-terminal end, comprising, in an N-terminal to C-terminal direction, a first section having nucleobase sequence c'), a second section having nucleobase sequence b'), a third section having nucleobase sequence a') and a fourth section having nucleobase sequence b), wherein sequences of c and c' do not hybridize to sequences a, a', b or b'.

According to yet another aspect, the composition is provided in a kit, which comprises the composition in a vessel, such as an Eppendorf tube, multi-well plate, array, etc., in packaging, such as a box, foil pack, plastic bag, envelope, etc. acceptable for shipping. The vessel may form part of or consist of a cartridge, such as a disposable for use in an automated system for conducting assays, involving suitable robotics, fluidics, optics, etc., as are broadly available commercially for processing biological samples, for example by mixing liquids and measuring a reaction, e.g., by fluorescence detection.

According to one aspect of the invention, an analyte is detected by a hybridization chain reaction. A hybridization chain reaction, in a simpler form from the reaction described herein, is described for example and without limitation in U.S. Patent Publication No. 2005/02606351 A1, describing use of metastable nucleic acid hairpin monomers that are used in pairs or in combination of two or more hairpin structures. Although the structure of the metastable nucleic acid hairpin monomers is described in the context of nucleic acids and to some limited extent peptide nucleic acids, the overall sequence structure and logic of the formation of a detection of concatamerized products of the described monomers is equally applicable to the LγPNA amplifiers described herein, which are analogous to the monomers of that publication. The monomers described in U.S. 2005/0260635 are described as being metastable because in the absence of the initiator, they are kinetically disfavored from associating with other monomer(s), but in the presence of the initiator, the monomers form a nicked double helix. Likewise, the LγPNA amplifiers described herein do not concatamerize in the absence of the initiator—the LγPNA from the converter.

Identification of the concatamerization of the described LγPNA hairpin amplifiers by hybridization chain reaction, or identification of the presence of a target sequence in a nucleic acid by any method described herein can be accomplished by a variety of methods. The products can be identified, for example by gel electrophoresis, spectrometer, rheological methods, colorimetric methods, FRET methods, fluorescent dequenching methods (e.g., molecular beacon), fluorescent activation, enzyme-linked immunosorbent assay (ELISA), tyramide signal amplification (TSA), etc. See, generally, Marras, SAE, "Selection of Fluorophore and Quencher Pairs for Fluorescent Nucleic Acid Hybridization Probes," *Methods in Molecular Biology* 335:3-16 (2006). As shown in the Example below, a FRET pair may be used, with the donor being located on the first amplifier and the acceptor being located on the second amplifier, such that only when the first and second amplifiers concatamerize, the acceptor will fluoresce when the donor is excited. Thus, as is broadly known in the arts, the donor has an excitation spectrum in a shorter wavelength than the excitation spectrum of the acceptor (they overlap insignificantly, and preferably not at all), the donor has an emission spectrum that significantly overlaps (typically >50%) with the excitation spectrum of the acceptor, and the acceptor emission spectrum is discernable from the emission spectrum, and preferably does not overlap. The donor typically has a high extinction coefficient and a high quantum yield. FRET typically works when the effective distance between donor and acceptor is between 10 Å and 100 Å. As such one of ordinary skill can select adequate FRET pairs from the multitude of chromophores available commercially. A non-limiting list of examples of common FRET donor/acceptor pairs include: fluorescein isothiocyanate/tetramethylrhodamine isothiocyanate; Cy3/Cy5; Enhanced Green Fluorescent Protein (EGFP)/Cy3; cyan fluorescent protein/yellow fluorescent protein (YFP); and EGFP/YFP.

In another aspect, excimer formation may be used to detect concatamerization, as in the assay described in the Example below. An excimer is a composition that either does not fluoresce or that fluoresces at a different wavelength when in proximity with another molecule, which may be the same molecule. In the Example below, the emission spectrum of pyrene monomer is shown to shift~100 nm when dimerized.

Another method by which concatamerization may be detected is by fluorescent dequenching. In one example, molecular beacon technology can be utilized, as is broadly-known in the arts. In this example, the amplifiers comprise both a fluorophore and a quencher of the fluorophore that only quenches the fluorophore when the amplifier is in its hairpin configuration. The fluorophore and quencher are located on the amplifier such that when the hairpin is opened, and the amplifiers are concatamerized, the quencher no longer quenches the fluorescence of the fluorophore. In an alternate embodiment, the quencher is located on one amplifier and the fluorophore is located on the other, and are positioned such that when not concatamerized, the fluorophore fluoresces, and when concatamerized, the fluorophore is quenched. Another version of fluorescent dequenching is described in, for example, Pianowski, Z, et al., Imaging of mRNA in Live Cells Using Nucleic Acid-Templated Reduction of Azidorhodamine Probes, *J. Am. Chem. Soc.* 131: 6492-6497 (2009), in which a profluorescent, chemically modified fluorophore, is modified by an activator on the other strand to produce a fluorescent moiety. In the specific example provided in that article, profluorescent azidorhodamine is attached to a first strand, and is "unmasked" by hybridization to a nucleic acid strand having a pendant alkylphosphine. As described in Pianowski, Z, et al., azido-coumarin dyes also may be "unmasked" by an alkyl phosphine.

In a further aspect of detection of the concatamerization, fluorescence activation may be used, in which a portion of a fluorophore is located on each strand, with each portion being non-fluorescent or less fluorescent at a detection excitation and/or emission wavelength, and which, when placed in proximity, the portions covalently link and form a fluorochrome that fluoresces at the detection excitation and emission wavelengths. A non-limiting example of this is the Cu(I)-mediated click-chemistry linking of azide and alkyne moities described in Sivakumar, K, et al., A Fluorogenic 1,3-Dipolar Cycloaddition Reaction of 3-Azidocoumarins and Acetylenes, *Organic Letters*, 6(24):4603-4606 (2004), in which 3-azido-coumarin and acetylene- (ethyne-) substituted phenyl or substituted phenyl profluorophores are linked in the presence of Cu(I) (e.g., CuSO$_4$) to form a fluorphore. In the context of the compositions described herein, and for example in the I-NADSA reaction described below, the 3-azidocoumarin profluorophore is linked to one amplifier, and the acetylene-substituted phenyl profluorophore is linked to the other amplifier, and are located such that when Cu(I) is added to the reaction, typically after addition of a nucleic acid sample to be analyzed (e.g., 30 seconds, 1, 2, 3, 4, 5, 10, or 15 minutes or increments therebetween), profluorophore combinations (that is, the 3-azidocoumarin and the acetylene-substituted phenyl moieties) present in the concatamerized product, will link covalently to form a triazolylcoumarin fluorophore. Examples of suitable azide and alkyne building blocks (profluorophores) useful in any combination and which are useful for detection of concatamerization of the amplifiers in the described I-NADSA reaction described herein, are provided in FIG. 2 of Sivakumar, K, et al., for example, as follows, with profluorophores (8) and (9) combining in the presence of Cu(I) to form (10)

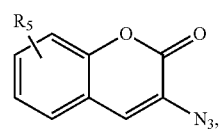

(8)

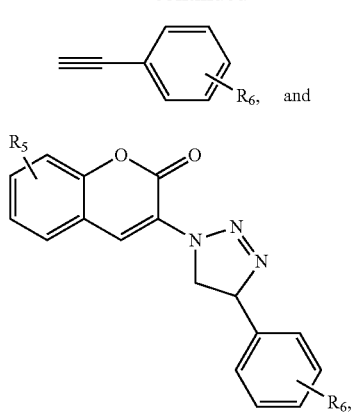

(9)

(10)

where R5 is H, (C$_1$-C$_6$) alkyl, phenyl, (C$_1$-C$_6$) alkoxyl, halo-substituted (C$_1$-C$_6$) alkyl, (C$_1$-C$_6$) alkyl ester, e.g., Cl, I, F, or Br, and R6 is H, halo, (C$_1$-C$_6$) alkyl, (C$_1$-C$_6$) alkoxyl, halo-substituted (C$_1$-C$_6$) alkyl, halo-substituted (C$_1$-C$_6$) alkyl, or amine.

In another aspect, as indicated in FIG. 1, a PNA or PNA/Nucleic acid structure is provided. As indicated in FIG. 1, RγPNA, achiral PNA, RNA and DNA can hybridize together in any combination. Likewise, LγPNA and achiral PNA can hybridize together. Thus, structures can be produced comprising any compatible combination of these nucleic acids and nucleic acid analogs according to those rules, based on complementarity of a sequence of at least 3 nucleobases. Nucleic acids and PNAs are not only useful for biological purposes, but are capable of use in the preparation of nano-assemblies (see, e.g., Jones et al., "Programmable materials and the nature of the DNA bond", *Science* 347, 1260901 (Feb. 20, 2015). DOI: 10.1126/science.1260901; Pinhiero, A V, et al., "Challenges and Opportunities for Structural DNA Nanotechnology" *Nature Nanotechnology* (Nov. 6, 2011). DOI: 10.1038/NNANO.2011.187; and Zhang, D Y, et al. "Dynamic DNA Nanotechnology Using Strand Displacement Reactions" *Nature Chemistry* (Jan. 24, 2011). DOI: 10.1038/nchem.957). In one aspect a structure is provided comprising an LγPNA hybridized to an achiral PNA is provided. In another aspect, a structure is provided comprising an achiral PNA hybridized to both an LγPNA and one of a DNA, an RNA, a nucleic acid analog or a RγPNA. As with standard Watson-Crick binding, the hybridization in any of these embodiments is due to the presence of complementary nucleobase sequences in the hybridizing compositions, and the nucleobases can be natural or unnatural.

Figure 3:
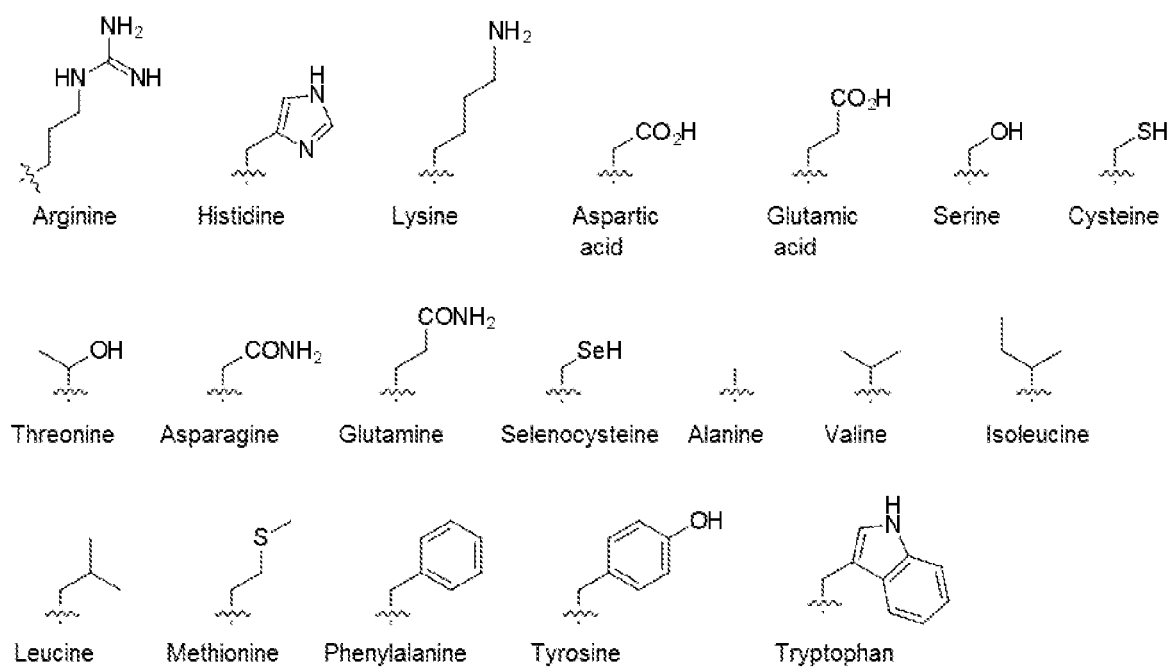
FIG. 3 provides examples of amino acid side chains.

As used herein, an "amino acid side chain" is a side chain for an amino acid. Amino acids have the structure:

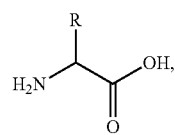

where R is the amino acid side chain. Non-limiting examples of amino acid side chains are shown in FIG. 3. Glycine is not represented because in the embodiment R1 and R2 are both H.

"Alkyl" refers to straight, branched chain, or cyclic hydrocarbon groups including from 1 to about 20 carbon atoms, for example and without limitation C$_{1-3}$, C$_{1-6}$, C$_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—CH$_2$—CH$_2$—). "Optionally substituted alkylene" refers to alkylene or substituted alkylene.

"Alkene or alkenyl" refers to straight, branched chain, or cyclic hydrocarbyl groups including from 2 to about 20 carbon atoms, such as, without limitation C$_{1-3}$, C$_{1-6}$, C$_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. "Optionally substituted alkene" refers to alkene or substituted alkene. Likewise, "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a (C$_1$-C$_6$)alkoxy group includes —O-methyl (methoxy), —O-ethyl (ethoxy), —O-propyl (propoxy), —O— isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a (C$_1$-C$_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "ether" or "oxygen ether" refers to an alkyl group, such as a (C$_1$-C$_{10}$)alkyl group wherein one or more of the alkyl group's carbon atoms is replaced with an —O— group. An example of an ether is a poly(alkylene oxide), also referred to as a poly(alkylene glycol) or polyglycols, such as a poly($C_1$-$C_{10}$) alkylene oxide), such as poly(ethylene glycol) (PEG), poly(propylene glycol) (PPG), poly(butylene glycol) (PBG), etc., and include two or more monomer residues, for example in one aspect, from 2-50 monomer residues. The term ether includes —$CH_2$—(O$CH_2$—$CH_2$)$_q$ O$P_1$ compounds where P1 is a protecting group, —H, or a ($C_1$-$C_{10}$)alkyl. Exemplary ethers include polyethylene glycol, diethylether, methylhexyl ether, PEG-PPG-PEG or PPG-PEG-PPG block copolymers, etc.

The term "thioether" refers to ($C_1$-$C_{10}$)alkyl group wherein one or more of the alkyl group's carbon atoms is replaced with an —S— group. The term thioether includes —$CH_2$—(S$CH_2$—$CH_2$)$_q$—S$P_1$ compounds where P1 is a protecting group, —H, or a ($C_1$-$C_{10}$)alkyl. Exemplary thioethers include dimethylthioether, ethylmethyl thioether. Protecting groups are known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), dimethoxytrityl (DMT), 1-(4,4-dimethyl-2,6-dioxacyclohexylidene)ethyl (Dde), diathiasuccinoyl (Dts), benzothiazole-2-sulfonyl (Bts) and monomethoxytrityl (MMT) groups.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound, wherein the substituents are as described herein.

"Carboxyl" or "carboxylic" refers to group having the indicated number of carbon atoms and terminating in a —C(O)OH group, thus having the structure —R—C(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"($C_3$-$C_8$)aryl-($C_1$-$C_6$)alkylene" refers to a divalent alkylene wherein one or more hydrogen atoms in the $C_1$-$C_6$ alkylene group is replaced by a ($C_3$-$C_8$)aryl group. Examples of ($C_3$-$C_8$)aryl-($C_1$-$C_6$)alkylene groups include without limitation 1-phenylbutylene, phenyl-2-butylene, 1-phenyl-2-methylpropylene, phenylmethylene, phenylpropylene, and naphthylethylene. The term "($C_3$-$C_8$)cycloalkyl-($C_1$-$C_6$)alkylene" refers to a divalent alkylene wherein one or more hydrogen atoms in the $C_1$-$C_6$ alkylene group is replaced by a ($C_3$-$C_8$)cycloalkyl group. Examples of ($C_3$-$C_8$)cycloalkyl-($C_1$-$C_6$)alkylene groups include without limitation 1-cycloproylbutylene, cyclproyl-2-butylene, cyclopentyl-1-phenyl-2-methylpropylene, cyclobutylmethylene and cyclohexylpropylene.

A polymer is a homopolymer or copolymer prepared from monomers, which, when incorporated into the polymer are "residues." Polymers may have a variety of topologies, such as linear, branched, circular, comb, star, etc. Polymers include block copolymers.

Unless otherwise indicated, the nucleic acids and nucleic acid analogs described herein are not described with respect to any particular sequence of bases. The present disclosure is directed to generally and broadly-applicable methods and compositions, and the usefulness of any specific embodiments described herein, while depending upon a specific sequence in each instance, is generically and broadly applicable to any particular sequence of nucleobases and sequences complementary thereto. Based on the abundance of published work with nucleic acids, nucleic acid analogs and PNA (e.g., γPNA), it is expected that any nucleobase sequence attached to the backbone of the described γPNA oligomers would hybridize in an expected, specific manner with a complementary nucleobase sequence of a target nucleic acid or nucleic acid analog by Watson-Crick or Watson-Crick-like hydrogen bonding. One of ordinary skill would understand that the compositions and methods described herein are sequence-independent.

The nucleic acids, nucleic acid analogs, and PNAs described herein comprise a backbone and at least two nucleobases. This structure is shown schematically in Formula 3:

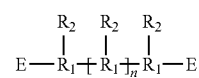

(3)

where R1 is a backbone monomer residue and R2s are, independently nucleobases. E are independently end (terminal) groups that are part of the terminal monomer residues, and "n" is any positive integer or 0. Typically, all instances of R1 are the same with the exception of the terminal monomer residues which typically have different end-groups E as compared to internal monomers, such as, without limitation $NH_2$ and C(O)OH or $CONH_2$ at the respective N-terminal and C-terminal ends for PNAs, and hydroxyl groups at the 5' and 3' ends of nucleic acids. An exception to this is the P-strand described herein as having a terminal sulthydryl or protected sulthydryl, and an internal thioester bond.

In one aspect of the present invention, reagents, such as the nucleic acids, nucleic acid analogs, and/or PNAs are implemented as a solution-phase assay, that is, as in Example 4, all reagents are present in solution, with no reagent being bound to a surface, as in an array, below.

In one aspect of the present invention, reagents, such as the nucleic acids, nucleic acid analogs, and/or PNAs are implemented on a substrate or an array. Arrays are particularly useful in implementing high-throughput assays, such as genetic detection assays. As used herein, the term "array"

refers to reagents, for example the PNA reagents described herein, located at two or more discrete, identifiable and/or addressable locations on a substrate. In one embodiment, an array is an apparatus having two or more discrete, identifiable reaction chambers, such as, without limitation a 96-well dish, in which reactions comprising identified constituents are performed. In an exemplary embodiment, two or more reagents described herein are immobilized onto a substrate in a spatially addressable manner so that each individual set of PNAs, e.g., the sensor, converter and amplifiers are located at a different and identifiable (addressable) location on the substrate. Substrates include, without limitation, multi-well plates, silicon chips and beads. In one embodiment, the array comprises two or more sets of beads, with each bead set having an identifiable marker, such as a quantum dot or fluorescent tag, so that the beads are individually identifiable using, for example and without limitation, a flow cytometer. In one embodiment, an array is a multi-well plate containing two or more wells with the described reagents for amplifying specific sequences. As such, reagents, such as one or more of the sensor, converter and amplifiers may be bound or otherwise deposited onto or into specific locations on an array. Reagents may be in any suitable form, including, without limitation: in solution, dried, lyophilized or glassified. When linked covalently to a substrate, such as an agarose bead or silicon chip, a variety of linking technologies are known for attaching chemical moieties, such as the PNA compositions described herein, to such substrates. Linkers and spacers for use in linking nucleic acids, peptide nucleic acids and other nucleic acid analogs are broadly known in the chemical and array arts and for that reason are not described herein. As a non-limiting example, a γPNA reagent contains a reactive amine, which can be reacted with carboxyl, cyanogen bromide-, N-hydroxysuccinimide ester-, carbonyldiimidazole- or aldehyde-functional agarose beads, available, for instance from Thermo Fisher Scientific (Pierce Protein Biology Products), Rockford, Ill. and a variety of other sources. The reagents described herein can be attached to a substrate in any manner, with or without linkers. In one aspect, the LγPNA strand of the converter is linked to the substrate. Informatics and/or statistical software or other computer-implemented processes for analyzing array data and/or identifying genetic risk factors from data obtained from a patient sample, are known in the art. In a further, non-arrayed embodiment, reagents, e.g., PNAs for carrying out only one specific assay, are contained within a single vessel or well, with, e.g., the γPNA of the converter strand, is linked to the substrate/vessel/tube/well.

The reactions described herein can be efficiently multiplexed, so long as the sequences do not cross-react and the detection method can differentiate the products of the different reactions, e.g., by employing different fluorochromes, such that the excitation and/or emission wavelengths of the signal for detection of the concatenated product are different.

By "immobilized" in reference to a composition such as a nucleic acid, nucleic acid analog, or PNA as described herein, it is meant attached to a substrate of any physical structure or chemical composition. The immobilized composition is immobilized by any method useful in the context of the end use. The composition is immobilized by covalent or non-covalent methods, such as by covalent linkage of amine groups to a linker or spacer, or by non-covalent bonding, including Van derWaals and/or hydrogen bonding. A "label" is a chemical moiety that is useful in detection of, or purification or a molecule or composition comprising the label. A label may be, for example and without limitation, a radioactive moiety, such as $^{14}C$, $^{32}P$, $^{35}S$, a fluorescent dye, such as fluorescein isothiocyanate or a cyanine dye, an enzyme, or a ligand for binding other compounds such as biotin for binding streptavidin, or an epitope for binding an antibody. A multitude of such labels, and methods of use thereof are known to those of ordinary skill in the immunology and molecular biology arts.

In another aspect of the present disclosure, a method of preparing optically pure LγPNA and RγPNA monomers are provided. The method is a distinct improvement over current methods, and substantially increases the commercial viability of use of chiral γPNAs. As such a method for preparing a chiral γPNA monomer is provided. Further to Example 2, the method comprises first preparing a dibenzylated intermediate by dibenzylating the amino group of L-serine; protecting the hydroxyl group of the side chain of the L-serine; and reducing the carboxylic acid group of the L-serine to obtain a dibenzylated intermediate having a protected hydroxyl group. The dibenzylated intermediate can then be used to prepare either left-handed or right-handed γPNA monomers. To prepare right-handed γPNA monomers, the method comprises: mesylating, and azidatizing the dibenzylated intermediate and deprotecting the protected hydroxyl group of the dibenzylated intermediate to obtain an azidated intermediate having an azido group and a hydroxyl group; alkylating the hydroxyl group and reducing the azido group of the azidated intermediate to obtain a primary amine intermediate; coupling the primary amine intermediate with benzyl glyoxylate to obtain a backbone intermediate having a protected primary amino group and a benzyloxy carbonyl group; deprotecting the protected primary amino group and the benzyloxy carbonyl group of the backbone intermediate and selectively protecting the backbone intermediate with a protecting group to obtain a protected backbone intermediate; and coupling the protected backbone intermediate with a nucleobase. To prepare left-handed γPNA monomer the method comprises: alkylating the hydroxyl group of the dibenzylated intermediate and deprotecting the protected hydroxyl group of the dibenzylated intermediate to obtain an alkoxy intermediate; mesylating and azidatizing the alkoxy intermediate to obtain an azidated intermediate having an azido group; reducing the azido group of the azidated intermediate to obtain a primary amine intermediate; coupling the primary amine intermediate with benzyl glyoxylate to obtain a backbone intermediate having a protected primary amino group and a benzyloxy carbonyl group; deprotecting the protected primary amino group and the benzyloxy carbonyl group of the backbone intermediate and selectively protecting the backbone intermediate with a protecting group to obtain a protected backbone intermediate; and coupling the protected backbone intermediate with a nucleobase. The nucleobase can be any suitable nucleobase, for example and without limitation, nucleobases are independently selected from the group consisting of A, G, C, T, U, unnatural nucleobases or divalent nucleobases. In one aspect, the prepared chiral γPNA monomer is optically pure. Any protecting group can substitute for the specifically-listed protecting groups. As indicated above, non-limiting examples of protecting groups include: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), dimethoxytrityl (DMT), 1-(4,4-dimethyl-2,6-dioxacyclohexylidene)ethyl (Dde), diathiasuccinoyl (Dts), benzothiazole-2-sulfonyl (Bts) and monomethoxytrityl (MMT) groups. In one aspect the protecting group for the amine of the γPNA monomer produced by these methods is Fmoc.

PNAs, such as PNA oligomers or polymers, including achiral PNA, RγPNA LγPNA, and oligomers or polymers combining PNA, RγPNA and/or LγPNA monomers are prepared from monomers thereof by, e.g., standard peptide synthesis methodologies, for example by solid-phase methods as are broadly-known in the art, involving attaching a peptide to a solid-phase support, followed by repeated cycles of deprotection, washing, coupling and washing for the addition of each specific PNA monomer. Peptide/PNA synthesis methods and services are commercially available, e.g., from Panagene of Daejeon, Korea.

Example 1

Synthesis of LγPNA Monomers from D-Amino Acids

Figure 4:
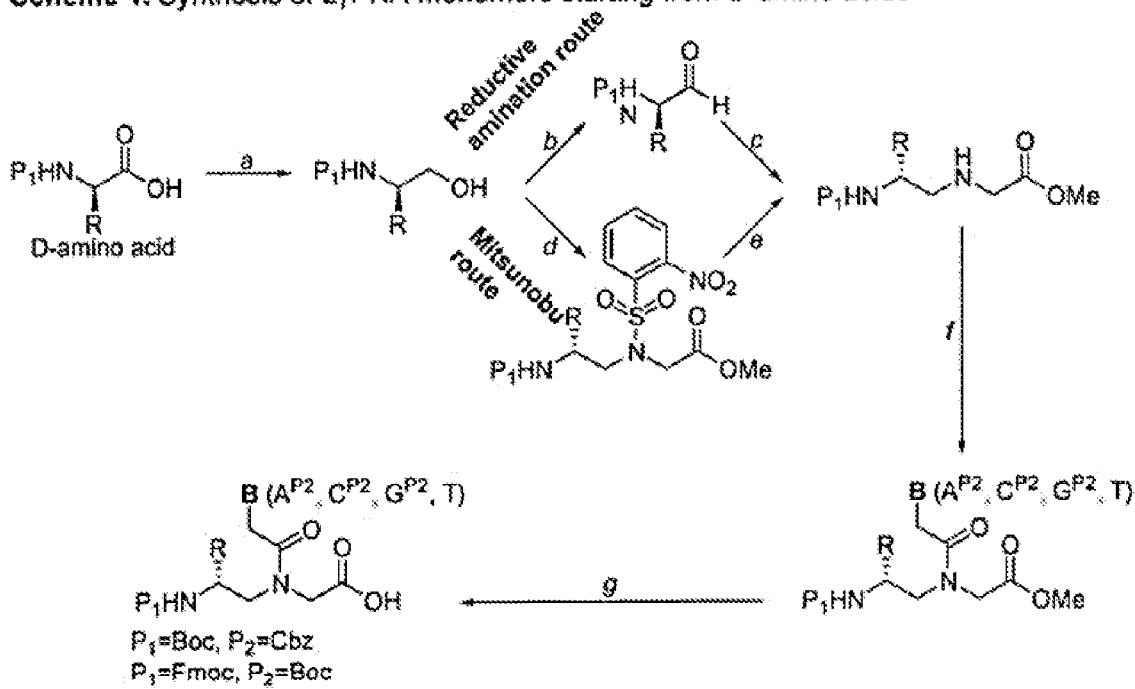
FIG. 4 provides reaction scheme 1 of Example 1.

LγPNA are synthesized from D-amino acids via reductive amination synthesis or a Mitsunobu reaction, according to the reagents and conditions detailed in Scheme 1, FIG. 4.

Reagents and conditions: (a) NMM (N-methylmorpholine), IBC (isobutyl chloroformate), DME 4° C., the $NaBH_4$; (b) Swern oxidation; (c) methyl glycine ester, NMM 4° C., then AcOH (acetic acid), $NaBH_3CN$; (d) Mitsonobu reaction; (e) $CsCO_3$, thiophenol, THF (tetrahydrofuran), room temperature; (f) HBTU (2-(1H-benzotriazol-1-yl)-1,1,3,3-tetramethyluronium hexafluorophosphate), nucleobase, DMF (dimethylformamide), room temperature; (g) 2N NaOH/THF. The nucleobase of step (f) can be any nucleobase, including natural or unnatural nucleobases described herein or elsewhere, for example and without limitation, the divalent nucleobases of WO 2014/169206.

Example 2

Synthesis of (A) RγPNA and (B) LγPNA Monomers from L-Serine

Figure 5:
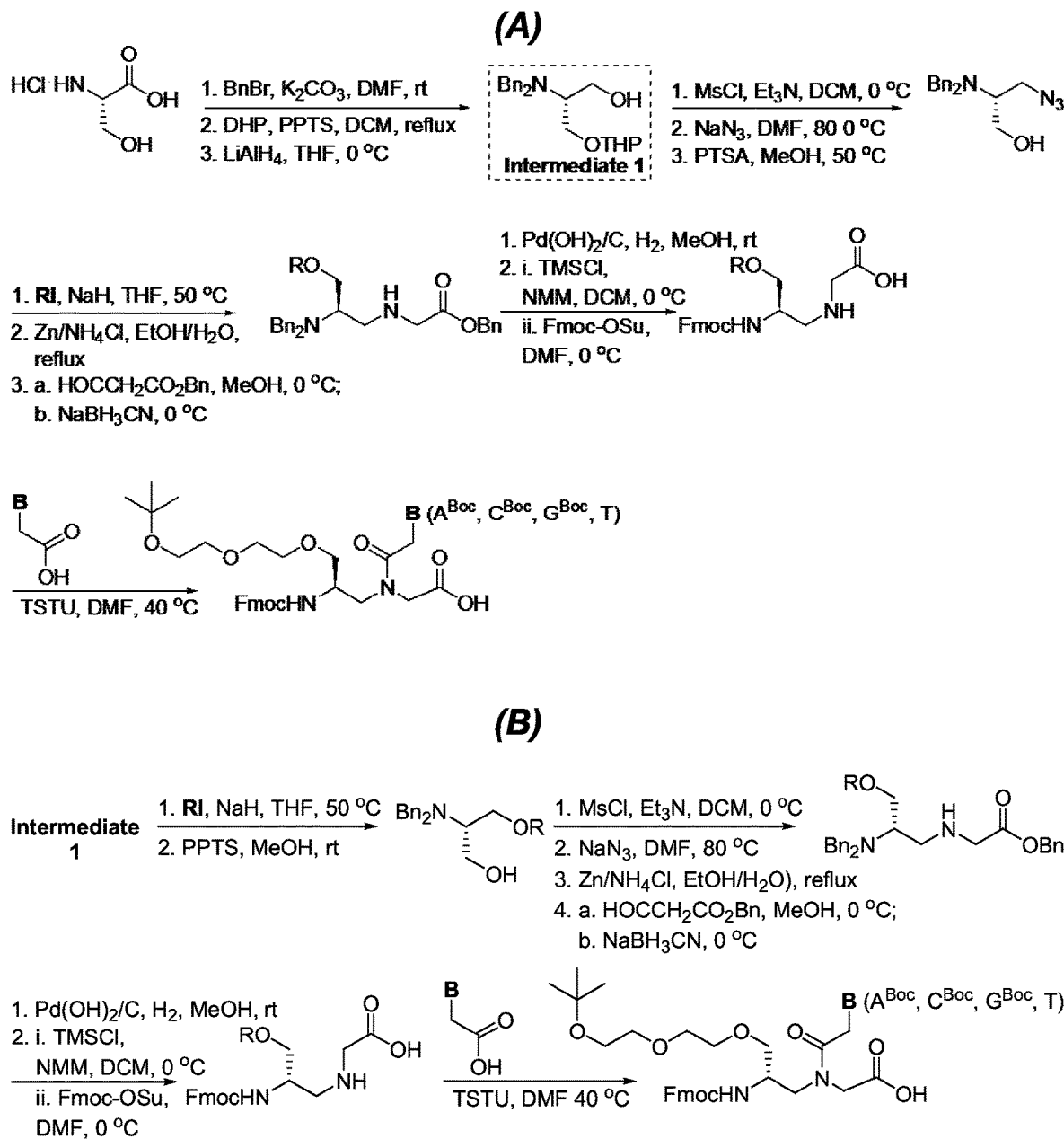
FIG. 5 provides reaction scheme 2 of Example 2.

Both LγPNA and RγPNA monomers are synthesized from L-serine. The reagents and conditions for this synthesis of RγPNA and LγPNA are detailed below in Scheme 2 (FIG. 5), (A) and (B), respectively. Although synthesis is described in the context of natural nucleobases A, G, C and T, the method is equally applicable to other nucleobases, for example the natural or unnatural nucleobases described herein or elsewhere, for example and without limitation, the divalent nucleobases of WO 2014/169206. The major advantages of this synthetic scheme are optical purity, scalability, cost-saving, and ease of functional group modifications at the γ-backbone. The synthesis described herein is typically performed on a 100 g-scale. The first step involves dibenzylation of the amino group of L-serine, a commercially available and relatively cheap starting material. Selective protection of the serine sidechain with tetrahydropyran (THP) by refluxing the dibenzylated L-serine product with 3,4-dihydropyran (3,4-DHP) and pyridinium p-toluenesulfonate (PPTS) in methanol, followed by reduction with lithium aluminum hydride yields the monoalcohol Intermediate 1. Mesylation, followed by azidation and removal of the THP group with p-toluenesulfonic acid (PTSA) at reflux affords the free alcohol. Alkylation allows selective a functional group to be introduced at the γ-backbone. Reduction of the azido group with Zn/ammnonium chloride in EtOH/ $H_2O$ under reflux condition gives the primary amine. Coupling of the amine group with benzyl glyoxylate, followed by reduction with sodium cyanoborohydride yields the backbone intermediate. Removal of the benzyl group (Bn), selective protection of the primary amine with Fmoc, and coupling the backbone to nucleobases yields the RγPNA monomers. Synthesis of LγPNA monomers follows a similar series of steps, starting from Intermediate 1.

Example 3

Figure 6:
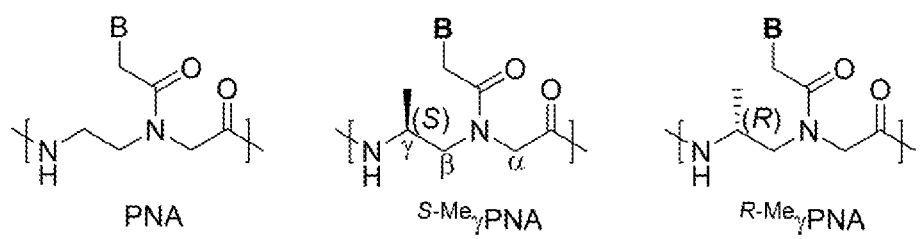
FIG. 6 provides chemical structures of PNA and γPNA units with R1 being methyl and B representing the nucleobase.

Herein we report the development of a tight-binding, orthogonal, synthetically versatile and information-interfaced nucleic acid platform, called gamma-peptide nucleic acid (γPNA), for programming molecular interactions. The system comprises three molecular entities: the right-handed (RH) and left-handed (LH) helical conformers and a non-helical (NH) domain, with the first two incapable of recognizing each other, and the third capable of recognizing the RH and LH conformers, as well as the natural nucleic acid biopolymers (i.e. DNA and RNA)—enabling the storage and translation of genetic information from one system to the next. All three domains are prepared from the same chemical building blocks, with the exception of the stereochemistry or lack thereof at the γ-backbone that determines if the corresponding oligo adopts an RH, LH or NH motif (FIG. 6). The work has direct implications for in vitro as well as in vivo molecular self-assembly and computing.

Experimental Procedures

Monomer synthesis.

Figure 7:
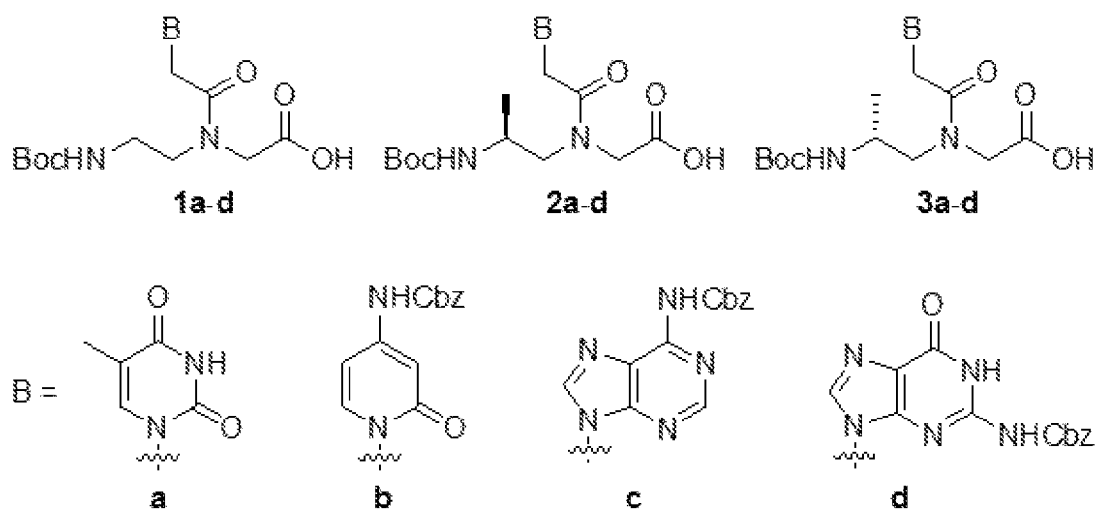
FIG. 7 provides chemical structures of NH-PNA (1a-d), RH-γPNA (2a-d) and LH-γPNA (3a-d) chemical building blocks.

PNA monomers (1a-d, FIG. 7) were prepared according the procedures reported by Duehol et al. ("Synthesis of peptide nucleic acid monomers containing the four natural nucleobases: Thymine, cytosine, adenine, and guanine and their oligomerization," J. Org. Chem. 1994, 59, 5767-5773), and RH- (2a-d, FIG. 7) and LH-γPNA (3a-d, FIG. 7) building blocks were synthesized using the Mitsunobu route according to the procedures reported by Manna et al. ("Synthesis of optically pure γPNA monomers: a comparative study," Tetrahedron 2015, 71, 3507-3514), starting with Boc-L-Ala and Boc-D-Ala, respectively (See e.g., Schemes 1 and 2, FIGS. 4 and 5).

Solid-Phase Oligomer Synthesis.

PNA and γPNA oligos (Table 3) were synthesized manually on MBHA resin using the standard Boc-solid-phase peptide synthesis procedure. (Dragulescu-Andrasi, et al., "A simple γ-backbone modification preorganizes peptide nucleic acid into a helical structure." J. Am. Chem. Soc. 2006, 128(31):10258-10267). The resulting products were cleaved from the resin and purified by reverse-phase HPLC and characterized by MALDI-TOF. Below are the expected masses of the oligos and those that were found (Table 4).

TABLE 3

Sequence of PNA and γPNA oligos

| PNA | Sequence | γ-ConFigure | Hel. sense |
|---|---|---|---|
| 1 | H-$^L$Lys-CCAAC-$^L$Lys-$NH_2$ | Achiral | NH |
| 2 | H-$^L$Lys-GTTGG-$^L$Lys-$NH_2$ | Achiral | NH |
| 3 | H-$^L$Lys-CCAAC-$^L$Lys-$NH_2$ | S (L) | RH |
| 4 | H-$^L$Lys-GTTGG-$^L$Lys-$NH_2$ | S (L) | RH |
| 5 | H-$^L$Lys-CCAAC-$^L$Lys-$NH_2$ | R (D) | LH |
| 6 | H-$^L$Lys-GTTGG-$^L$Lys-$NH_2$ | R (D) | LH |

TABLE 3-continued

Sequence of PNA and γPNA oligos

| PNA | Sequence | γ-ConFigure | Hel. sense |
|---|---|---|---|
| 7 | H-$^L$Lys-CCGAC-$^L$Lys-NH$_2$ | R (D) | LH |
| 8 | H-$^L$Lys-CCCAC-$^L$Lys-NH$_2$ | R (D) | LH |
| 9 | H-$^L$Lys-CCTAC-$^L$Lys-NH$_2$ | R (D) | LH |

Bold indicates chiral γ-Me PNA unit. L and D indicate the stereochemical configurations of the amino acid (alanine) from which these chemical building blocks were prepared. NH: non-helical, RH: right-hand, LH: left-hand.

TABLE 4

| Oligomer | Mass calculated | Mass found |
|---|---|---|
| PNA1 | 1578.64 | 1575.47 |
| PNA2 | 1680.69 | 1677.61 |
| PNA3 | 1649.78 | 1647.47 |
| PNA4 | 1750.82 | 1749.56 |
| PNA5 | 1649.78 | 1646.06 |
| PNA6 | 1750.82 | 1747.64 |
| PNA7 | 1664.77 | 1660.71 |
| PNA8 | 1624.75 | 1621.26 |
| PNA9 | 1639.76 | 1635.99 |
| PNA3P | 2006.20 | 2004.48 |
| PNA4P | 2108.24 | 2106.52 |
| PNA5P | 2006.20 | 2001.26 |
| PNA6P | 2108.24 | 2103.60 |
| PNA3C | 3636.91 | 3639.78 |
| PNA4T | 3885.12 | 3887.67 |
| PNA5T | 3783.07 | 3788.84 |
| PNA6C | 3738.95 | 3742.64 |

CD Measurements.

The samples were prepared in phosphate buffer (10 mM sodium phosphate, 0.1 mM EDTA, 100 mM NaCl, pH=7.2), heated to 90° C. for 5 min and allowed to cool to room temperature overnight. CD experiments were performed on a JASCO J-715 spectropolarimeter using a quartz cuvette with a 1-cm path length. The samples were scanned from 320 to 200 nm at the rate of 100 nm/min and for a total of 15 scans for each run. All spectra were smoothed using five-point adjacent averaging and the baseline (buffer) spectrum was subtracted using Origin software.

UV-Melting Experiments.

The samples were prepared in phosphate buffer (10 mM sodium phosphate, 0.1 mM EDTA, 100 mM NaCl, pH=7.2). Both the heating and cooling runs were performed. UV-melting curves were collected on a Varian Cary 300 Bio UV-Vis spectrometer equipped with a thermoelectrically controlled multi-cell holder. UV-absorbance was collected at 260 nm as a function of temperature from 5 to 90° C. and then from 90 to 5° C. at the rate of 1° C. per min. The $T_m$s were determined by taking first derivative of the melting curves.

Thermodynamic Analysis.

The duplexes were prepared at 2.5, 5, 10, 15, 20, and 25 μM strand concentrations each in phosphate buffer. UV-melting curves were recorded as described above, and the $T_m$s were determined by taking the first derivatives of the melting curves. A plot $\ln(C_t)$ vs. $1/T_m$ was made, where $C_t$ is the total strand concentration and $T_m$ is the melting transition in Kelvin. From the plot a line fit was made, where the slope equals $((n-1)R)/\Delta H$ (n=2 and R=8.314 J/mol K) and the y-intercept equals $(\Delta S-((n-1)*R*\ln 2n))/\Delta H$ (n=2 and R=8.314 J/mol K). AG was determined using the equation $\Delta G=\Delta H-T\Delta S$, where T=298 K (Tables 5 and 6).

TABLE 5

| Duplex | Conc. (M) | Total Conc. (M) | Temp. (° C.) | ln Conc. | 1/T (K-1) |
|---|---|---|---|---|---|
| PNA3-PNA4 | 2.50E−06 | 5.00E−06 | 50 | −12.21 | 3.10E−03 |
| PNA3-PNA4 | 5.00E−06 | 1.00E−05 | 53 | −11.51 | 3.07E−03 |
| PNA3-PNA4 | 1.00E−05 | 2.00E−05 | 57 | −10.82 | 3.03E−03 |
| PNA3-PNA4 | 1.50E−05 | 3.00E−05 | 58 | −10.41 | 3.02E−03 |
| PNA3-PNA4 | 2.00E−05 | 4.00E−05 | 59 | −10.13 | 3.01E−03 |
| PNA3-PNA4 | 2.50E−05 | 5.00E−05 | 60 | −9.90 | 3.00E−03 |
| PNA5-PNA6 | 2.50E−06 | 5.00E−06 | 50 | −12.21 | 3.10E−03 |
| PNA5-PNA6 | 5.00E−06 | 1.00E−05 | 54 | −11.51 | 3.06E−03 |
| PNA5-PNA6 | 1.00E−05 | 2.00E−05 | 56 | −10.82 | 3.04E−03 |
| PNA5-PNA6 | 1.50E−05 | 3.00E−05 | 57 | −10.41 | 3.03E−03 |
| PNA5-PNA6 | 2.00E−05 | 4.00E−05 | 58 | −10.13 | 3.02E−03 |
| PNA5-PNA6 | 2.50E−05 | 5.00E−05 | 59 | −9.90 | 3.01E−03 |

TABLE 6

| Duplex | y-Intercept | Slope |
|---|---|---|
| PNA3-PNA4 | 2.60E−03 | −4.05E−05 |
| PNA5-PNA6 | 2.67E−03 | −3.41E−05 |

Fluorescence Measurements.

The samples were prepared in phosphate buffer, heated to 90° C. for 5 min and allowed to cool to room temperature overnight. Fluorescent profiles were recorded on a Varian Cary Eclipse fluorescence spectrometer using a quartz cuvette with 1-cm path length. The samples were excited at 344 nm, and the fluorescent emissions were scanned from 360 to 600 nm. All spectra were smoothed using five-point adjacent averaging and the baseline (buffer) spectrum was subtracted using Origin software.

Polystyrene Bead Assembly.

Streptavidin-coated polystyrene microspheres were purchased from Spherotech. Since the microspheres were large, they were transferred using micropipettes whose plastic tips were cut to create a larger opening. Before the microspheres were used, they were washed. This was done by transferring 100 μL of the slurry solution to an Eppendorf tube, centrifuging the mixture and removing the top buffer layer. The microspheres were then resuspended in 300 μL of sodium phosphate buffer and vortexed. The sample was centrifuged and the top buffer layer was removed. The re-suspension, centrifuging and buffer removal (wash cycle) was repeated three times. Then 50 μL of PNA (20 μM solution) was added to the microsphere mixture and gently place on a shaker for 1.5 hrs to ensure that the biotin-containing PNA oligos were bound to the streptavidin on the microspheres' surface. The microspheres were washed five times to ensure that all unbound biotin-PNA was removed. At this point they should be pink or yellow, depending on the dye used. The microspheres were then resuspended in 400 μL of sodium phosphate buffer. This process was done to make 10-PNA4T (RH), 10-PNA6C (LH), 2-PNA3C (RH), and 2-PNA5T (LH). PNA without biotin (but with dye) was also mixed with the microspheres and then washed to determine if PNA itself was interacting with the streptavidin. In this case we did not see any color change in the microspheres, indicating that PNA bound to the microspheres occurred through biotin-streptavidin interaction.

Self-Assembly of Polystyrene Microspheres.

Various combinations of microsphere solutions were prepared and imaged in DIC and fluorescent modes using Olympus IX81 microscope at 40× magnification. Below is a representative of sample preparation. 20 μL of 10-PNA4T (RH) and 500 μL of the sodium phosphate buffer were placed in a well of the cell culture plate and allowed to settle for 30 min at room temperature, after which point 20 μL of 2-PNA3C (RH) was gently added and the mixture was placed on the countertop for 1 hr. At this point, most of the beads settled at the bottom of the well. The plate was transferred to the microscope, and DIC and fluorescent images were taken.

Results and Discussion

Rationale.

Peptide nucleic acid (PNA) has been around for more than two decades, developed by Nielsen and coworkers (Nielsen, P. E., et al., *Science* 1991, 254, 1497) in 1991 in which the natural sugar phosphodiester backbone was replaced by achiral N-(2-aminoethyl)glycine units (see, FIG. 6). PNA has many appealing features, including high binding affinity and sequence-specificity, resistance to enzymatic degradation by proteases and nucleases, and an ability to invade certain sequences of double helical DNA (Nielsen, P. E., *Acc. Chem. Res.* 1999, 32, 624). However, because of the non-ionic backbone, PNA is only moderately soluble in water and, as such, it has a tendency to aggregate and adhere to surfaces and other macromolecules in a nonspecific manner (Braasch, D. A., et al., *Methods* 2001, 23, 97 and Tackett, A. J., et al., *Nucleic Acids Res.* 2002, 30, 950). Such a property makes sample-handling and processing less of a routine. Further, like most nucleic acids, PNA is not cell-permeable (Nielsen, P. E., *Q. Rev. Biophys.* 2005, 38, 345). Such a barrier has prevented PNA from finding wide-spread applications in biology and medicine, though some progress has been made (Koppelhus, U., et al., *Antisense Nuc. Acids Drug Devel.* 2002, 12, 51; Zhou, P., et al., *J. Am. Chem. Soc.* 2003, 125, 6878; Janowski, B. A., et al., *Nat. Chem. Biol.* 2005, 1, 210; Mitra, R., et al., *J. Organic Chem.* 2012, 77, 5696; Bahal, R., et al., *Curr. Mol. Therap.* 2014, 14, 1). In the attempts to address these issues, diverse chemical modifications have been made to the structure of PNA (Beck, F., et al., In *Artificial DNA: methods and applications*; CRC Press: Boca Raton, 2003; Vol. 2003, p 91; Kumar, V. A., et al., *Acc. Chem. Res.* 2005, 38, 404; Sugiyama, T., et al., *Molecules* 2013, 18, 287). Among the most promising modification—with respect to the ease of chemical synthesis, functional group diversification and conformational pre-organization—was the installation of a chiral center at the γ-backbone (Mitra, R. et al., *J. Organic Chem.* 2012, 77, 5696; Kosynkina, L., et al., *Tetrahedron Lett.* 1994, 35, 5173; Wu, Y., et al., *Tetrahedron* 2001, 57, 8107; Falkiewicz, B., et al., *Tetrahedron* 2001, 57, 7909; Englund, E. A., et al., *Org. Lett.* 2005, 7, 3465; Tedeschi, T., et al., *Tetrahedron Lett.* 2005, 46, 8395; Dose, C., et al., *Org. Lett.* 2005, 7, 4365; Huang, H., et al., *Arch. Pharm. Res.* 2012, 35, 517; Avitabile, C., et al., *PLoS ONE* 2012, 7, 1; De Costa, N., et al., *PLoS ONE* 2013, 8, 1; Niu, Y., et al., *J. Org. Biomol. Chem.* 2013, 11, 4283; Dezhenkov, A. V., et al., *Medeleev Commun.* 2015, 25, 47). We showed that the enhancements in binding affinity and sequence selectivity of PNA upon introduction of an (S)-chiral center (prepared from L-amino acid) at this position emanate from backbone preorganization, a conformational transition from a globular fold into a RH helical motif (Dragulescu-Andrasi, A., et al., *J. Am. Chem. Soc.* 2006, 128, 10258; Yeh, J. I., et al., *Am. Chem. Soc.* 2010, 132, 10717). However, on the basis of these initial studies with limited stereochemical exploration, it was not clear whether the helical sense of γPNA could be reversed simply by switching the chirality at the γ-backbone, and if so, whether the resulting RH and LH conformers would be able to recognize each other, or how they would interact with DNA or RNA. To address these and other related questions, we synthesized the (S)- and (R)-γ-Me chiral PNA building blocks along with the corresponding oligos and characterized their conformations and hybridization properties and molecular self-assembly capability. We selected a pentameric sequence (Table 3), devoid of a self-hybridization possibility, as a starting point because our previous work showed that this particular class of chiral PNA exhibits unusually strong binding affinity and sequence selectivity for DNA as well as RNA (Rapireddy, S., et al., *J. Am. Chem. Soc.* 2007, 129, 15596). Since PNA-PNA is generally thermodynamically more stable than a PNA-DNA or PNA-RNA duplex (Wittung, P., et al., *Nature* 1994, 368, 561), we surmised that a 5mer sequence might be sufficient to form a stable duplex with its complementary partner.

Conformational Analysis.

Figure 8:
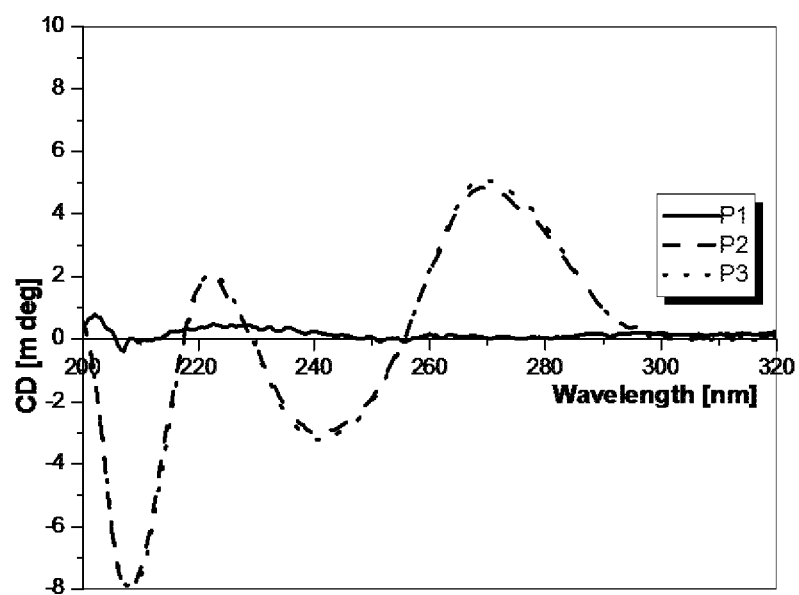
FIG. 8. CD profiles of PNA (P1) and RH-γPNA (P2 and 3) oligos at 1 μM strand concentration each, prepared in sodium phosphate buffer (10 mM sodium phosphate, 0.1 mM EDTA, 100 mM NaCl, pH 7.2) and recorded at 25° C. P2 and 3 contained the same (S)-Me group at the γ-backbone. The only difference between the two oligos was the chirality of the terminal lysine residues, one contained L while the other contained D. P1: H-LLys-GACCACAGAT-LLys-NH$_2$, P2: H-LLys-GACCACAGAT-LLys-NH$_2$, P3: H-DLys-GACCACAGAT-DLys-NH$_2$. The result indicates that the chirality of the terminal lysine residues has no bearing on the backbone organization or helical sense of γPNA.

To determine the effect of γ-backbone chirality on the conformation of PNA, we measured the CD spectra of PNA1 through 6, individually and after hybridization to their partner strands containing matching sequence and helical sense. Note that PNA3 and 4 contained chemical building blocks with (S)-Me and PNA5 through 9 with (R)-Me at the γ-backbone. As such we expected the first set to adopt an RH helical motif, as demonstrated in our earlier study (Dragulescu-Andrasi, A., et al., *J. Am. Chem. Soc.* 2006, 128, 10258; Rapireddy, S., et al., *J. Am. Chem. Soc.* 2007, 129, 15596), while the helical sense of the latter set was unknown and needed to be determined. The stereochemistry of the terminal lysine residue has no bearing on the conformation or helical sense of PNA as an individual strand (FIG. 8). Lysine residues were incorporated at the terminal positions of PNA to improve water solubility and minimize self-aggregation. The stereochemistry, L or D, was appropriately chosen to provide enantiomeric backbone uniformity with respect to that the γ-position.

Figure 9:
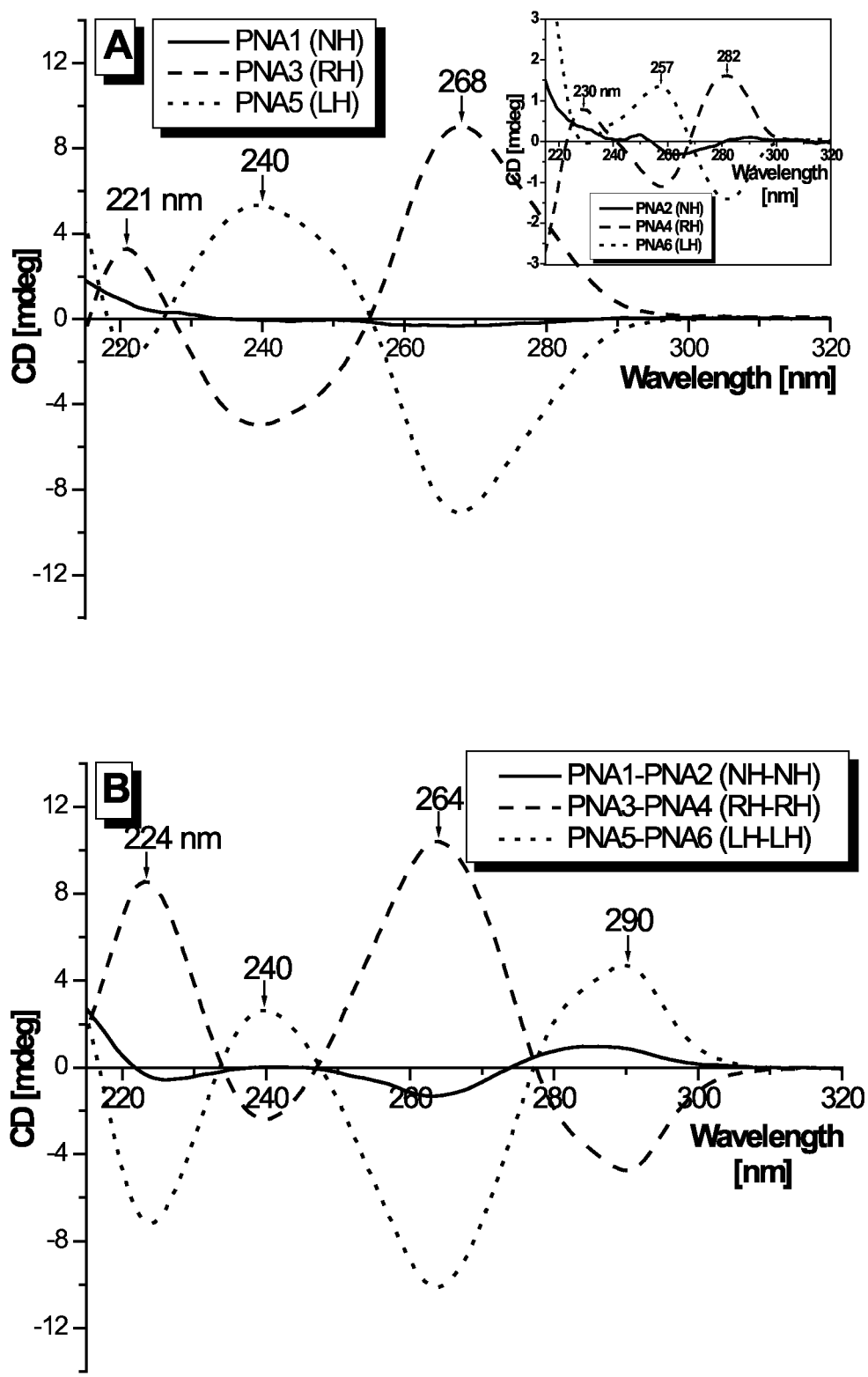
FIG. 9. CD spectra of (A) unhybridized (single-stranded) PNA and γPNA oligos, and (B) the corresponding PNA-PNA and γPNA-γPNA duplexes at 5 μM strand concentration each, recorded at 22° C. Inset in A: CD spectra of PNA2, 4 and 6. Otherwise stated, all samples employed in the CD, UV and fluorescent measurements were prepared in sodium phosphate buffer (10 mM sodium phosphate, 0.1 mM EDTA, 100 mM NaCl, pH 7.2).
Figure 10:
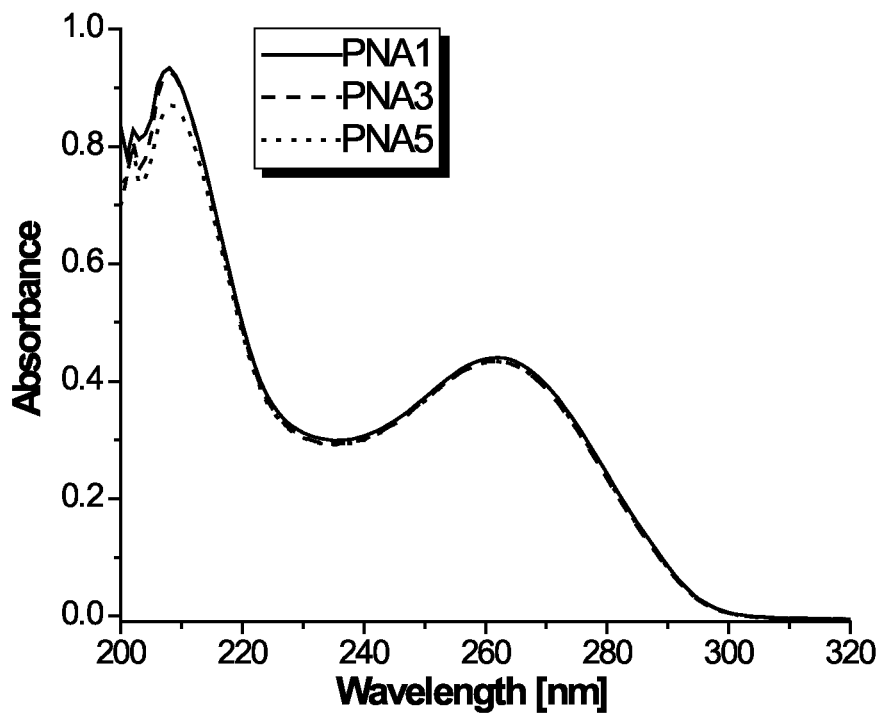
FIG. 10. UV-absorption profiles of PNA1, 3 and 5 at 5 μM strand concentration each, prepared in sodium phosphate buffer and recorded at 95° C. This result shows that the samples employed in the CD measurements shown in FIG. 9A were of the same concentrations.
Figure 11:
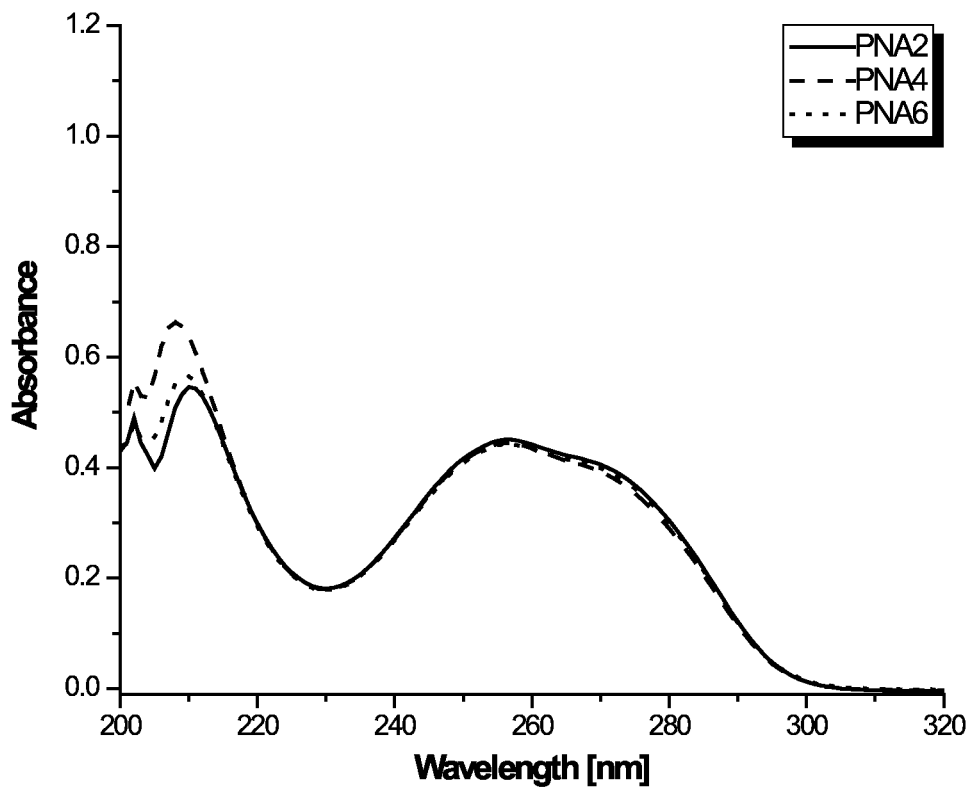
FIG. 11. UV-absorption profiles of PNA2, 4 and 6 at 5 μM strand concentration each, prepared in sodium phosphate buffer and recorded at 95° C. This result shows that the samples employed in the CD measurements shown in FIG. 9A (Inset) were of the same concentrations.
Figure 12:
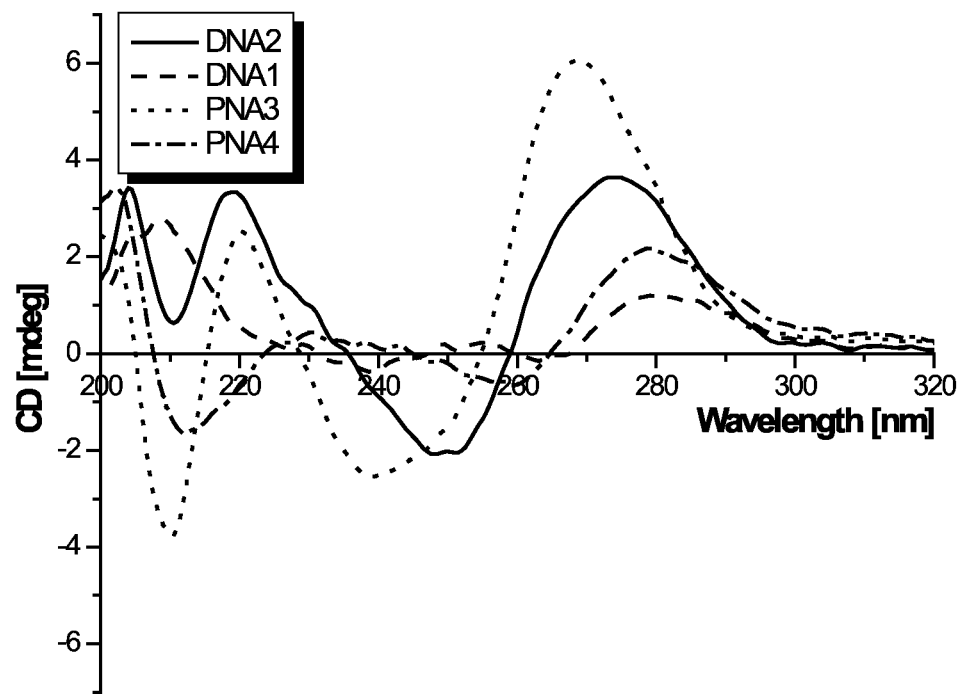
FIG. 12. CD profiles of DNA (DNA1 and 2) and RH-γPNA oligos (PNA3 and 4) at 5 μM strand concentration each, prepared in sodium phosphate buffer and recorded at 25° C. DNA1 and 2 contained the same nucleobase sequence as PNA3 and 4, respectively. DNA1: 5'-GTTGG-3', DNA2: 5'-CCAAC-3', PNA3: H-LLys-CCAAC-LLys-NH$_2$, PNA4: H-LLys-GTTGG-LLys-NH$_2$. Note that DNA2 and PNA3 contained the same nucleobase sequence, and so were DNA1 and PNA4. Comparisons of the CD profile of PNA3 to that of DNA2 and PNA4 to that of DNA1 reveal that PNA oligos consistently induced significantly greater CD signals than their DNA counterparts.

As expected, no CD signals were observed for PNA1 or 2 in the nucleobase absorption regions (200-320 nm), indicating that in the unhybridized (single-stranded) state PNA does not have a defined helical conformation (FIG. 9A). We ruled out the possibility of PNA adopting a racemic mixture of RH and LH helices based on prior analysis (Dragulescu-Andrasi, A., et al., J. Am. Chem. Soc. 2006, 128, 10258). However, in the case of PNA3 through 6, pronounced CD signals were observed. The CD spectrum of PNA3, with (S)-Me at the γ-backbone, exhibited a distinct exciton coupling pattern, with maxima at 268 and 221 nm and minimum at 240 nm and a cross-over at 255 nm, characteristic of a right-handed helix (Wittung, P., et al., *Nature* 1994, 368, 561). We ruled out the possibility of self-hybridization based on concentration and temperature dependent CD measurements (Dragulescu-Andrasi, A., et al., *J. Am. Chem. Soc.* 2006, 128, 10258). In contrast, PNA5, which contained an identical nucleobase sequence as that of PNA3 but with the opposite γ-backbone stereochemistry, displayed a mirror-image CD profile, in both pattern and amplitude, indicating that it formed an exact LH helical motif. Similar CD profiles were observed for PNA4 and 6, but they were slightly red-shifted and significantly weaker in signals compared to that of PNA3 and 5 (FIG. 9A, Inset), despite the fact that they were of the same concentrations (FIGS. 10 and 11). One plausible explanation for the difference in the CD amplitude is the difference in the degree of base-stacking. It has been reported that thymine has the lowest base-stacking energy among the four nucleobases (Kadhane, U., et al. *Phys. Rev. E.* 2008, 77, 021901/1). This suggestion is consistent with our finding; PNA4 and 6 induced weaker CD signals than PNA3 and 5 because they contained two thymine residues, as compared to none for the latter set. We corroborated this finding with DNA oligonucleotides of the same sequence (FIG. 12), confirming the generality of this phenomenon. Interestingly, comparison of the two systems revealed that γPNA oligos produced significantly stronger CD signals than DNA, hinting greater base-stacking and structural rigidity of the former. Together these results show that PNA can be directed to fold into a RH or LH helix simply by switching the stereochemistry at the γ-backbone.

An interesting finding is in comparison of the CD spectra of the individual strands (FIG. 9A) to that of the duplexes (FIG. 9B). The CD amplitudes of the duplexes are merely the sum of the individual strands. This result supports the notion that, individually, γPNA oligos are already preorganized into the bound state prior to recognition and, as such, hybridization is likely to follow the Fischer's "key and lock" hypothesis (Fischer, E., *Ber. Dtsch. Chem. Ges.* 1894, 27, 2985). Such binding should translate into higher affinity and sequence selectivity due to the reduction in the entropic penalty and an increase in the backbone rigidity, thereby making the system less accommodating to structural changes. However, in the case of the unmodified PNA1-PNA2 duplex, only weak CD signals were observed, suggesting one of two possibilities: (1) that only a small fraction of the duplex was formed, with the rest in the single-stranded state, or (2) that the duplex existed in nearly equal proportions of RH and LH. As such, the CD signals produced by the RH helix would be cancelled by those produced by the LH, hence the weak CD signals. The chirality of the amino acid residue incorporated at the C-terminus has been shown to have no effect on the backbone organization or helical sense of PNA in the single-stranded state (FIG. 8); however, it has a small, but notable, effect on the helical preference of the PNA-PNA duplex (Wittung, P., et al., *J. Am. Chem. Soc.* 1995, 117, 10167). On the basis of the CD data alone, it would be difficult to discern one from the other, especially for such a relatively short sequence; however, our UV-melting data discussed in the next section suggests that it is the former.

Thermal and Thermodynamic Stabilities of the Conformationally-Matched Homoduplexes.

Figure 13:
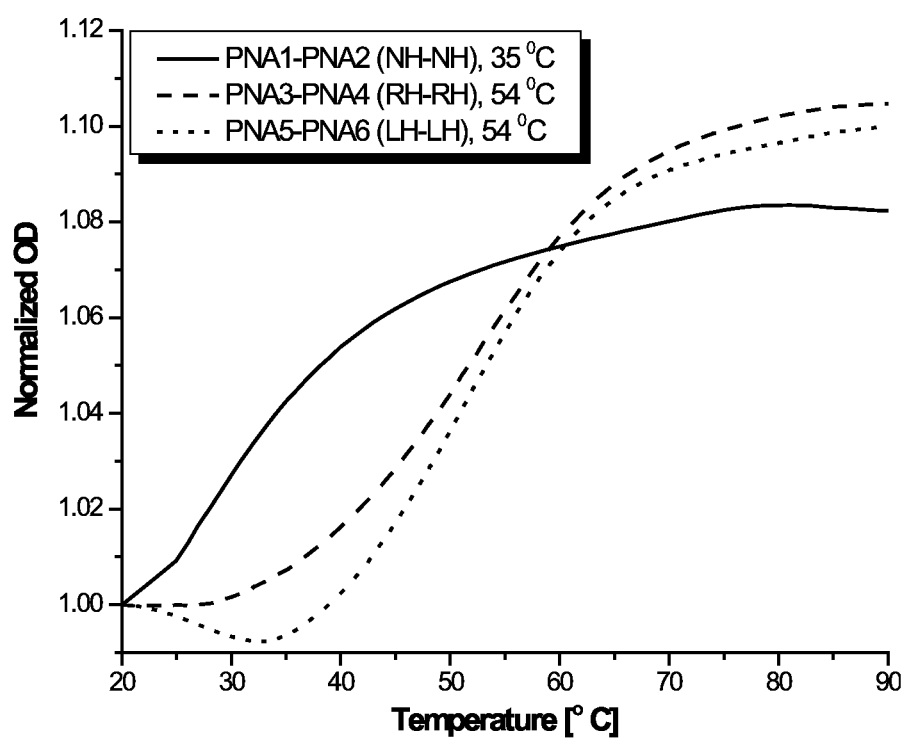
FIG. 13. UV-melting profiles of PNA-PNA and γPNA-γPNA duplexes at 5 μM strand concentration each in sodium phosphate buffer.

UV-melting experiments were conducted to determine the effect of γ-backbone modifications on the thermal stability of PNA-PNA duplexes. Our results showed that the melting profiles of the conformationally-matched γPNA-γPNA duplexes (PN3-PNA4 and PNA5-PNA6) are nearly identical to each other (FIG. 13), with the melting transitions (Tms) of 54±0.5° C., corresponding to a net gain in ΔTm of +19° C., in comparison to that of the unmodified PNA1-PNA2. Concentration-dependent Van't Hoff analysis was employed to determine the thermodynamic parameters of the two duplexes: $\Delta H°_{298K}$=−222±20 kJ/mol, $T\Delta S°_{298K}$=−581±60 kJ/mol, and $\Delta G°_{298K}$=−52±1 kJ/mol. The data translates to an average binding free energy of −10.4±0.3 kJ/mol per base-pair, in comparison to −6.3 to −8.2 kJ/mol per base-pair as previously determined for PNA-PNA ((Sforza, S., et al., *Eur. J. Org. Chem.* 1999, 197; Ratilainen, T., et al., *Biochemistry* 1998, 37, 12331; Tomac, S., et al., *J. Am. Chem. Soc.* 1996, 118, 5544)). We attributed the improvement in thermodynamic stability to backbone preorganization. We had previously attempted to discern the binding free energy gains of γ-backbone modifications, however, to no avail. We did not observe an obvious trend in the entropy term, as would be expected for binding of conformationally preorganized substrates, but instead we noted an entropy-enthalpy compensation (Sahu, B., et al., *J. Org. Chem.* 2011, 76, 5614). This is because the conformational transformation of PNA is not from a floppy, random-coil to a more compact helical state, but rather from one compact (globular) state to another. PNA adopts a globular motif in order to maximize the solvophobic effect, as the result of the charge-neutral backbone and hydrophobic nucleobases (Seitz, O. Angew. *Chem.-Int. Edit. Engl.* 2000, 39, 3249; Ranasinghe, R. T., et al., *J. Chem. Comm.* 2001, 1480; Kuhn, H., et al., *J. Am. Chem. Soc.* 2002, 124, 1097). The difference in the thermodynamic stability of the duplexes, with PNA1-PNA2 being less stable than PNA3-PNA4 or PNA5-PNA6, is consistent with the weaker CD signals observed for the unmodified PNA duplex, indicative of its small fraction present in the solution.

Sequence Specificity.

Figure 14:
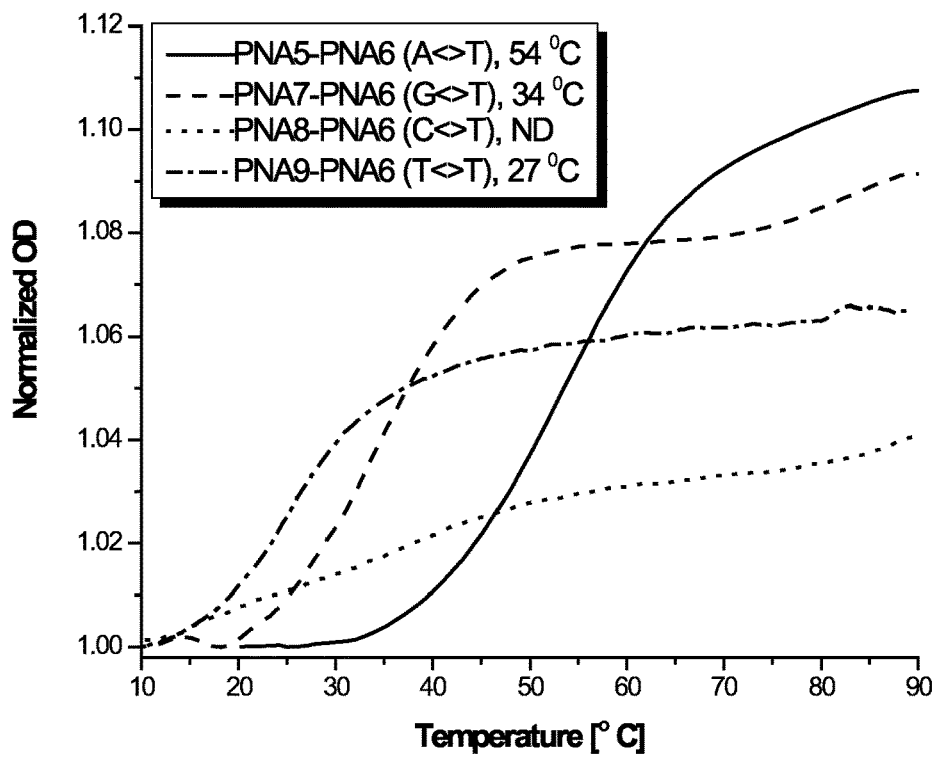
FIG. 14. UV-melting profiles of γPNA-γPNA pairs containing perfect-match and single-base mismatches. The concentration of each strand was 5 μM, prepared sodium phosphate buffer. The Tms were determined by taking the first derivative of the melting curves.

Next, we assessed the ability of γPNA to discriminate between closely related sequences. Comparison of the melting profiles of the single-base mismatched duplexes to that of the perfect-match revealed that the destabilization ($\Delta T_m$) is at least −20° C. (Table 7 and FIG. 14), significantly greater than previously observed PNA and DNA mismatches (Ratilainen, T., et al., *Biochemistry* 2000, 39, 7781). The wobble G< >T pair (PNA7-PNA6) was the least destabilizing because such a mismatched pair still retains two H-bonds. Destabilization was more pronounced for the T< >T mismatch (PNA9-PNA6, $\Delta T_m$=−27° C.), and no melting transition was observed for T< >C (PNA8-PNA6), indicating that hybridization did not take place at the indicated temperature range. This result shows that despite the strong binding affinity, γPNA can discriminate between closely related sequences. We attributed the significant improvement in sequence selectivity to an increase in backbone rigidity and to the greater energetic penalty for each base-pair as the result of the shorter sequence (Silverman, A. P.; Kool, E. T. Chem. Rev. 2006, 106, 3775).

TABLE 7

Tms of matched and single-base mismatched duplexes

| Duplex | $T_m$ (° C.) | $\Delta T_m$ (° C.) |
|---|---|---|
| PNA5-PNA6 | 54 | |
| PNA7-PNA6 (G<>T) | 34 | −20 |
| PNA8-PNA6 (C<>T) | ND | |
| PNA9-PNA6 (T<>T) | 27 | −27 |

Recognition Orthogonality.

Figure 15:
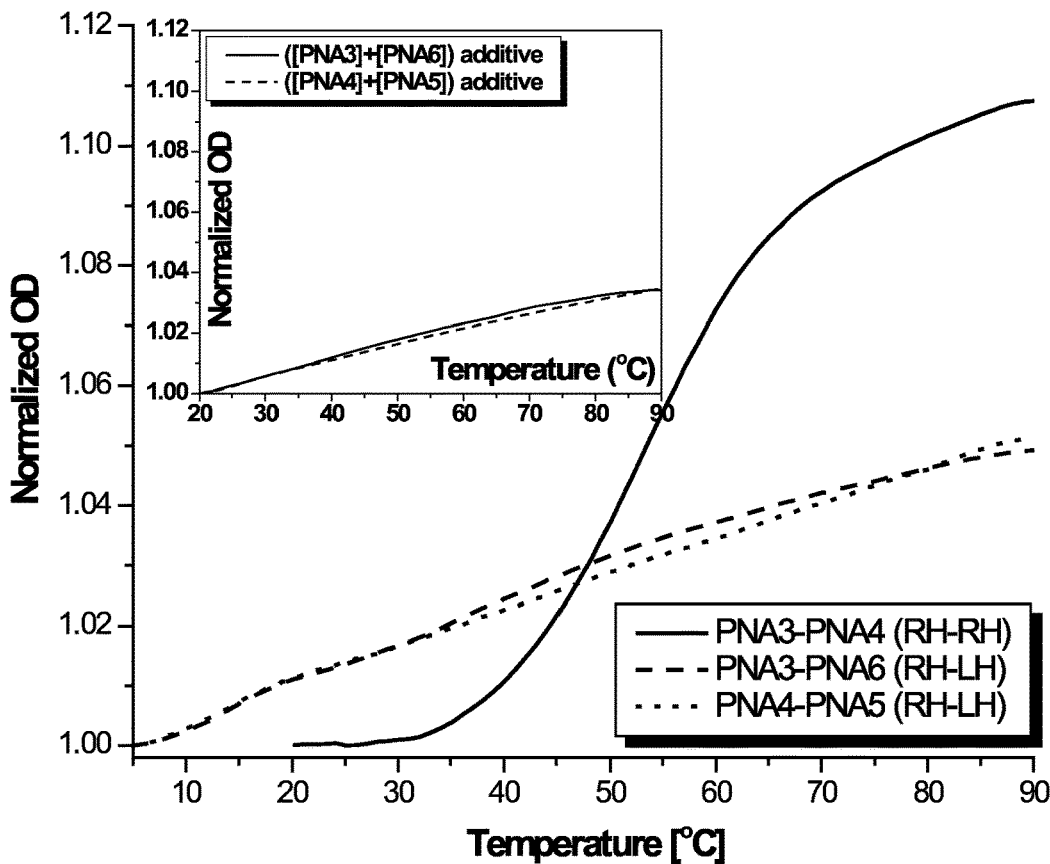
FIG. 15. UV-melting profiles of γPNA-γPNA duplexes containing conformationally-matched (RH-RH) and mismatched (RH-LH and LH-RH) helical senses at 5 μM strand concentration each in sodium phosphate buffer.

The opposing helical preference of γPNA oligos, RH for PNA3 and 4 and LH for PNA5 and 6, suggested that they might not be able to hybridize to one another despite the sequence complementarity. Such an inherent property would be valuable, if it could be demonstrated, for programming molecular assembly because of the added dimension in recognition. To determine if recognition orthogonality was in play between RH and LH, we measured the thermal stabilities of the conformationally mismatched (PNA3-PNA6 and PNA4-PNA5) and compared them to that of the matched γPNA-γPNA homoduplexes (PNA3-PNA4 and PNA5-PNA6). Since the melting profiles of the homoduplexes were shown to be nearly identical to each other (FIG. 13), only one was chosen for comparison. Inspection of FIG. 15 reveals that the thermal profiles of the conformationally mismatched PNA3-PNA6 (RH-LH) and PNA4-PNA5 (RH- LH) pairs have no discernible transitions. Rather, they closely resemble that of the sum of the individual strands (FIG. 15, Inset), indicating that these conformationally mismatched pairs did not hybridize to each other. We attributed the residual hyperchromicities to the melting (or unstacking) of the nucleobases within each strand.

Figure 16:
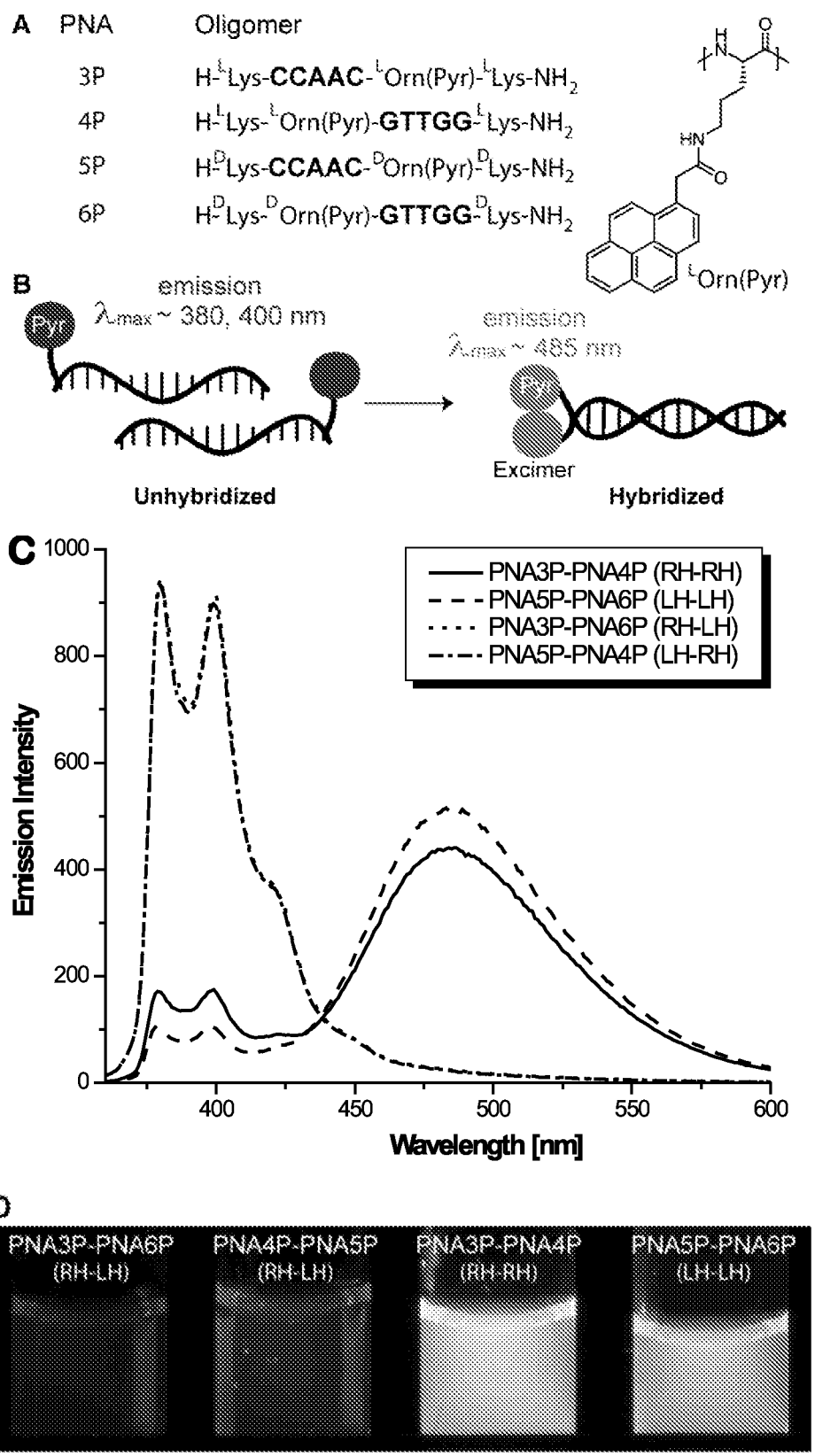
FIG. 16. (A) Sequence of γPNA oligos employed in the fluorescent measurements, along with the structure of pyrene to which they are covalently linked. (B) Schematic diagram showing the expected emissions of pyrene in γPNA oligos in the hybridized and unhybridized states. (C) Fluorescent spectra of the complementary γPNA strands containing conformationally matched (RH-RH and LH-LH) and mismatched (RH-LH and LH-RH) helical senses following excitation at 344 nm. (D) Photographs of the samples employed in (C) under a hand-held UV-lamp.

To independently verify the recognition orthogonality of the conformationally-mismatched γPNA oligos, we performed fluorescent experiments using pyrene as a reporter probe. Pyrene has been used as a fluorescent marker to investigate the conformational arrangements of proteins and nucleic acids, where formation or disruption of the pyrene excimer is indicative of folding or denaturation (Sahoo, D., et al., Biochemistry 2000, 39, 6594; Yang, C. J., et al., Proc. Nat. Acad. Sci. USA 2005, 102, 17278; Oh, K. J., et al., Nuc. Acid Res. 2006, 34, 152). When excited at 344 nm, the pyrene monomers emit fluorescent signals at 380 and 400 nm, but when they are stacked with each other to form dimers, their excitation results in the formation of excimers which emit at 485 nm. This ~100 nm red-shift in the fluorescent emission provides a convenient means for monitoring the on- and off-state of molecular interactions. By attaching pyrene to the terminal regions of the complementary γPNA pairs, one at the C— and the other at the N-terminus (FIG. 16A), one could easily determine if hybridization takes place by monitoring the pyrene emissions. In the absence of hybridization, the pyrenes on individual γPNA strands exist as monomers; and as such, their excitation at 344 nm should produce blue fluorescent emissions at 380 and 400 nm (FIG. 16B). However, upon hybridization, whereby the two complementary γPNA strands come together and the opposing pyrene ligands are stacked with each other to form dimers, excitation at the same wavelength (344 nm) should produce excimers which emit fluorescence signals at 485 nm. The large shift in the emissions should enable detection even with the naked eye.

The samples were prepared by mixing equimolar concentrations of the various γPNA pairs, conformationally-matched as well as mismatched, and annealed at 95° C. for 5 minutes. The mixtures were excited at 344 nm and the fluorescent emissions were recorded from 340 to 600 nm at room temperature. As expected, the samples with complementary sequence and conformationally matched pairs (PNA3P-PNA4P and PNA5P-PNA6P) showed distinct pyrene excimer emissions at 485 nm, with residual monomer emissions at 480 and 400 nm (FIG. 16C). The excimer emissions indicate that the two strands hybridized to each other. We attributed the residual monomer emissions to the small fraction of the single strands present in the solution in equilibrium with the duplex. In contrast, the conformationally mismatched pairs (PNA3P-PNA6P and PNA4P-PNA5P) showed only the monomer emissions, indicating the absence of hybridization. FIG. 16D shows a photograph of the four samples irradiated with a short-wavelength hand-held UV-lamp, confirming the recognition orthogonality of the conformationally mismatched pairs. This result is consistent with the UV and CD measurements, indicating that γPNA strands with complementary sequence but opposing helical sense do not hybridize to each other.

Hybridization of RH- and LH-γPNA to RNA and DNA.

Figure 17:
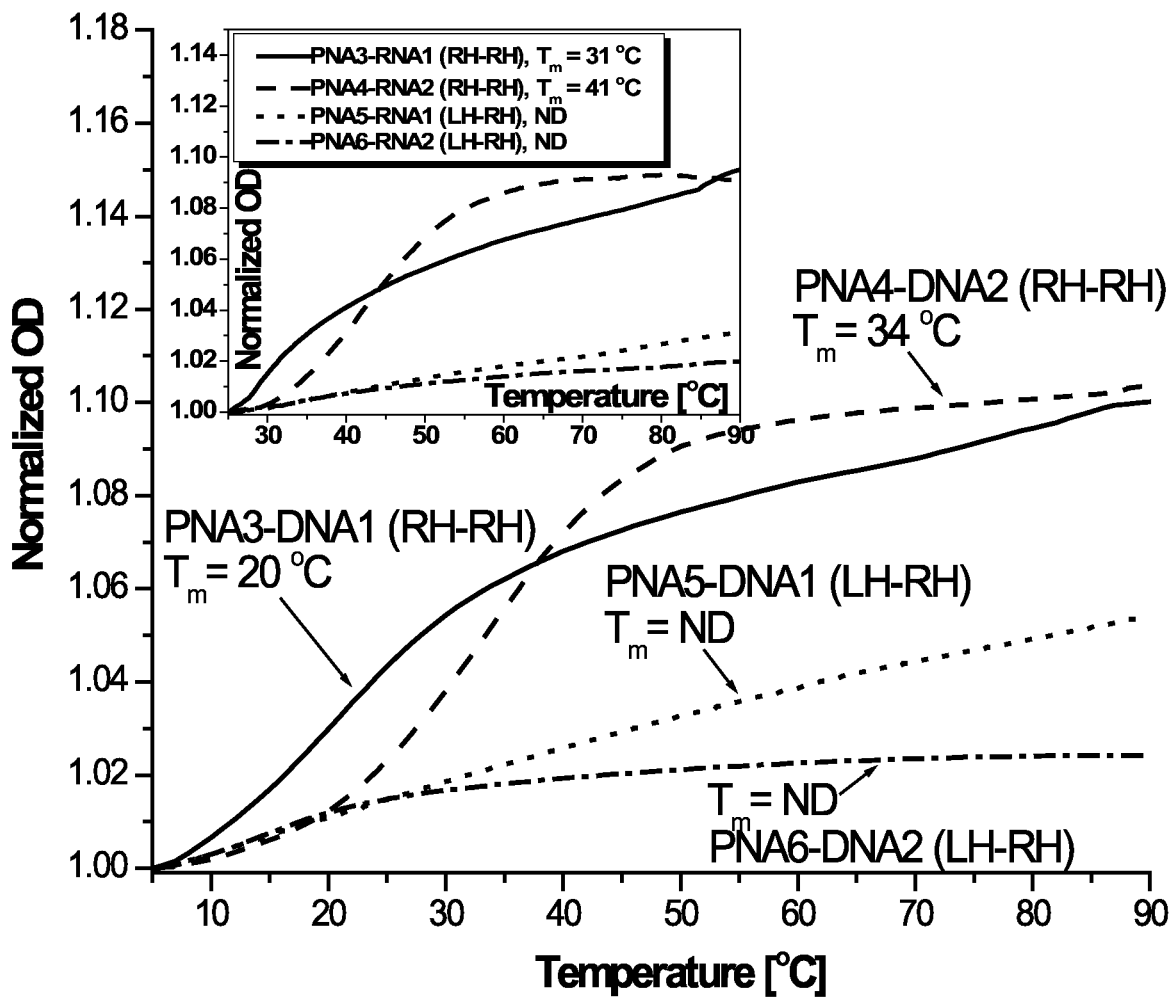
FIG. 17. UV-melting profiles of γPNA-DNA pairs with matched (RH-RH and LH-LH) and mismatched (LH-RH) helical sense at 5 μM strand concentration each. Inset: melting curves of γPNA-RNA pairs. DNA1: 5'-GTTGG-3', DNA2: 5'-CCAAC-3', RNA1: 5'-GUUGG-3', RNA2: 5'-CCAAC-3'.

Next, we assessed the ability of RH- and LH-γPNA to hybridize to complementary DNA or RNA strand. UV-melting data revealed that, similar to the observations made with the γPNA-γPNA homoduplexes, RH-γPNA oligos (PNA3 and PNA4) were able to hybridize to complementary DNA (FIG. 17) as well as RNA strands (Inset), as evidenced from the sigmoidal profiles and clear melting transitions. In line with the previous observation, we found the thermal stabilities of the RH-γPNA-RNA duplexes to be 5-10° C. higher than that of RH-γPNA-DNA (Sahu, B., et al. J. Org. Chem. 2011, 76, 5614). In contrast, the conformationally mismatched LH-γPNA-DNA (PNA5-DNA1 and PNA6-DNA2) and LH-γPNA-RNA (PNA5-RNA1 and PNA6-RNA2) pairs did not show the two-state melting behaviors, indicating that LH-γPNA oligos did not hybridize to the complementary DNA or RNA strands. This result suggests the possibility of using LH-γPNA to organize molecular self-assembly and carrying out molecular computation in vivo without the concern for cross-hybridization with the endogenous genetic materials, or enzymatic degradation, since γPNA is non-natural and therefore should be impervious to recognition by proteases or nucleases (Demidov, V. V., et al., Biochem. Pharmacol. 1994, 48, 1310).

Dual Recognition of PNA with RH- and LH-γPNA.

Figure 18:
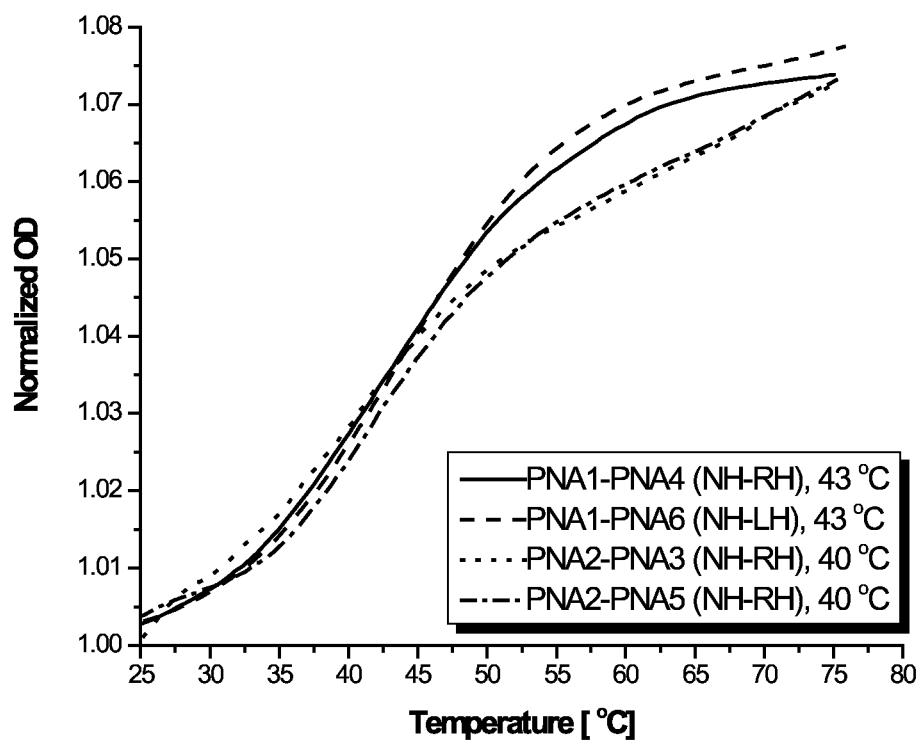
FIG. 18. UV-melting profiles of PNA-γPNA heteroduplexes, with the latter containing RH and LH helical motifs at 5 μM strand concentration each.

We have demonstrated that RH- and LH-γPNA oligos were unable to hybridize to each other and neither were LH-γPNAs to complementary RNA or DNA strands, due to conformational mismatch. Since PNA is achiral and does not have a well-defined conformation, we suspected that it might be able to hybridize to LH as well as RH-γPNA. Such a capability is valuable for translating the genetic information encoded in one conformer to another. FIG. 18 shows the UV-melting profiles of PNA1 and 2 after hybridization with the complementary LH- and RH-γPNA strands. Their inspection reveals that unmodified (achiral) PNA is able to hybridize to both the LH and RH conformers. The fact that the melting profiles of PNA1-PNA4 and PNA1-PNA6 are virtually identical to each other ($T_m$~43° C.), and likewise, PNA2-PNA3 and PNA2-PNA5 ($T_m$~40° C.), indicates that PNA has an equal propensity to hybridize to LH- as well as RH-γPNA. A slight variation in the thermal stability between the two sets was expected because of the inversion in the sequence. The ability of PNA to interface with LH- and RH-γPNA, as well as with DNA and RNA, makes it a versatile platform for storage and transmission of genetic information—one that is compatible with genetic materials, as well as one that is orthogonal to them. One such potential application is in-situ detection of genetic materials based on the HCR technology developed by Pierce and coworkers (Dirks, R. M., et al., ACS Nano 2014, 8, 4284).

Molecular Self-Assembly.

Figure 19:
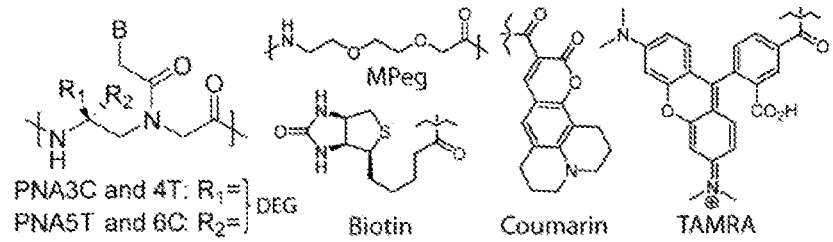
FIG. 19. (A) Sequence of γPNA oligos utilized in the assembly of polystyrene beads along with chemical structures of the various constituents. (B) Schematic diagram of streptavidin-coated polystyrene beads labeled with the indicated γPNA oligos through streptavidin-biotin binding. The naming system is as followed: bead size (2 or 10 μm), oligomer name (PNA3, 4, 5, or 6), fluorescent probe (C: Coumarin, T: Tamra), and helical sense in the parenthesis (RH or LH). For instance, 10-PNA4T (RH) stands for a polystyrene bead 10 μm in size, covalently coated with PNA4, marked by a Tamra (red) fluorescent probe, with the recognition code adopting an RH helical sense. (C) DIC images of different combinations of polystyrene bead mixtures. Insets in (i) and (iv): fluorescent images of the assembled polystyrene beads.
Figure 19:
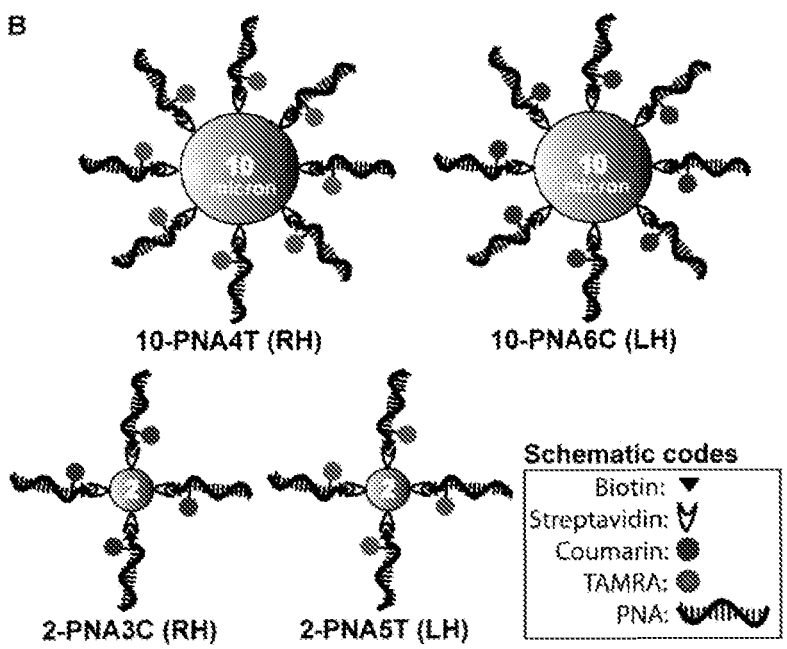
Figure 19:
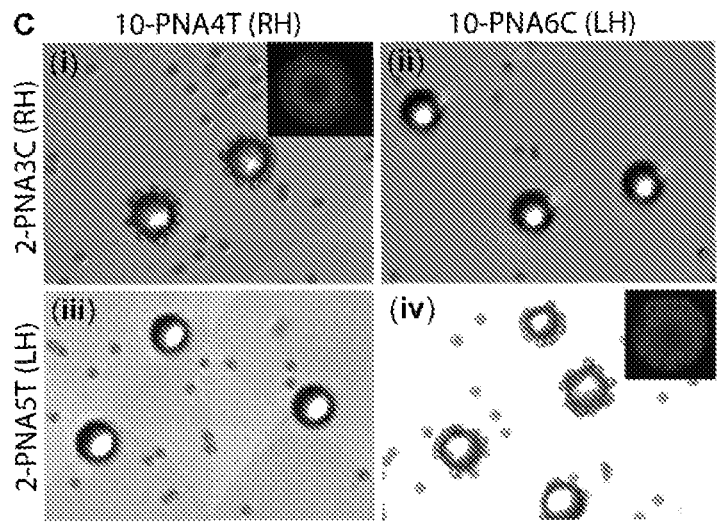

To demonstrate the feasibility and recognition orthogonality of the pentameric γPNA system in organizing molecular self-assembly, we employed two sets of polystyrene beads, 2 and 10 μm in size, with the surface coated with γPNA via biotin-streptavidin binding (FIG. 19A). To circumvent the possible collapse of relatively hydrophobic Me-γPNA oligos onto the surface of the polystyrene beads, we replaced the Me-group with diethylene glycol (DEG) at the γ-backbone, which we had previously shown to significantly improve water solubility and biocompatibility (Sahu, B.; et al., J. Org. Chem. 2011, 76, 5614). Additionally, a long, flexible (Mpeg)5 linker was inserted between the recognition module and biotin to provide greater conformational flexibility and ease of hybridization. The biotin and fluorescent probes, with the latter used to mark the helical sense of γPNA oligos, were covalently attached to the ornithine sidechain. FIG. 19B shows a scheme of the four types of polystyrene beads employed in the study. The assembly process was initiated by mixing equimolar concentrations of beads containing different combinations of conformationally matched and mismatched γPNA oligos, with the resulting DIC images shown in FIG. 19C after annealing at room temperature for 3 hrs. The results revealed that only polystyrene beads containing γPNA oligos with complementary sequence and matching helical sense were able to interact with each other and form the expected con-centric "small-on-large" bead arrangements [FIG. 19C, images (i) and (iv)]. The insets in images (i) and (iv) further confirmed the helical sense of γPNA oligos, as indicated by the color of the fluorescent probe. However, in the case of γPNA oligos with mismatched helical senses, no defined bead interactions were observed [images (ii) and (iii)], indicating that they did not recognize one another due to conformational mismatch; therefore, the 2 μM beads were not able to interact with and self-organize around the larger ones, despite the sequence complementarity. This result confirms the findings from the CD and UV-melting experiments, demonstrating the recognition orthogonality of LH- and RH-γPNA. To the best of our knowledge, this is the first example of a pentameric recognition module capable of organizing molecular self-assembly.

CONCLUSIONS

In summary we have demonstrated that PNA, which, as an individual strand, does not have a well-defined conformation in solution, can be preorganized into a RH or LH helical motif simply by installing an appropriate stereogenic center at the γ-backbone. LH- and RH-γPNA oligos hybridize to their partner strands containing complementary sequence and matching helical sense; however, they do not cross-hybridize with one another. Binding occurs with unusually high affinity and sequence selectivity, presumably through the "key and lock" motif with minimal conformational rearrangement as the result of backbone preorganization. Recognition modules, as short as 5 nts in length, can be used to organize and assemble micro-particles with high level of recognition orthogonality. Likewise, due to conformational mismatch, LH-γPNA oligos are unable to hybridize to complementary DNA or RNA strands. The recognition orthogonality of LH- and RH-γPNA can be interfaced with achiral PNA as well as with DNA and RNA, providing an "all-in-one" nucleic acid platform for programming molecular interactions and assembly.

The utility of PNA in molecular self-assembly and programming chemical reactivity has been demonstrated by Liu et al., Seitz et al. and Winssinger (Kleiner, R. E.; et al., *J. Am. Chem. Soc.* 2008, 130, 4646; Michaelis, J., et al., *Org. Biomol. Chem.* 2014, 12, 2812; and Winssinger, N., *Chimia* 2013, 67, 340). The added dimension in recognition orthogonality, combined with the superior binding affinity and sequence selectivity along with the ease of chemical synthesis and functional group diversification will certainly expand the utility of nucleic acid-based molecular engineering and computing, both in vitro and in vivo. The relatively small size of the recognition module (5 to 8 nts in length) should be relatively easy and cost-effective to synthesize in high-throughput and to scale-up. Moreover, the reduction in size should make cell delivery more manageable and efficient, in comparison to the longer traditional antisense reagents, when functionalized with the appropriate chemical groups or employing an appropriate delivery vehicle. In addition to the LH and RH conformational orthogonality, another dimension of recognition orthogonality that is implemented is base-pairing. Inclusion of unnatural base-pairs, such as isoC and isoG and among others (Piccirilli, J. A., et al. *Nature* 2000, 343, 33 and Hirao, I., et al., *Acc. Chem. Res.* 2012, 45, 2055), that do not recognize the natural nucleobases expands the recognition repertoire of such a system further, providing greater flexibility and level of orthogonality in programming molecular interaction—for organization and assembly of materials as well as for molecular computing.

Example 4

This Example provides a rapid and convenient means for diagnosing genetic and infectious diseases, in a laboratory setting as well as in the field. The present detection method has four components: detection of the nucleic acid target; maintenance and restoration of the signal strength; conversion of the detection signal from a right-handed to left-handed helical sense to minimize cross-interference with endogenous genetic materials; and amplification and detection of the signal.

The methods exemplified by this example provide rapid, on-site nucleic acid diagnostics. This is accomplished by employing a series of molecular logic gates to detect the analyte, transmit and amplify the signal in-situ, in the presence of endogenous genetic materials without the use of enzyme or need for background noise washing prior to detection. The new methodology takes advantage of the conformational organization of γ-peptide nucleic acid (γPNA), a nucleic acid mimic that can be directed to fold into either a right-handed or left-handed helix depending on the stereochemistry at the γ-backbone, and unnatural nucleobases as a means for target detection, signal processing, and amplification.

Like polymerase chain reaction (PCR), reverse-transcriptase/PCR (RT-PCR), and isothermal amplification, detection of nucleic acids by the present invention, I-NA-DSA, is highly sensitive. However, unlike the established methods, which are labor intensive and time-consuming and prone to cross-contamination and generation of false positives, the present invention is more robust and performed in-situ in the primary specimen without the use of enzyme or concern for background noise. Since the amplification step occurs through a cascade hybridization chain reaction (HCR) free of enzyme, detections of DNA and RNA are carried out the same way, without the need for an additional reverse transcription step for the latter case.

The method exemplified by this example provides several distinctive advantages over existing nucleic acid-based detection methods in terms of speed, sensitivity, specificity, cost, versatility, and portability.

Figure 20:
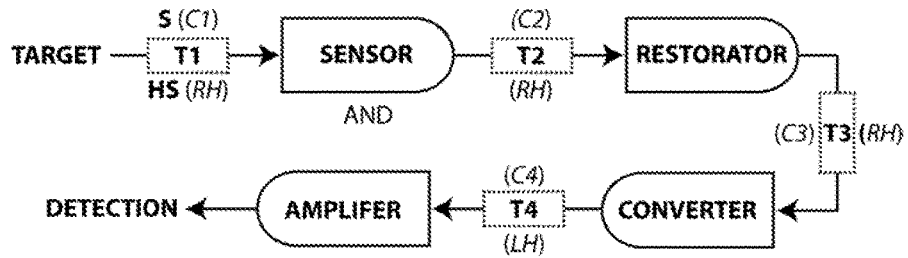
FIG. 20 illustrates the four components of the present invention, the I-NADSA logic gates: (1) SENSOR, (2) RESTORATOR, (3) CONVERTER, and (4) AMPLIFIER.

Generally, provided herein is a series of molecular logic gates. FIG. 20 depicts the four components: (1) detection of the nucleic acid analyte (SENSOR), (2) maintenance and restoration of the signal strength (RESTORATOR), (3) conversion of the detection signal from one form, such as the right-handed (RH) form, to another, such as the left-handed (LH) form, to minimize cross interference with the surrounding environment (CONVERTER), and amplification of the signal (AMPLIFER). Each 'AND' operator takes in a single 'physical' input and produces a single 'physical' output in the form of a nucleic acid operant (T1 through T4), with each operant carrying two 'bits' of information: sequence (S) and helical sense (HS; RH: right-hand, NH: no helical preference, or LH: left-hand). The two requirements (complementary S and HS) must be met in order for the operator to produce an output.

Figure 21:
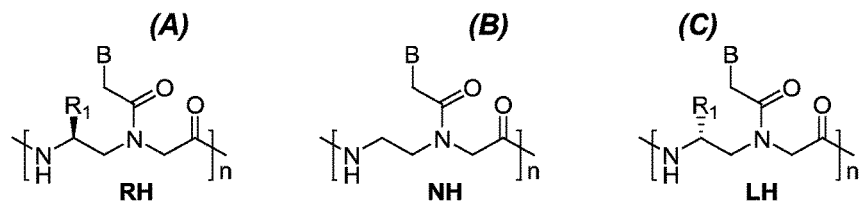
FIGS. 21A-D show structures of the chemical building blocks: right-handed (RH) γPNA (FIG. 21A); non-helical preference (NH) PNA (FIG. 21B); left-handed (LH) γPNA backbone (FIG. 21C); and structures of natural and unnatural nucleobases along with the corresponding base-pair interaction patterns (FIG. 21D).
Figure 21:
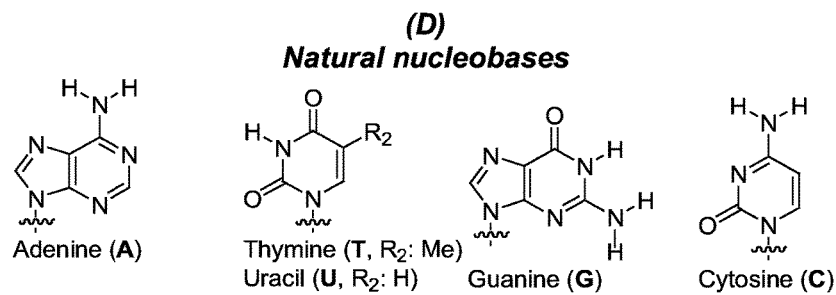
Figure 21:
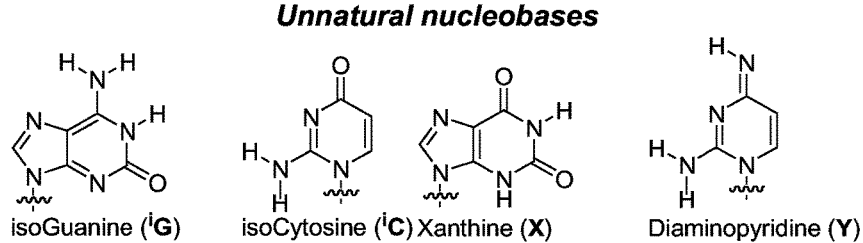
Figure 21:
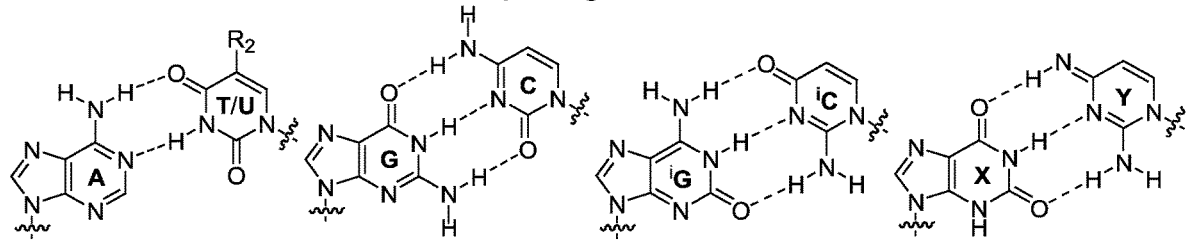

The present invention uses the conformational organization of γPNA, a nucleic acid mimic which can be directed to fold into either a right-handed or left-handed helix; and unnatural nucleobases. FIG. 21 depicts the structures of these chemical building blocks; including the chemical structure of a (FIG. 2A1) right-handed (RH) γPNA, (FIG.

21B) non-helical preference (NH) PNA and (FIG. 21C) left-handed (LH) γPNA backbone, B=nucleobase. As well as, (FIG. 21D) structures of natural and unnatural nucleobases along with the corresponding base-pair interaction patterns. R1 can be any chemical group except hydrogen, including amino acid side-chains.

The nucleic-acid detection starts with the DNA or RNA target (T1) binding to the toe-hold region of the sensor (1). Branch migration (2) and chain displacement (3) result in the separation of P (same as T2) from S. Due to an increase in backbone flexibility, T2 undergoes further self-splicing (4), resulting in the cleavage of the N-terminal domain (n). Hybridization of T3 (RH) to the toe-hold region of the converter through orthogonal (m-m') nucleobase interactions (5), followed by another round of branch migration (6) and strand displacement (7), results in the release of T4 (LH). Binding of T4 to the first amplifier (8), and then to the second (9), triggers a cascade reaction and the assembly of an extended duplex structure (10). As an example, a FRET-based detection system is shown. FIG. 22 illustrates the molecular operations of the present invention, and uses the nomenclature described below. The probe strands are represented as directional lines, with the hook denoting the N-terminus. The nature of each strand is denoted by an asterisk, opened square, or filled square, with the asterisk denoting a right-handed (RH) γPNA, opened square a non-helical preference (NH) PNA, and filled square a left-handed (LH) γPNA. Each strand is subdivided into domains, continuous nucleotides that act as a unit in hybridization, branch migration, or dissociation. Domains are represented by italic lowercase letters, and those with the apostrophe are complements of those without (e.g., a' is complementary to a). All domains are comprised of chemical building blocks with natural nucleobases as recognition elements except for m and m', which contain unnatural (orthogonal) nucleobases. See FIGS. 23-26 for additional information about the sensor, restorator, converter, and amplifier.

The first component of the present invention, the sensor, includes of a protecting (P) strand and sensing (S) strand hybridized to one another to form a 'frustrated' hairpin structure m with unnatural nucleobases as recognition elements. This is described in FIG. 4. Because a γPNA-γPNA duplex is thermodynamically more stable than a γPNA-DNA or γPNA-RNA, a relatively short P strand could be used to protect the S strand from binding to spurious sequences, leaving a single strand toe-hold region for sequence sampling and initiating target binding. The thermodynamics of the sensor is tuned in such a way that it remains intact in the absence of the target and undergoes a strand displacement reaction, as shown in steps 1-3, in the presence of the target. For a typical design, the P strand is in the range of 14-21 nt (ba domains≈5-7 nt, m domain≈4-6 nt, n domain≈5-7 nt), and the S strand 14-20 nt. Because of its relatively short flanking arms (5-Int in length), once released the P strand does not have sufficient binding free energy to form a stable duplex with other endogenous nucleic acid targets at physiological temperature. Notice that in this case the m domain is unable to partake in the H-bonding interactions with DNA or RNA because it contains unnatural recognition elements. Besides the flush duplex, other possible designs of the sensor include placement of P in the interior regions, different configurations of the hairpin, and an intramolecular system where P covalently linked to S.

Figure 24:
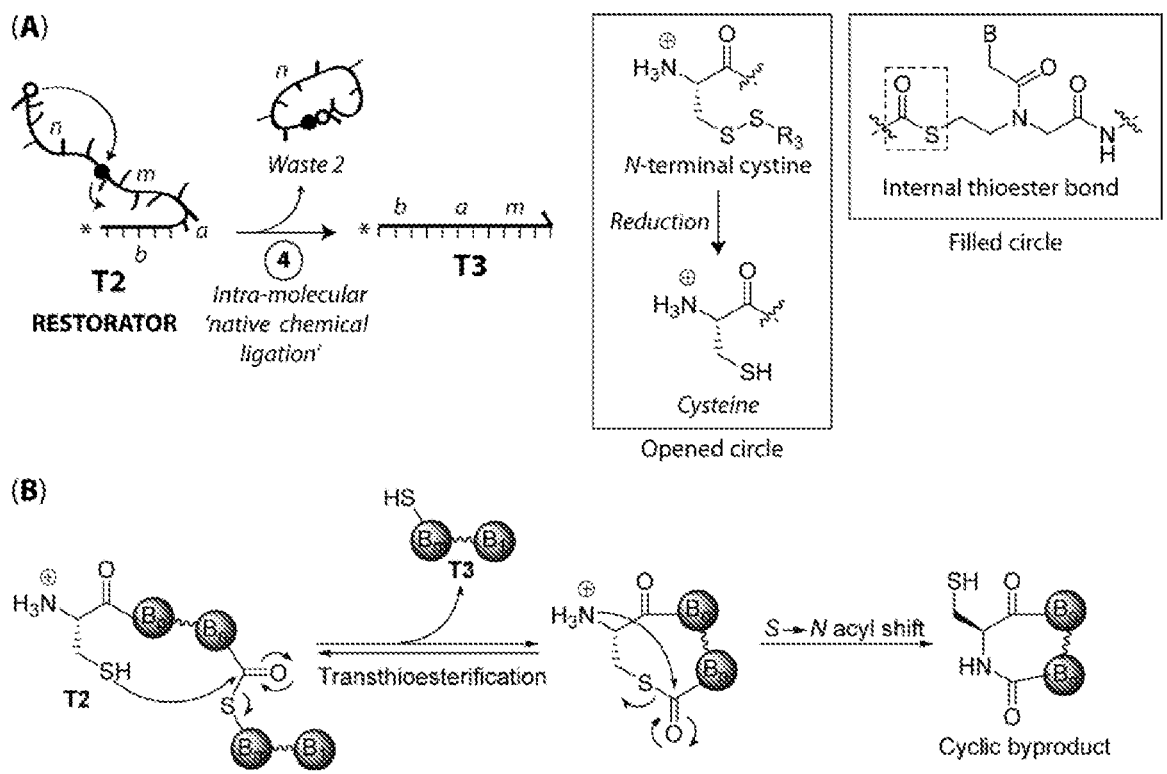
FIG. 24 depicts the restorator as described in Example 2.

The second component is the restorator, this is detailed in FIG. 24. In addition to the orthogonal m domain, the P strand (same as T2) contains an internal thioester bond (filled circle) and N-terminal cystine, specifically designed as a safeguard for T2 in preventing it from binding to and being trapped by endogenous nucleic acid materials. (A) Upon displacement by the desired DNA or RNA target (Scheme 4) and cleavage of the N-terminal disulfide bond by a reducing agent, T2 undergoes intramolecular 'native chemical ligation' reaction, resulting in the expulsion of the N-terminal domain (n). The now shorter T3, with only a single arm (ba, 5-Int in length) capable of forming natural Watson-Crick base-pairs, will be impervious to recognition by endogenous DNA or RNA molecules. (B) Mechanism of 'native chemical ligation' reaction.

Figure 25:
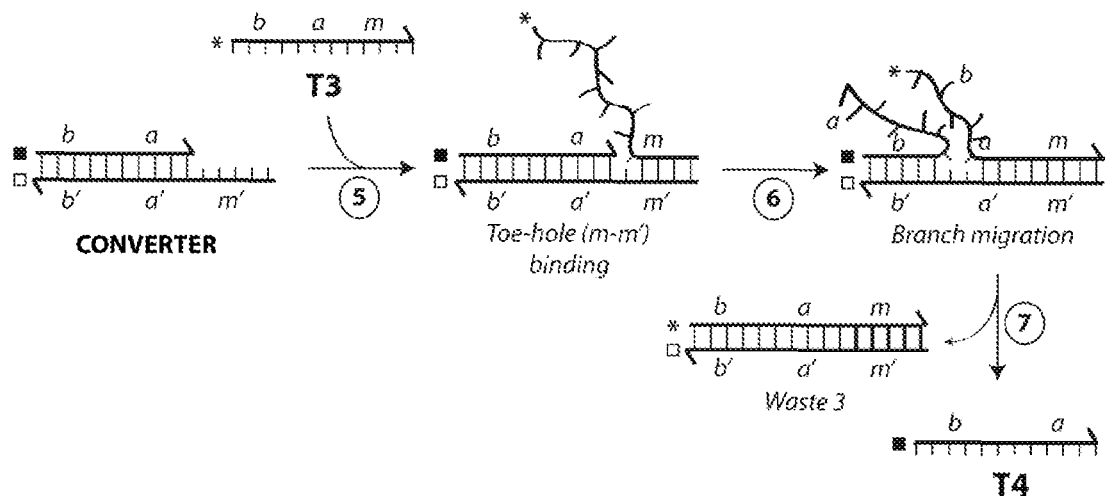
FIG. 25 shows the converter, where PNA can be used as a converter to transform a right-handed operant into a left-hand, and vice versa, based on a strand exchange mechanism.

The next component is the converter, as detailed in FIG. 25. PNA in general does not have a well-defined conformation, and as such it can hybridize to either a right-handed or left-handed γPNA. Depending on the binding free energy of the two duplex systems, PNA can be used as a converter to transform a right-handed operant into a left-hand, and vice versa, based on the strand exchange mechanism shown above. The converter in this case is comprised of a left-handed γPNA (top strand) and a non-helical preference PNA (bottom strand), hybridized to one another to form a left-handed duplex with a toe-hold region m'. Since m' contains unnatural nucleobases as recognition elements, it cannot hybridize to DNA or RNA except for its complementary domain m in T3. Toe-hold binding of T3 to the converter (5), followed by branch migration (6) and strand displacement (7), results in the release of T4. Strand displacement reaction is favored because the thermodynamic stability of waste 3 is greater than that of the converter.

Figure 26:
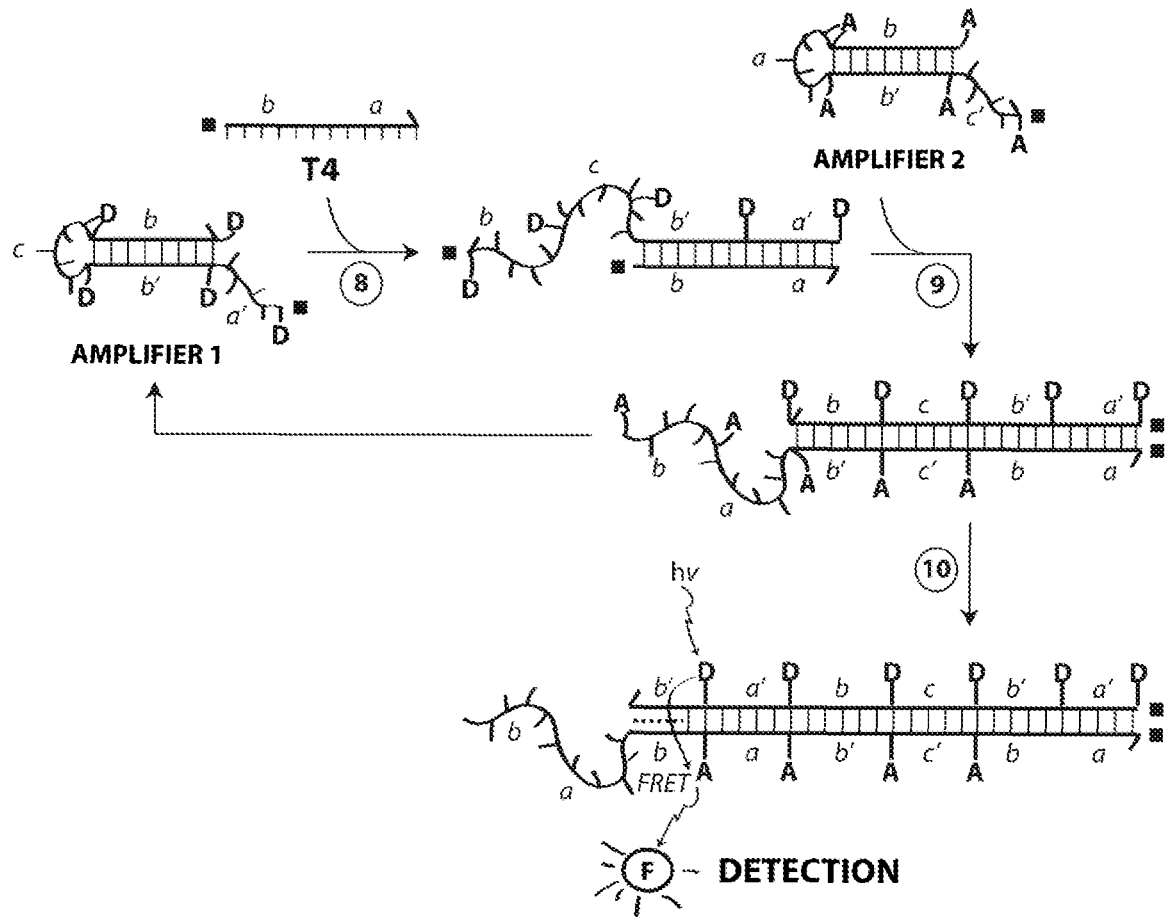
FIG. 26 illustrates the amplifier, which consists of two left-handed (LH) γPNA probes (Amplifier 1 and 2).

FIG. 26 shows the final component of the present invention, the amplifier. The amplification system consists of two left-handed (LH) γPNA probes (Amplifier 1 and 2), and as such they are impervious to recognition by endogenous genetic materials. Despite their sequence complementarity, the two probes are unable to hybridize to one another in the absence of a catalytic strand, at least on the experimental timescale, because the hairpin domains (c and a) are shielded by the stem regions. The amplification process commences upon the release of the T4 catalytic strand, which then bind to the first amplifier (8), and then to the second (9), causing a cascade reaction resulting in the formation of an extended duplex structure (10). Several detection strategies could be envisioned taking advantage conformational changes following hybridization, but as an example a FRET (Fluorescent Resonance Energy Transfer) system is shown. Other possible detection systems include fluorescent dequenching, fluorescent activation, enzyme-linked immunosorbent assay (ELISA), tyramide signal amplification (TSA), just to name a few.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A method of amplifying a target nucleic acid sequence, comprising:
   a) contacting a target nucleic acid with a composition comprising:
      i) a sensor comprising:
         (1) a protecting (P) strand of achiral peptide nucleic acid and/or right-handed gamma-peptide nucleic acid (RγPNA) having an N-terminal end and a C-terminal end, comprising, in an N-terminal to C-terminal direction, a first section having nucleobase sequence n, second section having nucleobase sequence m comprising unnatural nucleobases, third section having nucleobase sequence a and fourth section having nucleobase sequence b and comprising an N-terminal cysteine, sulfhydryl or protected sulfhydryl group, and a thioester bond linking sections m and n;

(2) a sensing (S) strand of RγPNA or achiral peptide nucleic acid (achiral PNA) having an N-terminal end and a C-terminal end, hybridized to the P strand, comprising, in an N-terminal to C-terminal direction a first section having nucleobase sequence b' complementary to sequence b, a second section having nucleobase sequence a' complementary to sequence a, a third section having nucleobase sequence n' complementary to sequence n and a fourth, toe-hold section having nucleobase sequence o', the S strand having a sequence complementary to a nucleotide sequence of a nucleic acid and comprising the target sequence, having a 5' end and a 3' end, comprising, in a 5' to 3' direction, without intervening nucleobases a first section having nucleobase sequence 0 complementary to sequence o', a second section having nucleobase sequence N complementary to sequence n', a third section having nucleobase sequence A complementary to sequence a' and a fourth section having nucleobase sequence B complementary to sequence b', wherein hybridization of the target nucleic acid to the S strand displaces the P strand, and the first section of the displaced P strand having nucleobase sequence n is removed by self-splicing;

ii) a converter comprising:
(1) an achiral peptide nucleic acid (achiral PNA) having an N-terminal end and a C-terminal end, comprising, in an N-terminal to C-terminal direction, a first section having nucleobase sequence b' complementary to sequence b, a second section having nucleobase sequence a' complementary to sequence a, and a third section having nucleobase sequence m' having unnatural nucleobases complementary to sequence m; and
(2) a left-handed γPNA (LγPNA) having an N-terminal end and a C-terminal end, hybridized to the achiral PNA, comprising, in an N-terminal to C-terminal direction a first section having nucleobase sequence b complementary to sequence b' of the PNA, and a second section having nucleobase sequence a' complementary to sequence a of the PNA, wherein the displaced P strand hybridizes to the achiral PNA of the converter, displacing the L γPNA from the converter; and b) detecting the displaced L γPNA,
wherein, other than where sequences are indicated as being complementary, the sequences A, a, a', B, b, b', N, n, n', 0, o', m or m' are not complementary to each other.

2. The method of claim 1, in which the displaced LγPNA is detected by a cascading hybridization chain reaction.

3. The method of claim 2, in which the composition further comprises:
iii) a first amplifier of LγPNA having an N-terminal end and a C-terminal end, comprising, in an N-terminal to C-terminal direction a first section having nucleobase sequence b, a second section having nucleobase sequence c, a third section having nucleobase sequence b' and a fourth section having nucleobase sequence a'; and
iii) a second amplifier of LγPNA having an N-terminal end and a C-terminal end, comprising, in an N-terminal to C-terminal direction, a first section having nucleobase sequence c', a second section having nucleobase sequence b', a third section having nucleobase sequence a' and a fourth section having nucleobase sequence b, wherein sequences of c and c' do not hybridize to sequences a, a', b or b'.

4. The method of claim 3, wherein the first amplifier comprises a first member of a Fluorescent Resonance Energy Transfer (FRET) pair, an excimer pair, a fluorescence dequenching pair, or a fluorescence activation pair, and the second amplifier comprises a second member of the FRET pair, the excimer pair, the fluorescence dequenching pair, or the fluorescence activation pair, respectively.

5. The method of claim 1, wherein each of section a, b, n and o' consists of from 2 to 5 bases, and m consists of from 3 to 7 bases.

6. The method of claim 1, wherein the P strand is from 14 to 21 bases in length.

7. The method of claim 1, wherein the first section of the P strand is achiral PNA and the second, third and fourth sections of the P strand is RγPNA.

8. The method of claim 1, wherein the unnatural nucleobases are selected from the group consisting of isoguanine, isocytosine, xanthine, diaminopyridine; 2-amino-6-dimethylaminopurine, 2-oxopyridine, 6-amino-5-nitro-3-(1'- β-D-2'-deoxyribofuranosyl)-2(1H)-pyridone (dZ), 2-amino-8-(1'-β-D-2'-deoxyribofuranosyl)-imidazo[1,2-a]-1,3,5-triazin-4(8H)-one (dP),

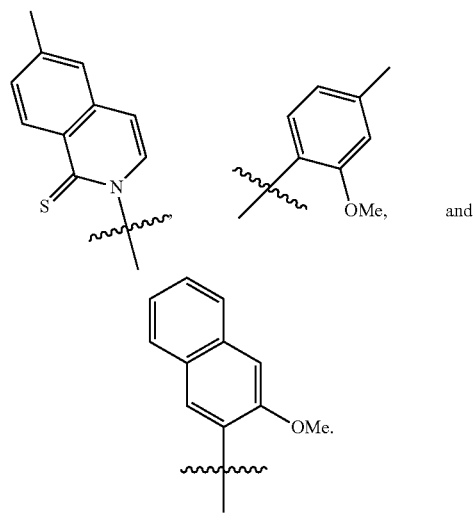

9. A composition for use in detection of a target nucleic acid, comprising:
a) a sensor comprising:
i) a protecting (P) strand of achiral peptide nucleic acid and/or right-handed gamma-peptide nucleic acid (RγPNA) having an N-terminal end and a C-terminal end, comprising, in an N-terminal to C-terminal direction, a first section having nucleobase sequence n, second section having nucleobase sequence m comprising unnatural nucleobases, third section having nucleobase sequence a and fourth section having nucleobase sequence b and comprising an N-terminal cysteine, sulfhydryl or protected sulfhydryl group, and a thioester bond linking sections m and n;
  ii) a sensing (S) strand of RγPNA or achiral peptide nucleic acid (achiral PNA) having an N-terminal end and a C-terminal end, hybridized to the P strand, comprising, in an N-terminal to C-terminal direction a first section having nucleobase sequence b' complementary to sequence b, a second section having nucleobase sequence a' complementary to sequence a, a third section having nucleobase sequence n' complementary to sequence n and a fourth, toe-hold section having nucleobase sequence o', the S strand having a sequence complementary to a nucleotide sequence of a nucleic acid and comprising the target sequence, having a 5' end and a 3' end, comprising, in a 5' to 3' direction, without intervening nucleobases a first section having nucleobase sequence 0 complementary to sequence o', a second section having nucleobase sequence N complementary to sequence n', a third section having nucleobase sequence A complementary to sequence a' and a fourth section having nucleobase sequence B complementary to sequence b', wherein hybridization of the target nucleic acid to the S strand displaces the P strand, and the first section of the displaced P strand having nucleobase sequence n is removed by self-splicing;
b) a converter comprising,
  i) an achiral peptide nucleic acid (achiral PNA) having an N-terminal end and a C-terminal end, comprising, in an N-terminal to C-terminal direction, a first section having nucleobase sequence b' complementary to sequence b, a second section having nucleobase sequence a' complementary to sequence a, and a third section having nucleobase sequence m' having unnatural nucleobases complementary to sequence m; and
  ii) a left-handed γPNA (LγPNA) having an N-terminal end and a C-terminal end, hybridized to the achiral PNA, comprising, in an N-terminal to C-terminal direction a first section having nucleobase sequence b complementary to sequence b' of the PNA, and a second section having nucleobase sequence a' complementary to sequence a of the PNA, wherein the displaced P strand hybridizes to the achiral PNA of the converter, displacing the LγPNA from the converter; and
wherein, other than where sequences are indicated as being complementary, the sequences A, a, a', B, b, b', N, n, n', 0, o', m or m' are not complementary to each other.
10. The composition of claim 9, further comprising:
c) a first amplifier of LγPNA having an N-terminal end and a C-terminal end, comprising, in an N-terminal to C-terminal direction without intervening nucleobases, a first section having nucleobase sequence b, a second section having nucleobase sequence c, a third section having nucleobase sequence b' and a fourth section having nucleobase sequence a'; and
d) a second amplifier of LγPNA having an N-terminal end and a C-terminal end, comprising, in an N-terminal to C-terminal direction without intervening nucleobases, a first section having nucleobase sequence c', a second section having nucleobase sequence b', a third section having nucleobase sequence a' and a fourth section having nucleobase sequence b, wherein sequences of c and c' do not hybridize to sequences a, a', b or b'.
11. The composition of claim 10, wherein the first amplifier comprises a first member of a Fluorescent Resonance Energy Transfer (FRET) pair, an excimer pair, a fluorescence dequenching pair, or a fluorescence activation pair, and the second amplifier comprises a second member of the FRET pair, the excimer pair, the fluorescence dequenching pair, or the fluorescence activation pair, respectively.
12. The composition of claim 9, each of section a, b, n and o' consisting of from 2 to 5 bases, and m consisting of from 3 to 7 bases.
13. The composition of claim 9, wherein the unnatural nucleobases are selected from the group consisting of isoguanine, isocytosine, xanthine, diaminopyridine; 2-amino-6-dimethylaminopurine, 2-oxopyridine, 6-amino-5-nitro-3-(1'-β-D-2'-deoxyribofuranosyl)-2 (1H)-pyridone (dZ), 2-amino-8-(1'-β-D-2'-deoxyribofuranosyl)-imidazo[1,2-a]-1,3,5-triazin-4 (8H)-one (dP),

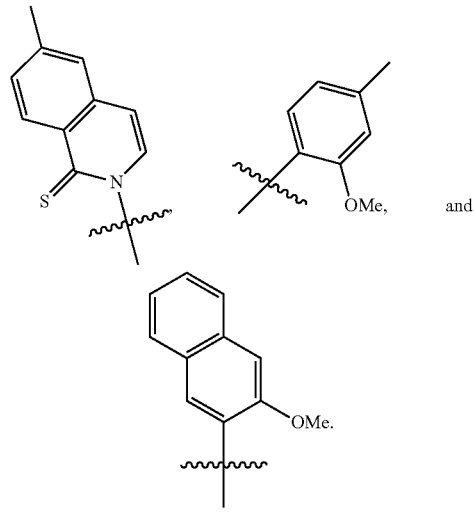

14. A method of detecting a nucleic acid comprising a specific nucleic acid sequence in a sample, comprising:
  a) hybridizing the nucleic acid to a duplex right-handed and/or achiral gamma-peptide nucleic acid (γPNA) comprising a protecting (P) strand comprising, in order a first section comprising the specific nucleic acid sequence, a second section comprising a sequence of unnatural nucleobases, and a third section comprising a sequence of the nucleic acid adjacent to the sequence of the first section, and further comprising a thioester bond between the second and third sections and an N-terminal sulfhydryl group, hybridized to a sensing (S) strand comprising, in order a sequence complementary to the first section and the third section, but not the second section, such that the P strand comprising the specific nucleic acid sequence is displaced by the nucleic acid, and the third section of the P strand is removed by self-splicing between the sulfydryl and thioester;
  b) converting the P strand to an LγPNA by hybridizing the P strand to a duplex converter PNA comprising a first strand of an achiral PNA having a sequence complementary to the P strand hybridized to a second strand of an LγPNA having the same sequence as the first section of the P strand, thereby displacing the LγPNA; and c) amplifying the displaced LγPNA by concatenization of a pair of single-stranded LγPNA amplifiers having a hairpin structure, the first amplifier having, in order, a sequence complementary to the displaced LγPNA, a sequence that is not present in the displaced LγPNA, and a portion of (not the complete sequence) the sequence of the displaced LγPNA such that the hairpin of the first amplifier is opened by binding to the displaced LγPNA, leaving a single-stranded tail comprising the sequence not present in the displaced LγPNA and the portion of the sequence of the displaced LγPNA, the second amplifier comprising a hairpin structure comprising, in order, a first portion having a sequence complementary to the sequence of the single-stranded tail formed by the binding of the LγPNA to the first amplifier and a second portion having the sequence of the LγPNA such that binding of the second amplifier to the single-stranded tail formed by the first amplifier binding to the LγPNA opens the hairpin of the second amplifier, leaving a single-stranded tail having the same sequence as the LγPNA, so that the first amplifier can bind to the single stranded tail resulting from binding of the second amplifier to the single-stranded tail formed by the first amplifier binding to the LγPNA.

15. The method of claim 14, wherein the first amplifier comprises a first member of a Fluorescent Resonance Energy Transfer (FRET) pair, an excimer pair, a fluorescence dequenching pair, or a fluorescence activation pair, and the second amplifier comprises a second member of the FRET pair, the excimer pair, the fluorescence dequenching pair, or the fluorescence activation pair, respectively.

16. The method of claim 14, wherein the sample is a cell, cell lysate or tissue.

* * * * *

UNITED STATES PATENT AND TRADEMARK OFFICE
CERTIFICATE OF CORRECTION

PATENT NO. : 10,851,407 B2
APPLICATION NO. : 15/308901
DATED : December 1, 2020
INVENTOR(S) : Danith H. Ly et al.

Page 1 of 1

It is certified that error appears in the above-identified patent and that said Letters Patent is hereby corrected as shown below:

In the Claims

Column 48, Line 67, Claim 1, delete "(RyPNA)" and insert -- (RγPNA) --

Column 49, Line 10, Claim 1, delete "(RyPNA)" and insert -- (RγPNA) --

Column 49, Line 55, Claim 1, delete "L γPNA" and insert -- LγPNA --

Column 49, Line 56, Claim 1, delete "L γPNA," and insert -- LγPNA, --

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*